US007794972B2

(12) United States Patent
Retallack et al.

(10) Patent No.: US 7,794,972 B2
(45) Date of Patent: Sep. 14, 2010

(54) BENZOATE-AND ANTHRANILATE-INDUCIBLE PROMOTERS

(75) Inventors: Diane M. Retallack, Poway, CA (US); Venkiteswaran Subramanian, San Diego, CA (US)

(73) Assignee: Pfenex Inc., San Diego, CA (US)

( * ) Notice: Subject to any disclaimer, the term of this patent is extended or adjusted under 35 U.S.C. 154(b) by 371 days.

(21) Appl. No.: 11/028,156

(22) Filed: Jan. 3, 2005

(65) Prior Publication Data

US 2005/0202544 A1 Sep. 15, 2005

Related U.S. Application Data

(63) Continuation of application No. PCT/US03/20840, filed on Jul. 3, 2003.

(60) Provisional application No. 60/393,422, filed on Jul. 3, 2002.

(51) Int. Cl.
*C12P 21/02* (2006.01)
*C12N 1/21* (2006.01)
*C07H 21/04* (2006.01)

(52) U.S. Cl. .................. 435/69.1; 435/252.3; 536/23.1

(58) Field of Classification Search ....................... None
See application file for complete search history.

(56) References Cited

U.S. PATENT DOCUMENTS 5,593,860 A 1/1997 Fischer

FOREIGN PATENT DOCUMENTS

| EP | 0345155 A | 12/1989 |
|---|---|---|
| JP | 01-15739 A | 6/1989 |
| JP | 02-084195 | 3/1990 |
| JP | 2002-504379 A | 2/2002 |
| WO | WO 98/20111 | 5/1998 |
| WO | WO 99/43835 | 2/1999 |

OTHER PUBLICATIONS

Tang et al., Genes and Devl., 8:3-58-3067, 1994.*
Cases, I., and De Lorenzo, V., "Expression systems and physiological control of promoter activity in bacteria," *Curr. Opin. Microbiol.*, 1(3), 303-310 (1998).
Hofman-Bang, J., "Nitrogen catabolite repression in *Saccharomyces cerevisiae*," *Mol. Biotechnol.*, 12(1):35-73 (Aug. 1999).
Reznikoff, W.S., "The lactose operon-controlling elements: a complex paradigm," *Mol. Microbiol.*, 6(17):2419-2422 (Sep. 1992).
Stewart, G.C., "Catabolite repression in the gram-positive bacteria: generation of negative regulators of transcription," *J. Cell. Biochem.*, 51(1):25-28 (Jan. 1993).
Amann et al., "Vectors bearing a hybrid trp-lac promoter useful for regulated expression of cloned genes in *Escherichia coli*," 1983, Genes, 25, pp. 167-178.

Brosius et al., "Regulation of ribosomal RNA promoters with a synthetic lac operator," 1984, Proc. Natl Acad. Sci. USA, 81, pp. 6929-6933.
Collier et al., "Regulation of benzoate degradation in *Acinetobacter* sp. strain ADP1 by BenM, a LysR-Type transcriptional activator," Journal of Bacteriology, 1998, 180, pp. 2493-2501.
Duetz et al., "Catabolite repression of the toluene degradation pathway in *Pseudomonas putida* harboring pWW0 under various conditions of nutrient limitation in chemostat culture," 1996, Applied and Environmental Microbiology, 1996, 62, pp. 601-606.
Gallegos et al., "Expression of TOL plasmid xylS gene in *Pseudomonas putida* occurs from a sigma70-Dependent Promoter or from sigma70- and sigma54- dependent tandem promoters according to the compound used for Ggrowth," Journal of Bacteriology, 1996, 178, pp. 2356-2361.
Goeddel et al., "Direct expression in *Escherichia coli* of a DNA sequence coding for human growth hormone," 1979, Nature, 281, pp. 544-548.
Hester et al., "Catabolite repression control by crc in 2xYT medium is mediated by posttranscriptional regulation of bkdR expression in *Pseudomonas putida*," 2000, Journal of Bacteriology, 182, pp. 1150-1153.
Hester et al., "Crc is involved in catabolite repression control of the bkd operons of *Pseudomonas putida* and *Pseudomonas aeruginosa*," 2000, Journal of Bacteriology, 182, pp. 1144-1149.
Lu et al., "The gdhB gene of *Pseudomonas aeruginosa* encodes an arginine-inducible NAD+-dependent glutamate dehydrogenase which is subject to allosteric regulation," 2001, Journal of Bacteriology, 183, pp. 490-499.
Marin et al., "The alkane hydroxylase gene of *Burkholderia cepacia* RR10 is under catabolite repression control," 2001, Journal of Bacteriology, 183, pp. 4202-4209.
Mosqueda et al., "A set of genes encoding a second toluene efflux system in *Pseudomonas putida* DOT-TIE is linked to the tod genes for toluene metabolism," 2000, Journal of Bacteriology, 182, pp. 937-943.
Nishijyo et al., "Molecular characterization and regulation of an operon encoding a system for transport of arginine and ornithine and the ArgR regulatory protein in *Pseudomonas aeruginosa*," 1998, Journal of Bacteriology, 180, pp. 5559-5566.
Ochs et al., "Amino acid-medicated induction of the basic amino acid-specific outer membrane porin OprD from *Pseudomonas aeruginosa*," 1999, Journal of Bacteriology, 181, pp. 5426-5432.
Sanchez-Romero et al., "Genetic engineering of nonpathogenic *Pseudomanas* strains as biocatalysts for industrial and environmental processes," 1999, Manual of Industrial Microbiology and Biotechnology, pp. 460-474.
Santos et al., "Physiological analysis of the expression of the degradation gene cluster in *Pseudomonas fluorescens* ST," 2000, Applied and Environmental Microbiology, 66, pp. 1305-1310.

(Continued)

*Primary Examiner*—Nancy Vogel
(74) *Attorney, Agent, or Firm*—Wilson Sonsini Goodrich & Rosati

(57) ABSTRACT

Novel benzoate- or anthranilate-inducible promoters, and novel tandem promoters, and variants and improved mutants thereof, useful for commercial prokaryotic fermentation systems, nucleic acid constructs containing the promoters, expression systems using them, methods for expressing proteins by use thereof, and proteins expressed thereby.

14 Claims, 21 Drawing Sheets

OTHER PUBLICATIONS

Schweizer, "Vectors to express foreign genes and techniques to monitor gene expression for *Pseudomonads*," 2001, Current Opinion in Biotechnology, 12, pp. 439-445.

Slater et al., "The expression of foreign DNA in bacteria," 2000, Molecular Biology and Biotechnology, pp. 125-154.

Vilchez et al., "Control of expression of divergent *Pseudomonas putida* put promoters for proline catabolism," 2000, Applied and Environmental Microbiology, 66, pp. 5221-5225.

Bundy et al., "Synergistic transcriptional activation by one regulatory protein in response to two metabolites", PNAS, May 28, 2002, 99(11), pp. 7693-7698.

Nojiri et al. (2001) Genetic Characterization and Evolutionary Implications of a *car* Gene Cluster in the Carbazole Degrader *Pseudomonas* sp. Strain CA10.

NCBI Database Accession No. AY02691401, submitted Jan. 31, 2001.

NCBI Database Accession No. AF009224, submitted Dec. 17, 2001.

Office Action issued in corresponding Japanese Patent Application No. 2004-519773.

* cited by examiner

FIGURE 5

```
Pben509  CCAACGTCAG TGAACGTTCG CTGTACAGCC TGTTTGAGCG CCAGGTGGGG CTGTCGCCGC GCGATTACGT Pben509  ACGCCGCTGC AAGCTCGAAC GCGTACATGC ACGCTTGCAA CTAAGCAGCA CGCGCAGCGT GACCGAGGTG Pben509  GCTTTGGACC ATGGGTTCAT GCACCTAGGG CGGTTTTCCG AAGCCTATCG CAAACGCTTC GGCGAACTGC Pben509  CGTCGCAGAC CTGGAAACGC CATCGTTAAG CGACGTGCGC CTGGCGGATA GCGATGTGCA GGCAGCGGAT
Pben278                                 GTTAAG CGACGTGCGC CTGGCGGATA GCGATGTGCA GGCAGCGGAT Pben509  ATTGACGGGC AGGGCGAGCA CGTACGGTGA GGGCGCCTGA TACAAGAACA ACGGAGGGCC CGCCCCATGA
Pben278  ATTGACGGGC AGGGCGAGCA CGTACGGTGA GGGCGCCTGA TACAAGAACA ACGGAGGGCC CGCCCCATGA Pben509  TCAGTACACT CGACCGACTC GCCTGCCAAT TGCGCGAGTC CGTACAGGAA GACCCCGCCA CTGGGGTGTT
Pben278  TCAGTACACC CGACCGACTC GCCTGCCAAT TGCGCGAGTC CGTACAGGAA GACCCCGCCA CTGGGGTGTT Pben509  CCGCTGCCGC CGGCGACATCT TCACCGACCC CGACCTGTTT GCCCTGGAGA TGAAACACAT CTTCGAAGGC
Pben278  CCGCTGCCGC CGGCGACATCT TCACCGACCC CGACCTGTTT GCCCTGGAGA TGAAACACAT CTTCGAAGGC Pben509  GGGTGGATCT ACCTGGCCC
Pben278  GGGTGGATCT ACCTGGCCC
```

FIGURE 7A

```
Pant+AntR    TATCGCAGGC AAGCCAGCTC CCACAGATTG TTTTTCATCC AGTTCAAGTA ATGCGCAGGC GCTTGCGCTG Pant+AntR    CAATGTCTGG CTGGGCGACT CATCGAACAG CTTGCGGTAC TCCGCCGAAA ACCGCCCCAA ATGCGTAAAC Pant+AntR    CCCCAACCCA GGGCGATTTC AGAGATGGTG CGGATCGAGC CCTGCTCCAG AATTTCTTGG CGCACCGCCC Pant+AntR    CCAACCGATG CTTCTTCAAA TACGACATGG GCGACAGTGC GAAGTACTTG CGAAACGCAT CGAACAGTTT Pant+AntR    GAAACGCGAC ACGCCCGCCG CCGCTTCCAG GTCTTCCAGG TGCAGCGCTT CACGGGCGTT GTCGTGGATA Pant+AntR    AATTGCCGCG CGCGGATCAG GTAGTGCGGC AGTTTCACCC CCAGCACGTC GCGCAGTTCT TCGGAGTAGT Pant+AntR    TATTCGGTTG GGCCAGGATC AGGCCCTTGA TCAGCGAGCT TTCCAGGTCG CGAGTAAACG CCGCCTGCTC Pant+AntR    GTACAGTTCG CTGCTGCGCT CCAGTTCGGC GATGAAATAA CGCGCCATGC GCCACCACGA AGCCGGTGCT Pant+AntR    CCGTCCACAG CATCCATCAC CGACTCAAAG CGCAGCGGCG CATCAATGGG CCGTTGCAGC AAACCTTCCA Pant+AntR    GCGACTCGCT CATCGCCGCA CGGGTGATTA CCACCTGCAA CTTGCGGCAG TCACCGGAAA TCGCCAGCAC
Pant713               CTCGCT CATCGCCGCA CGGGTGATTA CCACCTGCAA CTTGCGGCAG TCACCGGAAA TCGCCAGCAC
Pant705               CTCGCT CATCGCCGCA CGGGTGATTA CCACCTGCAA CTTGCGGCAG TCACCGGAAA TCGCCAGCAC Pant+AntR    CTGATGCTCA TTGGGCGAAA TGATCACGCC TGGCAGGCTC TTGGTCGCGG TTGGAACTGA GACGTTCACC GTTCTTGCTC
Pant713       CTGATGCTCA TTGGGCGAAA TGATCACGCC TGGCAGGCTC TTGGTCGCGG TTGGAACTGA GACGTTCACC GTTCTTGCTC
Pant705       CTGATGCTCA TTGGGCGAAA TGATCACGCC TGGCAGGCTC TTGGTCGCGG TTGGAACTGA GACGTTCACC GTTCTTGCTC Pant+AntR    AGCTCCTGCT CGCCCACCAG TGGCAGGCTC AAGCTGTAGC TGCTGAAGTG CTCGGCGTCT TCGATGTCGA
Pant713      AGCTCCTGCT CGCCCACCAG TGGCAGGCTC AAGCTGTAGC TGCTGAAGTG CTCGGCGTCT TCGATGTCGA
Pant705      AGCTCCTGCT CGCCCACCAG TGGCAGGCTC AAGCTGTAGC TGCTGAAGTG CTCGGCGTCT TCGATGTCGA
```

FIGURE 7B

| | | | | | | | | |
|---|---|---|---|---|---|---|---|---|
| Pant+AntR | TGGTCACATC | AGTGCCGTAC | TCGATCACGC | CCAGGGTGGT | GGCGCGGGAT | TTGAACACGT | TGGCGCTGTG |
| Pant713 | TGGTCACATC | AGTGCCGTAC | TCGATCACGC | CCAGGGTGGT | GGCGCGGGAT | TTGAACACGT | TGGCGCTGTG |
| Pant705 | TGGTCACATC | AGTGCCGTAC | TCGATCACGC | CCAGGGTGGT | GGCGCGGGAT | TTGAACACGT | TGGCGCTGTG |
| | | | | | | | | |
| Pant+AntR | GTGAAAGCGC | AGGCGCTCGG | GGGTTGCCGT | CGCCAGGCGA | TGGGGCCCGC | AGATGCCGGA | CATCCAGCTG |
| Pant713 | GTGAAAGCGC | AGGCGCTCGG | GGGTTGCCGT | CGCCAGGCGA | TGGGGCCCGC | AGATGCCGGA | CATCCAGCTG |
| Pant705 | GTGAAAGCGC | AGGCGCTCGG | GGGTTGCCGT | CGCCAGGCGA | TGGGGCCCGC | AGATGCCGGA | CATCCAGCTG |
| | | | | | | | | |
| Pant+AntR | CGCGCGCCTT | CCAGGTCGAA | GCGTTGAATA | TGAATATCGC | GTGTCTGACT | AGTCATCAGG | GTGCACCCAC |
| Pant713 | CGCGCGCCTT | CCAGGTCGAA | GCGTTGAATA | TGAATATCGC | GTGTCTGACT | AGTCATCAGG | GTGCACCCAC |
| Pant705 | CGCGCGCCTT | CCAGGTCGAA | GCGTTGAATA | TGAATATCGC | GTGTCTGACT | AGTCATCAGG | GTGCACCCAC |
| Pant311 | | | | | | CAGG | GTGCACCCAC |
| | | | | | | | | |
| Pant+AntR | GGCGGTTAGG | CGTTTGCGCG | CTCTGACGGC | GCGTCGTTGA | ACCTCGACAG | CAAGTTCCAG | GCCACGCCAG |
| Pant713 | GGCGGTTAGG | CGTTTGCGCG | CTCTGACGGC | GCGTCGTTGA | ACCTCGACAG | CAAGTTCCAG | GCCACGCCAG |
| Pant705 | GGCGGTTAGG | CGTTTGCGCG | CTCTGACGGC | GCGTCGTTGA | ACCTCGACAG | CAAGTTCCAG | GCCACGCCAG |
| Pant311 | GGCGGTTAGG | CGTTTGCGCG | CTCTGACGGC | GCGTCGTTGA | ACCTCGACAG | CAAGTTCCAG | GCCACGCCAG |
| | | | | | | | | |
| Pant+AntR | TGCAGTTCTC | ACTGGGTGGA | TAGCAACGGT | CGACTATGTG | GATAAACCCC | AGAGTTTTGC | GACCATCGCC |
| Pant713 | TGCAGTTCTC | ACTGGGTGGA | TAGCAACGGT | CGACTATGTG | GATAAACCCC | AGAGTTTTGC | GACCATCGCC |
| Pant705 | TGCAGTTCTC | ACTGGGTGGA | TAGCAACGGT | CGACTATGTG | GATAAACCCC | AGAGTTTTGC | GACCATCGCC |
| Pant311 | TGCAGTTCTC | ACTGGGTGGA | TAGCAACGGT | CGACTATGTG | GATAAACCCC | AGAGTTTTGC | GACCATCGCC |
| | | | | | | | | |
| Pant+AntR | CGCCATCACA | GTAGCGCATG | CCGTCACCGG | CGCGCACCGT | CATGGGTATT | TGCCGCCCAA | CTTTGCGGCC |
| Pant713 | CGCCATCACA | GTAGCGCATG | CCGTCACCGG | CGCGCACCGT | CATGGGTATT | TGCCGCCCAA | CTTTGCGGCC |
| Pant705 | CGCCATCACA | GTAGCGCATG | CCGTCACCGG | CGCGCACCGT | CATGGGTATT | TGCCGCCCAA | CTTTGCGGCC |
| Pant311 | CGCCATCACA | GTAGCGCATG | CCGTCACCGG | CGCGCACCGT | CATGGGTATT | TGCCGCCCAA | CTTTGCGGCC |

FIGURE 7C

| | | | | | | |
|---|---|---|---|---|---|---|
| Pant+AntR | TACGTTCCCC | CATTAAGCGG | ATAGCCCGCC | ACCGCATCGC | AGCCGCTTAA | TGGCTCACCG | TTTAGCCATG |
| Pant713 | TACGTTCCCC | CATTAAGCGG | ATAGCCCGCC | ACCGCATCGC | AGCCGCTTAA | TGGCTCACCG | TTTAGCCATG |
| Pant705 | TACGTTCCCC | CATTAAGCGG | ATAGCCCGCC | ACCGCATCGC | AGCCGCTTAA | TGGCTCACCG | TTTAGCCATG |
| Pant311 | TACGTTCCCC | CATTAAGCGG | ATAGCCCGCC | ACCGCATGC  | AGCCGCTTAA | TGGCTCACCG | TTTAGCCATG |

| | | |
|---|---|---|
| Pant+AntR | ATCAAAAGGT | GCCTCCC |
| Pant713 | ATCAAAAGGT | GCCTCCC |
| Pant705 | ATCAAAAGG  |  |
| Pant311 | ATCAAAAGGT | GCCTCCC |

FIGURE 11

```
Pben509   CCAACGTCAG TGAACGTTCG CTGTACAGCC TGTTTGAGCG CCAGGTGGGG CTGTCGCCGC GCGATTACGT
2d3       CCAACGTCAG TGAACGTTCG CTGTACAGCC TGTTTGAGCG CCAGGTGGGG CTGTCGCCGC GCGATTACGT
21b5      CCAACGTCAG TGAACGTTCG CTGTACAGCC TGTTTGAGCG CCAGGTGGGG CTGTCGCCGC GCGATTACGT Pben509   ACGCCGCTGC AAGCTCGAAC GCGTACATGC CTAAGCAGCA ACGCTTGCAA CGCGCAGCGT GACCGAGGTG
2d3       ACGCCGCTGC AAGCTCGAAC GCGTACATGC CTTAGCAGCA ACGCTTGCAA CGCGCAGCGT GACCGAGGTG
21b5      ACGCCGCTGC AAGCTCGAAC GCGTACATGC CTAAGCAGCA ACGCTTGCAA CGCGCAGCGT GACCGAGGTG Pben509   GCTTTGGACC ATGGGTTCAT GCACCTAGGG AAGCCTATCG CGGTTTTCCG CAAACGCTTC GGCGAACTGC
2d3       GCTTTGGACC ATGGGTTCAT GCACCTAGGG AAGCCTATCG CGGTTTTCCG CAAACGCTTC GGCGAACTGC
21b5      GCTTTGGACC ATGGGTTCAT GCACCTAGGG AAGCCTATCG CGGTTTTCCG CAAACGCTTC GGCGAACTGC Pben509   CGTCGCAGAC CTGGAAACGC CATCGTTAAG CGACGTGCGC CTGGCGGATA GCGATGTGCA GGCAGCGGAT
2d3       CGTCGCAGAC CTGGAAACGC CATCGTTAAG CGACGTGCGC CTGGCGGATA GCGATGTGCA GGCAGCGGAT
21b5      CGTCGCAGAC CTGGAAACGT CATCGTTAAG CGACGTGCGC CTGGCGGATA GCGATGTGCA GGCAGCGGAT Pben509   ATTGACGGGC AGGGCGAGCA CGTACGGTGA GGGCGCCTGA TACAAGAACA ACGGAGGGCC CGCCCCATGA
2d3       ATTGACGGGC AGGGCGAGCA CGTACGGTGA GGGCGCCTGA TACAAGAACA ACGGAGGGCC CGCCCCATGA
21b5      ATTGACGGGC AGGGCGAGCA CGTACGGTAA GGGCGCCTGA TACAAGAACA ACGGAGGGCC CGCCCCATGA Pben509   TCAGTACACT CGACCGACTC GCCTGCCAAT TGCGCGAGTC CGTACAGGAA GACCCCGCCA CTGGGGTGTT
2d3       TCAGTACACT CGACCGACTC GCCTGCCAAT TGCGCGAGTC CGTACAGGAA GACCCCGCCA CTGGGGTGTT
21b5      TCAGTACACT CGACCGACTC GCCTGCCAAT TGCGCGAGTC CGTACAGGAA GACCCCGCCA CTGGGGTGTT Pben509   CCGCTGCCGC CGCGACATCT TCACCGACCC CGACCTGTTT GCCCTGGAGA TGAAACACAT CTTCGAAGGC
2d3       CCGCTGCCGC CGCGACATCT TCACCGACCC CGACCTGTTT GCCCTGGAGA TGAAACACAT CTTCGAAGGC
21b5      CCGCTGCCGC CGCGACATCT TCACCGACCC CGACCTGTTT GCCCTGGAGA TGAAACACAT CTTCGAAGGC Pben509   GGGTGGATCT ACCTGGCCC
2d3       GGGTGGATCT ACCTGGCCC
21b5      GGGTGGATCT ACCTGGCCC
```

BENZOATE-AND ANTHRANILATE-INDUCIBLE PROMOTERS

This application is a continuation of co-pending Application No. PCT US2003/020840, published as WO 2004/005211, filed Jul. 3, 2003, which claims priority to U.S. Provisional Application No. 60/393,422, filed Jul. 3, 2002.

REFERENCE TO SEQUENCE LISTING SUBMITTED ELECTRONICALLY

The official copy of the sequence listing is submitted electronically via EFS-Web as an ASCII formatted sequence listing with a file named "344269 SequenceListing.txt", created on Jul. 31, 2009, and having a size of 86 kilobytes and is filed as an Amendment to the specification on Jul. 31, 2009. The sequence listing contained in this ASCII formatted document is part of the specification and is herein incorporated by reference in its entirety.

BACKGROUND

Gene expression in bacteria, as in any organism, requires that a promoter be present in the regulatory region located 5' (i.e. upstream) from the coding sequence in order to direct the gene's transcription. Promoters are classified as constitutive promoters and regulated promoters. In commercially useful bacterial expression systems, regulated promoters have proven particularly useful because they permit increase in the organismal biomass while a desired gene(s) is inactive. This allows the host organism to devote maximal energy to cell division and growth. When the regulated promoter is then activated/induced, more cells will be available to express the desired gene(s), thereby increasing the yield of the desired gene product(s).

Regulated promoters include: (1) activatable promoters, i.e. promoters that are inactive until an activator protein binds to the 5' regulatory region; and (2) repressible promoters, i.e. promoters that are inactive while the 5' regulatory region is bound by a repressor protein. Some genes or operons are regulated by more than one mechanism. For example, some bacterial genes and operons are subject to both a first, activation or derepression regulatory mechanism, and a second regulatory mechanism, called "catabolite repression." Catabolite repression, also called "glucose catabolite repression" or "carbon catabolite repression," is a phenomenon in which gene(s) under the control of a regulated promoter are also maintained in an unexpressed state until the concentration of glucose (the primary carbon source) falls below a threshold level, e.g., until conditions of glucose starvation. In other words, such a gene(s) cannot be expressed until two conditions are met: 1) glucose reduction/starvation and 2) activation or derepression of the regulated promoter. The occurrence of only one or the other condition is not sufficient to achieve expression of such gene(s). Among the genes and operons that have been found subject to catabolite repression are many that encode enzymes and/or pathways needed to utilize non-glucose carbon sources, i.e. alternative carbon sources.

The mechanism by which catabolite repression is effected is still undergoing intense scrutiny. In the case of some catabolite-repressed operons in *E. coli*, a transcriptional level of control has been assigned, in which catabolite repression is overcome by an "activatable promoter" mechanism. For example, the *E. coli* lactose operon (lacZYA) is maintained in an untranscribable state until glucose starvation permits a "catabolite activator protein" to bind to the operon's 5' regulatory region; then, when lactose is present, Lac repressor protein is removed from a separate site(s) (the lac operator(s)) in the 5' regulatory region, causing derepression, and transcription is initiated. Both conditions, i.e. both glucose starvation and the presence of lactose, are required for formation of lac operon-encoded mRNA in *E. coli*.

In some cases, post-transcriptional controls are suspected. For example, there is evidence that, in Pseudomonads and closely related species, catabolite repression involving the crc gene is mediated post-transcriptionally. This is seen from studies of the regulation of bdkR [Ref. 7]. The bdkR protein, a transcriptional activator, is involved in the regulation of expression of branched-chain keto acid dehydrogenase in *Pseudomonas putida*. The data presented show that, in rich media, there is no bdkR protein detectable in wild type *P. putida*, despite the presence of bdkR transcripts. However, in a mutant *P. putida* in which crc is impaired or inactivated, bkdR protein is detected, bdkR transcript levels are slightly lower than those found in the wild type strain, and the transcript of the bdkR-regulated gene, bdkA, is induced about four-fold. Moreover, mutations identified in mutants in which the catabolite repression of bdkR is overcome, have been mapped to the crc gene, or to its cognate gene, vacB. In *Shigella flexneri*, the vacB protein regulates virulence genes post-transcriptionally; this presents additional, although circumstantial, evidence that crc acts post-transcriptionally [Ref. 13].

In commercial, prokaryotic systems, one of the key technological challenges associated with the production of proteins and chemicals by fermentation is total control of the transgene expression. The promoter selected for use in expressing the transgene of interest should have the following qualities. It should:

1. Separate growth from reaction;
2. Control gene expression for efficient/maximum product yield;
3. Induce the gene of interest at low/no cost; and
4. Allow no significant level of transcription in the repressed or non-induced state.

For these reasons, regulated promoters are relied upon extensively. In particular, the lac promoter (i.e. the lacZ promoter) and its derivatives, especially the tac and trc promoters described in U.S. Pat. No. 4,551,433 to DeBoer, and the related promoters listed in

TABLE 1

Commercial lac Promoters, Derivatives & Relatives

| Promoter | Commercial Inducer | Bacterial Host Cell(s) | Reference(s) |
|---|---|---|---|
| Ptac16 | IPTG | *E. coli*, Pseudomonads | 3, 4 |
| Ptac17 | IPTG | *E. coli*, Pseudomonads | 3 |
| PlacUV5 | IPTG | *E. coli*, Pseudomonads | 3 |
| Plac | IPTG | *E. coli* | 3, 4 |
| Plac(down) | IPTG | *E. coli* | 3 |
| T7 | IPTG | *E. coli*, Pseudomonads | 3, 4 |

In a typical commercial, bacterial fermentation system, the host cell contains a construct in which a tac promoter is operably attached to a gene or operon whose expression is desired. The lacI gene, which is a constitutively expressed gene that encodes the Lac repressor protein which binds to the lac operator, is also included in the bacterial host cell (multiple copies of the lacI gene are usually included therein).

After growth of a desired quantity or density of biomass, an inducer is added to the culture in order to derepress the tac promoter and permit expression of the desired gene or operon.

In commercial fermentation systems using a lac-type promoter, such as the tac promoter, the gratuitous inducer, IPTG (isopropyl-β-D-1-thiogalactopyranoside, also called "isopropylthiogalactoside"), is almost universally employed. However, IPTG is expensive and must be carefully controlled since it is significantly toxic to biological systems. Standard IPTG preparations are currently available at about US$18 per gram or about US$125 per 10 grams; these IPTG preparations also contain dioxane, which is likewise toxic to biological systems. Dioxane-free IPTG is also available on the market, but costs about twice the price of standard IPTG (i.e. currently about US$36 per gram or about US$250 per 10 grams). In addition to the problems of expense and high toxicity to the fermentation system itself, in situations in which the expression product or fermentation product is to be marketed, environmental and health regulatory issues arise in regard to the presence of IPTG therein, since IPTG also poses toxicity risks to humans, animals, and other biological organisms.

As a result, there is a need for promoters that are both useful for commercial fermentation production systems and activated by non- or low-toxicity inducers.

A further drawback of the use of lac promoters and their derivatives is that these promoters are "leaky" in that, even in a native, repressed state, the promoter permits a relatively high background level of expression. Therefore, multiple copies of the LacI repressor protein gene are usually included within the expression host cell in order to increase the degree of repression of the lac-type promoter. As a result, there is a need for promoters that are both useful for commercial fermentation systems and readily susceptible of being tightly controlled in an inactive state until induced.

In light of these concerns, several other, non-lac-type promoters have been proposed for controlling gene expression in commercial, prokaryotic fermentation systems (see Table 2).

TABLE 2

Proposed Inducible Commercial non-lac Promoters

| Promoter | Inducer | Bacterial Host Cell(s) | Reference(s) |
|---|---|---|---|
| $\lambda P_R$ | High temperature | E. coli, Pseudomonads | 3, 4 |
| $\lambda P_L$ | High temperature | E. coli, Pseudomonads | 3, 4 |
| Pm | Alkyl- or halo-benzoates | Pseudomonads | 4, 5 |
| Pu | Alkyl- or halo-toluenes | Pseudomonads | 5 |
| Psal | Salicylates | Pseudomonads | 5 |
| Para | Arabinose in the absence of glucose | E. coli | 5 |

In regard to the first two promoters listed in Table 2, promoters induced by high temperatures are problematic: since high temperatures can be harmful to the host cell culture; since it is often impractical to generate an even temperature spike throughout the large-scale, commercial fermentation volume; and since it is preferred to operate commercial fermentation equipment at lower temperatures than required for such induction. The other four suggested promoters listed in Table 2 have, to the inventors' knowledge, not been demonstrated to function well in large-scale fermentation conditions; also, the alkyl- and halo-toluene inducers of the Pu promoter are significantly toxic to biological systems.

Thus, there remains a need for promoters that are useful for commercial fermentation production systems, activated by low-cost, low-toxicity chemical inducers, and tightly controlled.

In addition, in order to facilitate control of gene expression for production of proteins (and other expression products) and chemicals (processed by action of the expression products and/or the host cell) in a common fermentation platform using one prokaryotic organism, it is desirable to have a library of expression cassettes. These cassettes would each contain one or more of a variety of promoters that are of differing strengths, and/or induced under different growth conditions or by different chemicals. These expression cassettes would then be linked to various genes of interest to achieve total control of those genes under fermentation friendly conditions. The identification and optimization of a wide variety of growth-phase-dependent or chemically-inducible promoters is thus essential for control of (trans)gene expression during fermentation in such a fermentation platform.

Moreover, the construction of genetic circuits in which activation or induction of a first gene or operon leads to repression or activation of one or more subsequent genes or operons has been suggested as a means for very fine control of gene expression. Both linear (e.g., serial and cascade) and circular (e.g., daisy-chain) genetic circuits have been created. See, e.g., U.S. Patent Pub. No. 20010016354 A1 of Cebolla Ramirez et al. These genetic circuits require a number of different promoters in order to function, and, in commercial fermentation, genetic circuits would need to rely upon promoters that are effective in commercial fermentation conditions. Thus, there is a need in the field of genetic circuits for a greater variety of promoters useful in commercial fermentation.

As noted above, promoters for use in commercial fermentation systems should be tightly regulated so that expression occurs only upon induction, preferably effected late in the fermentation run. The chemicals used to induce the promoters must be low cost, low-toxicity to the host bacterium and other organisms, and must tightly regulate gene expression. In light of the above discussion, there is a need in the art for novel promoters that are tightly regulated and are induced at low cost using low-toxicity inducers.

SUMMARY OF THE INVENTION

The present invention provides novel promoters that are useful for gene expression in commercial fermentation. In a more specific aspect, the invention provides benzoate-inducible promoters, anthranilate-inducible promoters, and tandem promoters that may be employed in bacterial commercial fermentation systems.

The present invention provides:

isolated and/or recombinant benzoate promoter nucleic acids comprising the −35 region of the *Pseudomonas fluorescens* native benzoate promoter attached upstream of the −10 region thereof, via a 15-20 nucleotide linker; and to the operative promoter nucleic acid segment(s) found in SEQ ID NO:1;

mutant and closely related promoter nucleic acids whose nucleotide sequences are at least 90% homologous to such promoter nucleic acids;

such promoter nucleic acids further comprising a benzoate promoter activator protein (BenR) binding site; and such promoter nucleic acids further comprising a benzoate promoter activator protein coding sequence, and where such activator protein coding sequences encode a benzoate promoter activator protein having an amino acid sequence at least 90% homologous to any one of the native, mutant, and/or truncated activator protein amino acids sequences presented in SEQ ID NO:2.

The present invention also provides:

isolated and/or recombinant anthranilate promoter nucleic acids comprising the −35 region of the *Pseudomonas fluorescens* native anthranilate promoter attached upstream of the −10 region thereof, via a 15-20 nucleotide linker; and to the operative promoter nucleic acid segment(s) found in SEQ ID NO:7;

mutant and closely related promoter nucleic acids whose nucleotide sequences are at least 90% homologous to such promoter nucleic acids;

such promoter nucleic acids further comprising an anthranilate promoter activator protein (AntR) binding site; and such promoter nucleic acids further comprising a anthranilate promoter activator protein coding sequence, and where such activator protein coding sequences encode an anthranilate promoter activator protein having an amino acid sequence at least 90% homologous to any one of the native, mutant, and/or truncated activator protein amino acids sequences presented in SEQ ID NO:9.

The present invention also provides:

tandem promoters comprising a non-catabolite-repressed promoter attached (i.e. covalently attached) to and upstream of a natively catabolite-repressed promoter, either directly or by means of an inter-promoter polynucleotide linker, in which the catabolite repression of the latter promoter is overcome and/or a different improved promoter property is exhibited;

tandem promoters prepared by a process comprising covalently attaching a prokaryotic non-catabolite-repressed promoter to and upstream of a prokaryotic natively catabolite-repressed promoter, either directly or by means of an inter-promoter polynucleotide linker;

such tandem promoters wherein the inter-promoter polynucleotide linker is about 100 or less than 100 nucleotides long;

such tandem promoters in which the component non-catabolite-repressed and natively catabolite-repressed promoters are prokaryotic promoters, or bacterial promoters; and to tandem promoters in which the component promoters are obtained from the same of different species of the Pseudomonads and closely related bacteria, and/or of the genus *Pseudomonas*, and/or from *Pseudomonas fluorescens*; and to tandem promoters in which the component promoters are obtained from gene(s) or operon(s) encoding alternative carbon source utilization enzyme(s) or pathway(s); and to tandem promoters in which the non-catabolite-repressed promoter is obtained from an operon encoding an anthranilate degradation pathway and the natively catabolite-repressed promoter is obtained from an operon encoding a benzoate degradation pathway, and/or in which the anthranilate promoter and benzoate promoter are selected from among those summarized in the above paragraphs; and the operative tandem promoter(s) found in, or constructed from the component promoters shown in, SEQ D NO:13.

The present invention also provides:

altered promoters prepared by a process comprising obtaining at least one polynucleotide having a base sequence at least 90% identical to and heterologous to the base sequence of any one of the claimed promoters or the sequence of any one of at least bases 1275-1307 of SEQ ID NO:1, at least bases 1239-1274 of SEQ ID NO:7, and at least bases 1329-1509 of SEQ ID NO:13; screening the polynucleotide(s) for the ability to direct transcription in a prokaryotic host cell, and optionally for at least one promoter property; and identifying, based on the results, at least one promoter, optionally having at least one improved property; and improved promoters prepared by a process of: utilizing a promoter polynucleotide, having a base sequence of any one of the claimed promoters or the sequence of any one of at least bases 1275-1307 of SEQ ID NO:1, at least bases 1239-1274 of SEQ ID NO:7, and at least bases 1329-1509 of SEQ ID NO:13, as a hybridization probe for sequence-altered polynucleotide(s) at least 90% homologous thereto, or of performing mutagenesis and/or recombination upon said promoter polynucleotide to generate said sequence-altered polynucleotide(s), or of utilizing an information string representing the base sequence of the promoter polynucleotide to perform a search for a heterologous string at least 90% homologous thereto and providing a sequence-altered polynucleotide having the base sequence represented by said heterologous string; or of modifying such an information string into such a heterologous string and utilizing said modified string to identify an information string identical thereto and then providing a sequence-altered polynucleotide having the base sequence represented by said information string; followed by screening the sequence-altered polynucleotide(s) for the ability to direct transcription in a prokaryotic host cell, and for at least one promoter property; and identifying, based on the results, at least one promoter having at least one improved property.

The present invention also provides:

isolated nucleic acid molecules comprising a nucleic acid sequence whose complement hybridizes under stringent hybridization and wash conditions to a nucleobase polymer molecule having a base sequence of any one of the claimed promoters or of any one of at least bases 1275-13b7 of SEQ ID NO:1, at least bases 1239-1274 of SEQ ID NO:7, and at least bases 1329-1509 of SEQ ID NO:13, wherein said isolated nucleic acid molecule can function as a promoter in a prokaryotic cell; and isolated nucleobase polymer molecules having the base sequence of a prokaryotic promoter polynucleotide molecule having a base sequence at least 90% identical to the base sequence of any one of the claimed promoters or of any one of at least bases 1275-1307 of SEQ ID NO:1, at least bases 1239-1274 of SEQ ID NO:7, and at least bases 1329-1509 of SEQ ID NO:13

The present invention also provides:

recombinant nucleic acid molecules that can function as expression construct(s) in a prokaryotic cell, comprising a promoter containing a base sequence at least 90% identical to the base sequence of any one of the claimed promoters or of any one of at least bases 1275-1307 of SEQ ID NO:1, at least bases 1239-1274 of SEQ ID NO:7, and at least bases 1329-1509 of SEQ ID NO:13; such recombinant expression constructs comprising an mRNA-encoding sequence; such recombinant expression constructs wherein the expression construct is a vector; such recombinant expression constructs wherein the vector is a plasmid; genetically engineered prokaryotic host cells containing any such a recombinant expression construct, and preferably also at least one, and more preferably more than one, copy of a gene encoding the relevant activator protein for the promoter of said recombinant expression construct (and where said gene is expressed in the host cell); expression systems comprising such a genetically engineered prokaryotic host cell that preferably contains at least one, and more preferably more than one, copy of a gene encoding the relevant activator protein for the promoter of said recombinant expression construct (and where said gene is expressed in the host cell); and such expression systems wherein the promoter is a benzoate-inducible promoter and the activator protein has an amino acid sequence of either any one of residues 1-335 or 21-335 of SEQ ID NO:2, optionally containing Asn152; and such expression systems wherein the promoter is an anthranilate-inducible promoter and the activator protein has an amino acid sequence of either residues 1-330 of SEQ ID NO:9or residues 1-330 of SEQ ID NO:9 containing Ala268.

The present invention also provides:

a process for preparing a transcription product comprising growing such a genetically engineered prokaryotic host cell, and inducing the recombinant expression construct therein, thereby expressing the transcription product encoded thereby; and a process for preparing a polypeptide comprising expressing an mRNA transcription product, by use of such a process for preparing a transcription product, and further permitting the host cell to translate the mRNA into the polypeptide encoded thereby.

The present invention also provides transcriptional activator proteins operative in prokaryotic cells. These include a transcriptional activator protein having an amino acid sequence at least 90% homologous to that of any one of residues 1-335 of SEQ ID NO:2, residues 1-335 of SEQ ID NO:2containing Asn152, residues 21-335 of SEQ ID NO:2, and residues 21-335 of SEQ ID NO:2 containing Asn152; and a transcriptional activator protein having an amino acid sequence at least 90% homologous to that of any one of residues 1-330 of SEQ ID NO:9, or of residues 1-330 of SEQ ID NO:9 containing Ala268. The present invention also provides polynucleotide molecules containing a base sequence encoding such transcriptional activator proteins.

BRIEF DESCRIPTION OF DRAWINGS

FIG. 5 presents a comparison of the nucleotide sequences of the Pben509 (nucleotides c994-c1502 of SEQ ID NO:1) and Pben278 (nucleotides g1228-c1502 of SEQ ID NO:1) benzoate -inducible promoters. The TTA translational stop site of the upstream ORF, and the putative–35 region (TTGACG, nucleotides 1275 through 1280 of SEQ: ID NO:1), –10 region (TACGGT, nucleotides 1296 through 1301 of SEQ ID NO:1), and "C" transcription start site are underlined. The "C" double-underlined in the Pben278 sequence indicates a mutation in Pben278, which differs from Pben509 and the genomic sequence; this mutation was introduced during PCR amplification.

FIG. 7 presents a comparison of the nucleotide sequences of four Pant promoters: Pant+AntR (a1-cl395 of SEQ ID NO:13), Pant713 (nucleotides c592-c1304 of SEQ ID NO:7), Pant705 (nucleotides c592-g1288 of SEQ ID NO:7), and Pant311 (nucleotides c994-c1304 of SEQ ID NO:7). The double-underlined nucleotide triplets (TCA and CAT)respectively indicate the stop and start codons of the AntR ORF, which is encoded by the strand complementary to that shown. The lone double-underlined "A" indicates a mutation from the genomic sequence, confirmed on both strands, which lies within the AntR coding sequence; this change results in an expressed change from alanine to serine in the AntR protein. The putative –35 region (ATAGCC, nucleotides 1238 through 1243 of SEQ ID NO:7), –10 region (CTTAAT, nucleotides 1263 through 1267 of SEQ ID NO:7), and transcription start site ("A"), and the complement of the putative ribosome binding site (GGAGG, nucleotides 1817 through 1821 of SEQ ID NO:7) are all underlined.

FIG. 9 presents bar charts showing induction of a Pant-Pben tandem promoter construct, and induction of component promoter constructs. In all constructs, the promoter was fused to a β-galactosidase-encoding sequence. Induction of a Pant-Pben tandem promoter construct (pDOW1057) with either benzoate or anthranilate is presented in comparison to that of constructs containing one of the component promoters: a Pben promoter construct (pDOW1028), containing Pben278, and a Pant promoter construct (pDOW1035), containing the antR/Pant.

FIG. 11 presents a comparison of the nucleotide sequences of Pben509 (nucleotides c994-c1502 of SEQ ID NO:1) and two improved mutants thereof created by means of error prone PCR: mutant 2d3 (nucleotides c994-c1502 of SEQ ID NO:1 with a1106→t1106) and mutant 21b5 (nucleotides c994-c1502 of SEQ ID NO:1 with c1223→t1223 and g1302→a1302). The TTA translational stop site of the upstream ORF, and the putative –35 region (TTGACG, nucleotides 1275 through 1280 of SEQ ID NO:1), –10 region (TACGGT, nucleotides 1296 through 1301 of SEQ ID NO:1), and "C" transcription start site are underlined. Mutations are shown double-underlined.

FIG. 13 presents graphs demonstrating improved anthranilate-induced expression from a tandem promoter construct (pDOW1057) in an antA knockout host created by means of a single crossover knockout of the antA gene in the host cell (*Pseudomonas fluorescens*). Results are shown for 20 L fermentations induced at a target level of about 5 mM sodium anthranilate and followed over a 48 hour time course post-induction. No anthranilate feed was required.

DETAILED DESCRIPTION OF PREFERRED EMBODIMENTS

Figure 1:
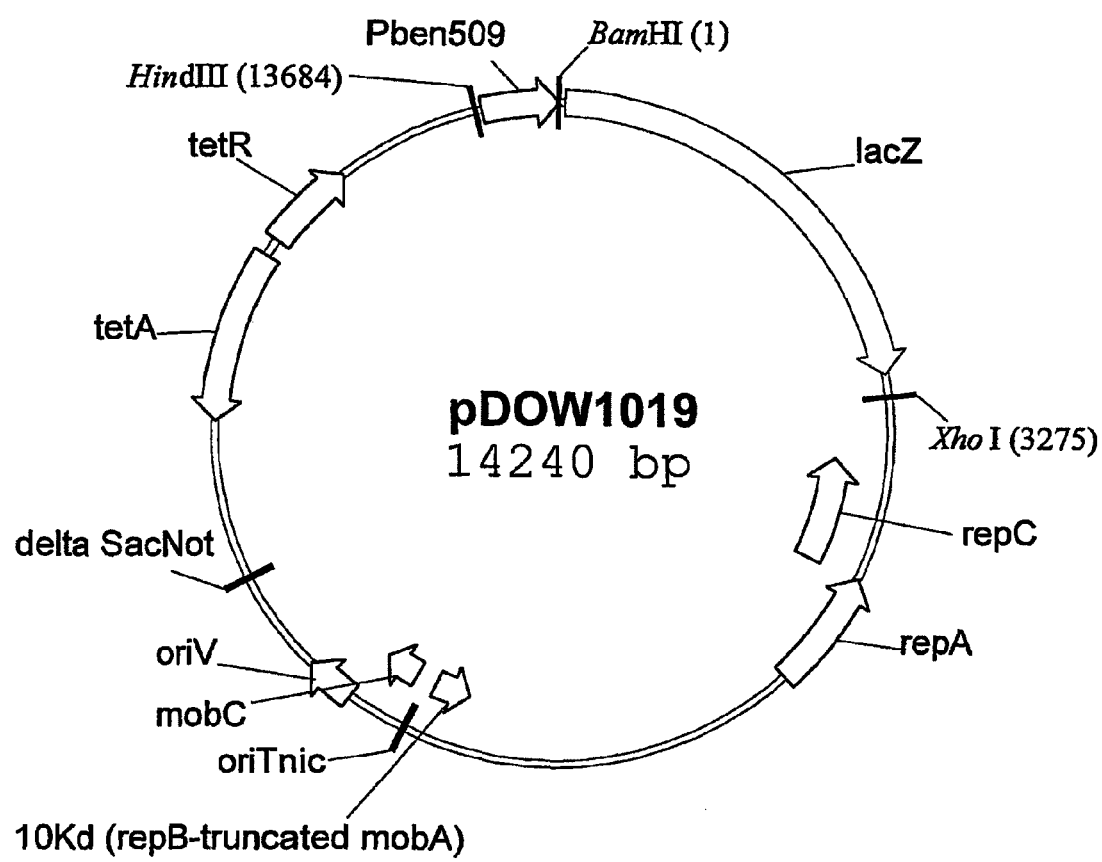
FIG. 1 presents a plasmid map of pDOW1019, a vector comprising Pben509, a benzoate-inducible promoter according to the present invention.
Figure 2:
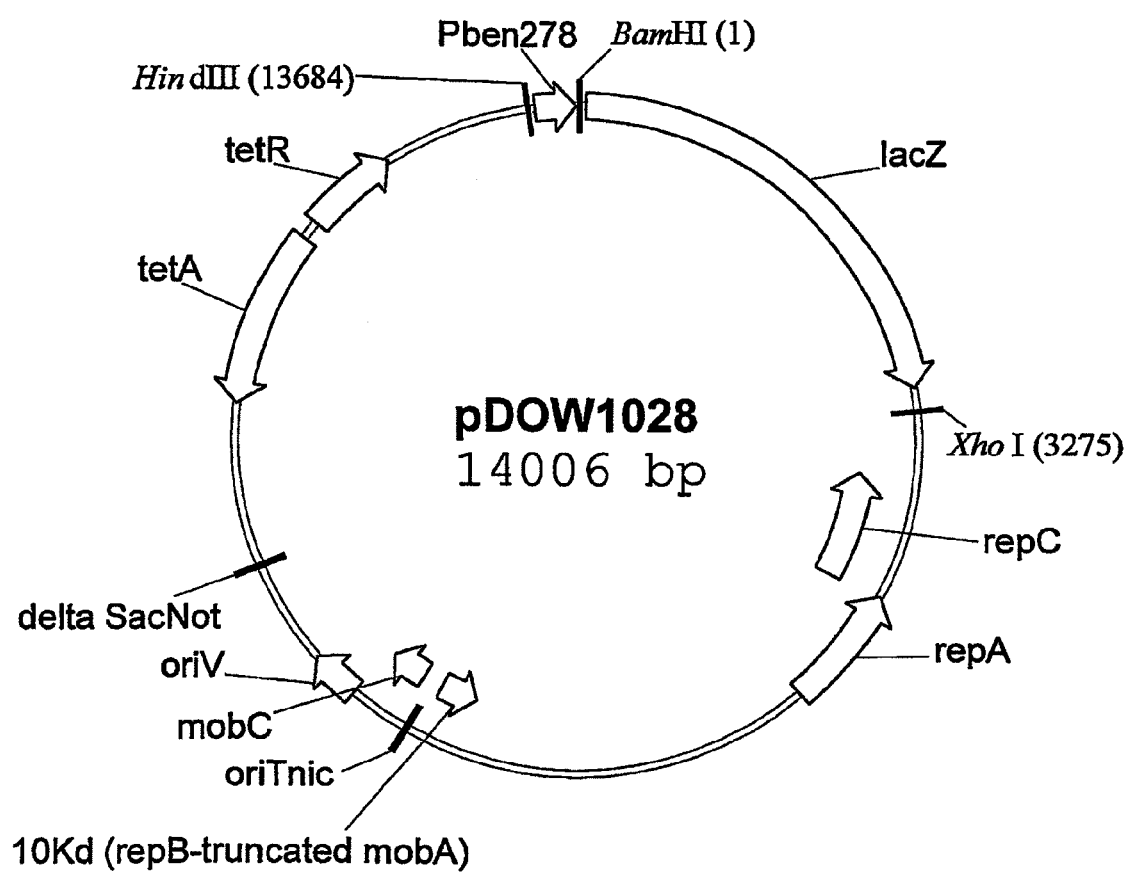
FIG. 2 presents a plasmid map of pDOW1028, a vector comprising Pben278, a benzoate-inducible promoter according to the present invention.
Figure 3:
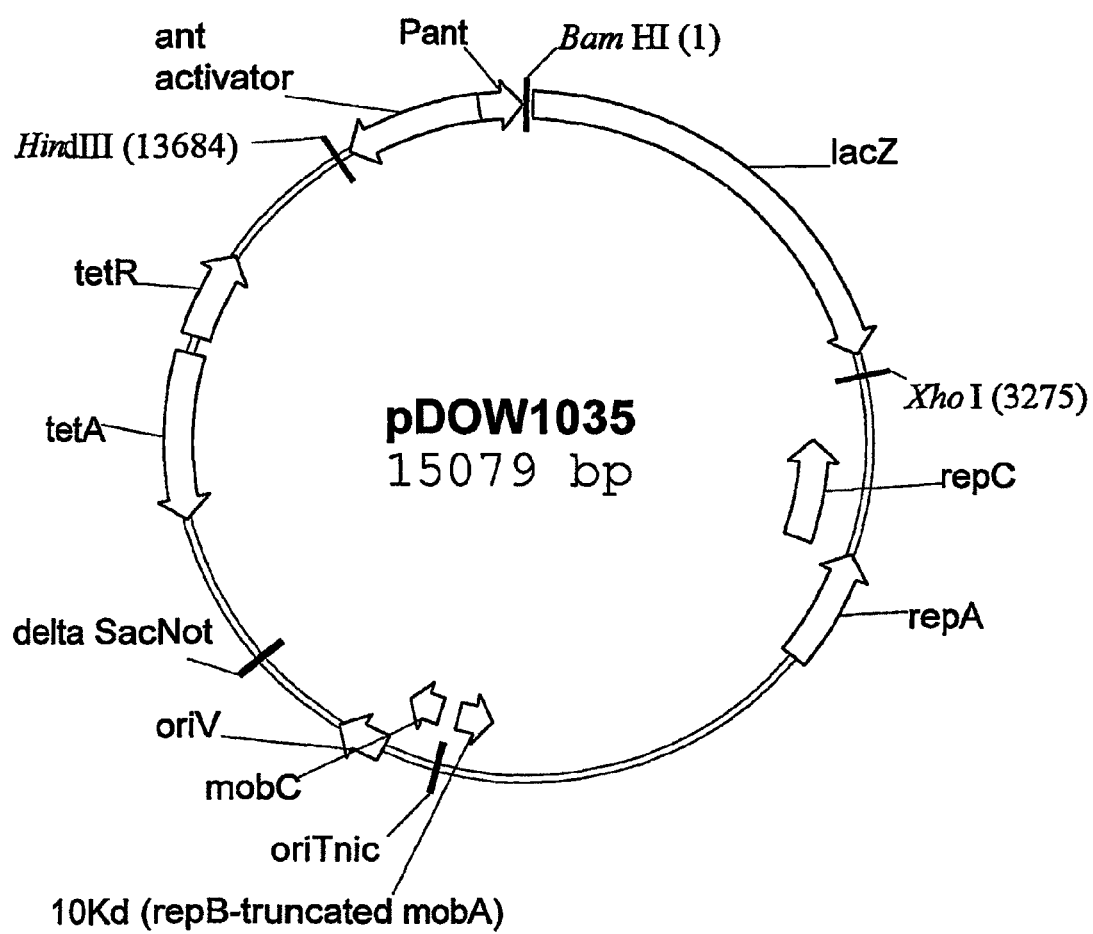
FIG. 3 presents a plasmid map of pDOW1035, a vector comprising an anthranilate-inducible promoter according to the present invention, including the coding sequence of the activator protein therefor.
Figure 4:
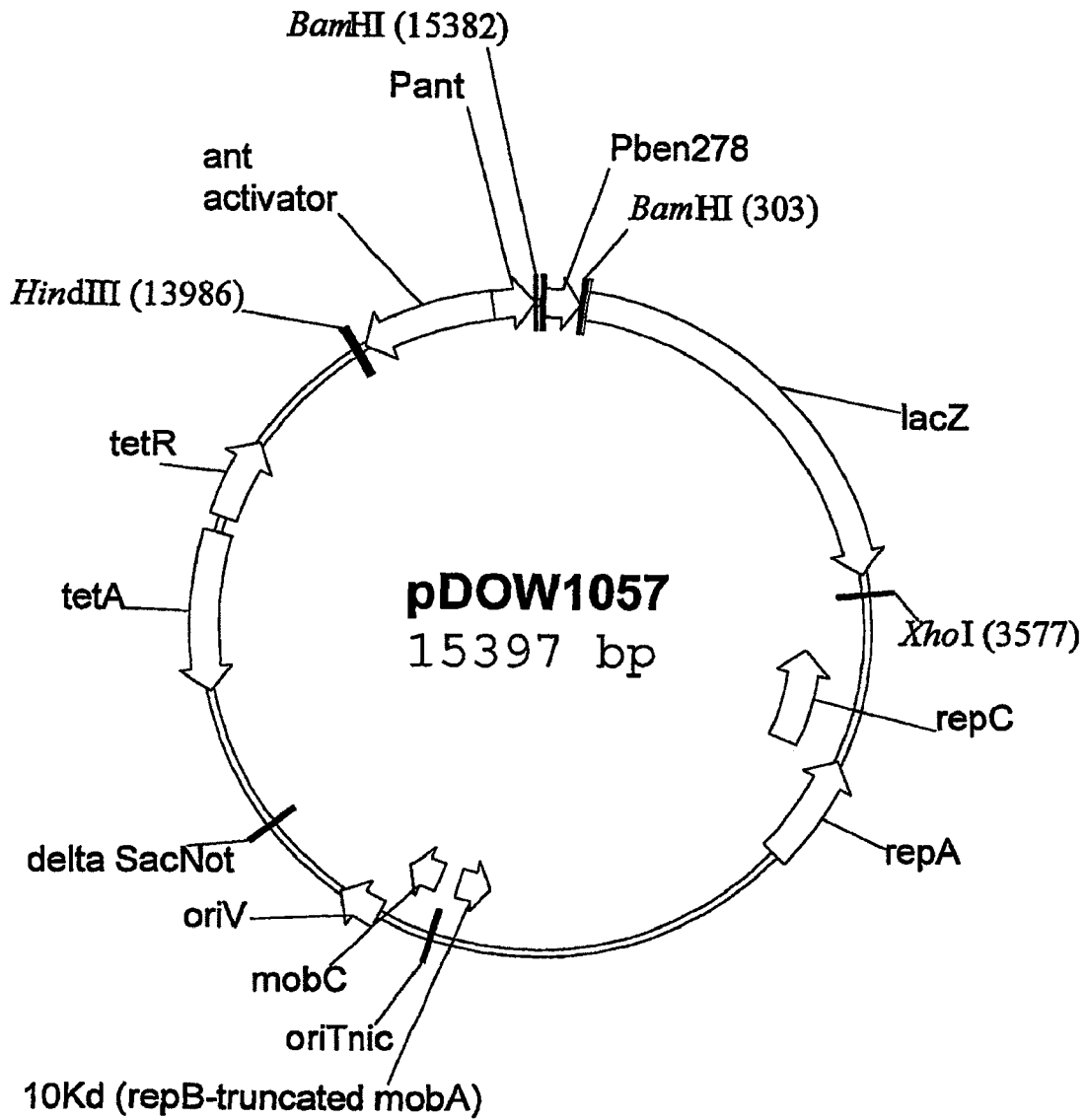
FIG. 4 presents a plasmid map of pDOW1057, a vector comprising an anthranilate-benzoate tandem promoter according to the present invention.

The present invention provides commercially useful benzoate-inducible promoters, anthranilate-inducible promoters, and tandem promoters that may be employed in bacterial commercial fermentation systems. Preferred bacterial host cells for use in such systems include Pseudomonads and closely related bacteria The chemical inducers of these promoters include benzoic and anthranilc acids, their effective chemical analogs, and biologically acceptable salts thereof.

Benzoic and anthranilic acids and biologically acceptable salts, preferably sodium or potassium salts, thereof, are inexpensive chemicals with low toxicity that can be utilized as (alternative) carbon sources by bacterial host cells, including Pseudomonads and closely related bacteria For example, these chemical inducers are available on the market at less than about US$0.15 per gram (versus about US$18 or US$36 per gram for IPTG).

The present inventors have isolated, sequenced, and characterized the native promoters responsible for expression of the *P. fluorescens* benzoate (benABCD) degradative genes, which may be induced with benzoate in the absence of glucose, and of the *P. fluorescens* (antABC) degradative genes, which may be induced with anthranilate. (The expression products of these operons are catabolic pathway enzymes responsible for degradation of benzoate and anthranilate, respectively, in *Pseudomonas fluorescens* biotype A.) These promoters have been found capable of inducing expression of exogenous genes about 250-fold, for the benzoate promoter, and about 25- to about 35-fold, for the anthranilate promoter, when induced with 5 mM sodium benzoate and 5 mM sodium anthranilate, respectively. The present inventors have found these promoters to be sufficiently inducible for use in commercial fermentation systems to produce proteins and chemicals in bacterial host cells, including Pseudomonads and closely related bacteria In addition, the present inventors have created tandem promoter constructs in which a non-catabolite-repressed promoter is linked upstream of a natively catabolite-repressed promoter, thereby surprisingly overcoming the catabolite repression of the latter promoter and/or thereby exhibiting a different improved property (e.g., increased strength of induction or increased tightness of regulation). At least one example of a tandem promoter construct has been described for expression of foreign genes [6]. However, this example is a tandem arrangement of two copies of the same promoter, Plac, and the reference presents no evidence to suggest that the tandem Plac-Plac promoter has advantages over a single Plac promoter. Likewise, dual promoter constructs are known, e.g., for use in shuttle vectors, in which two promoters operative in different species or genera are both operably attached to the same gene so that the gene can be expressed in either of the two different species or genera.

In contrast to these tandem and dual promoter constructs, the present creation of tandem promoter constructs, in which two non-identical promoters are placed in tandem arrangement, has surprisingly been found to retain advantageous features of both promoters.

For example, the tandem arrangement of the anthranilate promoter, Pant, and the benzoate promoter, Pben, has resulted in formation of a tandem promoter that, when induced with anthranilate under fermentation conditions, exhibits both freedom from catabolite repression (a desirable feature of Pant, not shared by Pben) and improved strength of induction (a desirable feature of Pben, not shared by Pant). Thus, the tandem promoters of the present invention permit retention of desirable properties of the individual promoter elements, so that the resulting tandem promoter can exhibit improved properties: e.g., increased strength of induction, or increased tightness of regulation (i.e. transcription only when contacted with the relevant inducer of the promoter's activator or repressor protein); and/or lack of catabolite repression.

GLOSSARY

A### (Absorption)

As used herein in regard to analytical detection, terms such as "A450" mean "absorption at a wavelength of 450 nm."

A and An (Indefinite Articles)

As used herein and in the appended claims, the singular forms "a", "an", and "the" include both singular and plural referents unless the context clearly dictates otherwise. Thus, for example, reference to "a host cell" literally defines both those embodiments employing only a single host cell, those employing a plurality of host cells of a single type, and those employing a plurality of host cells of a plurality of types.

**\* (Asterisk)**

As used herein in regard to calculations, the "*" symbol (asterisk) indicates the mathematical multiplication function.

BCIP

5-Bromo4-chloro-3-indolyl phosphate, e.g., a divalent salt thereof, such as a disodium salt. This is used in conjunction with a, e.g., tetrazolium salt, such as: a halide salt of Nitroblue Tetrazolium (NEBT), e.g., bis-[2-(4-yl-2-methoxyphenyl)3-(4-nitrophenyl)-5-phenyl-tetrazolium chloride]; or of Iodo-Nitro-Tetrazolium (INT), also called Iodoblue Tetrazolium, e.g., 2-(4-iodophenyl)-3-(4-nitrophenyl)-5-phenyl tetrazolium chloride.

Comprising

As used herein, the term "comprising" means that the subject contains the elements enumerated following the term "comprising" as well as any other elements not so enumerated. In this, the term "comprising" is to be construed as a broad and open-ended term; thus, a claim to a subject "comprising" enumerated elements is to be construed inclusively, i.e. construed as not limited to the enumerated elements. Therefore, the term "comprising" can be considered synonymous with terms such as, e.g., "having," "containing," or "including."

The invention, as described herein, is spoken of using the terms "comprising" and "characterized in that." However, words and phrases having narrower meanings than these are also useful as substitutes for these open-ended terms in describing, defining, or claiming the invention more narrowly.

Corresponding

As used herein in reference to a sequence record's "corresponding to" a polynucleotide source, the term "corresponding" means that a given base sequence contained, as an information string, within the sequence record, is present in the form of a physical nucleobase sequence-containing molecule within the polynucleotide source.

ddH$_2$O

As used herein, ddH$_2$O refers to distilled, deionized water purified through a Milli-Q gradient system with Q-GARD purification pack (Miripore, Bedford, Mass.).

dNTPs

Except where otherwise indicated, as used herein in regard to reagents for polynucleotide synthesis reactions, the term "dNTPs" means an equimolar solution of each of the four deoxyribonucleotide triphosphates (dGTP, dCTP, dATP, dTTP). Thus, e.g., reference to 10 mM dNTPs indicates a solution containing 10 mM each of dGTP, dCTP, dATP, and dTTP.

Exogenous and Foreign

The term "exogenous" means "from a source external to" a given cell or molecule. In the present application, as is common use in the art, this term is used interchangeably with the term "foreign," as synonyms. Both of these terms are used herein to indicate that a given object is foreign a given the cell or molecule (e.g., a promoter polynucleotide), i.e. not found in nature in the cell and/or not found in nature with or connected to the molecule.

Heterologous

As used herein, the term "heterologous mean "non-identical" in sequence (not 100% identical in base sequence).

In and On

As used herein in regard to growing organisms by use of a growth medium, the organisms may be said to be grown "in" or "on" the medium. In the expression systems of the present invention, the medium is preferably a gel or liquid medium, more preferably an aqueous gel or liquid medium, and still more preferably an aqueous liquid medium. Thus, in this context, the terms "in" and "on" are used synonymously with one another to indicate growth of the host cells in contact with the medium.

Information String

As used herein, the phrase "information string" means a series of data elements (e.g., bits, bytes, or alphanumeric characters), which series represents the information of a given series of nucleobases.

IPTG

Isopropyl-β-D-1-thiogalactopyranoside.

ONPG

O-Nitrophenyl-β-D-galactopyranoside, also known as 2-Nitrophenyl-β-D-galactopyranoside.

ORF

Open reading frame.

PNPP para-Nitrophenyl phosphate, e.g., a divalent salt thereof, such as a disodium salt. Also referred to as 4-nitrophenyl phosphate.

Polynucleotide Length

As used herein, the term "nucleotides" is used to describe the length of polynucleotides. However, in this context, the terminology is meant to refer both to length in nucleotides per se in regard to single stranded polynucleotides, and to length in base pairs in regard to double stranded polynucleotides.

Polynucleotide Source

As used herein, the phrase "polynucleotide source" means any source of a physical embodiment of a nucleic acid containing a given nucleobase sequence, such as a nucleic acid sample, clone, or native cell containing such a polynucleotide molecule.

Promoter Activator Protein Terminology

The native activator of a given promoter is designated with an "R" as, e.g., BenR, AntR for the native activators of the Pben and Pant promoters, respectively.

Promoter Terminology

"Pant": Promoter for the anthranilate operon of *P. fluorescens*.

"Pben": Promoter for the benzoate operon of *P. fluorescens*.

"Plac": Promoter for the lactose operon of *E. coli*.

"Ptandem" and "tandem promoter": a tandem arrangement of promoters in which a non-catabolite-repressed promoter is attached to and upstream of, by means of a sequence of 0 to about 100 nucleotides, a catabolite-repressed promoter. This is exemplified herein by Pant-Pben tandem promoter constructs.

"Promoter": a polynucleotide comprising at least 25 nucleotides, more commonly about 30 nucleotides, containing a prokaryotic "−35 region through −10 region." Preferably, this "−35 region through −10 region" is a "−35 region through −10 region" obtained from a single gene, or a combination of a −35 region and a −10 region obtained from cognate genes, the gene(s) being obtained from at least one prokaryote, more preferably at least one organism of the "Pseudomonads and closely related species." Preferably, the "−35 region through −10 region" is a σ70 "−35 region through −10 region," and the "−35 region" and the "−10 region" in the combination are, respectively, a σ70 −35 region and a σ70 −10 region.

The −35 region is linked upstream of the −10 region by an intra-promoter polynucleotide of preferably about 15 to about 20 nucleotides. More preferably, a promoter according to the present invention comprises about 35 nucleotides, which contains, in addition to the "−35 region through −10 region," a segment of about 5 to about 10 immediate downstream nucleotides, more preferably 6 to 7 immediate downstream nucleotides, terminating in a transcription start site nucleotide. In a preferred embodiment, this segment is obtained from the same gene as provides at least one of the −35 or −10 region. In a particularly preferred embodiment, the promoter will also contain an immediate upstream region of about 20 to about 250, more preferably about 40 to about 150, nucleotides comprising a promoter activator protein binding site, preferably an AraC/XylS-class binding site. In a preferred embodiment, the binding site region is obtained from the same gene as provides at least one of the −35 or −10 region.

As used herein, the term "−35 region" or "minus 35 region", indicates a 5-6 nucleotide sequence beginning approximately 35 nucleotides upstream (i.e. in a 5' direction from) a transcription start site, the transcription start site being numbered as "+1."

Likewise, the term "−10 region" or "minus 10" region" indicates a 5-6 nucleotide sequence beginning approximately 10 nucleotides upstream (i.e. in a 5' direction from) a transcription start site, the transcription start site being numbered as "+1."

RNA Terms

As used herein, the following RNA terms have the definitions recited below.
  aRNA: anti-sense RNA
  cRNA: cytoplasmic RNA
  gRNA: guide RNA (for editing mitochondrial pre-mRNAs)
  hnRNA: heteronuclear RNA
  mRNA: messenger RNA
  miRNA: microRNA (for regulating mRNA expression)
  mtRNA: mitochondrial RNA
  nRNA: nuclear RNA
  ncRNA: non-coding RNA
  pRNA: packaging RNA (for virus and phage particle assembly)
  rRNA: ribosomal RNA
  satRNA: satellite RNA
  scRNA: small cytoplasmic RNA
  siRNA: small interfering RNA
  snRNA: small nuclear RNA
  snoRNA: small nucleolar RNA
  srpRNA: signal recognition particle RNA
  stRNA: small temporal RNA (a subgroup of miRNA)
  tRNA: transfer RNA
  tmRNA: transfer-messenger-like RNA (for marking, for subsequent degradation, nascent polypeptides in stalled ribosomes)
  vRNA: viral (and/or phage) RNA Searching As used herein in regard to seeking for information, the term "search" means performing (by manual, visual, or automated means) one or more comparisons between a known information string and other information strings in order to identify an identical or non-identical information string.

Sequence Record

As used herein, the phrase "sequence record" means a stored embodiment of one or more information strings, such as a computer readable record or a paper record.

−10 Variant Promoter Designations

"−10 con": indicates a variant promoter in which the native −10 region has been substituted with the consensus −10 region sequence 'tataat.'

"−10 ben": indicates a variant promoter in which the native −10 region has been substituted with the −10 region from *P. fluorescens* Pben 'tacggt.'

"−10 benAc": indicates a variant promoter in which the native −10 region has been substituted with the −10 region from *Acinetobacter* Pben 'taaggt.'

"−10 wt": indicates truncated native promoter retaining the wild-type −10 sequence.

∼ (Tilde)

The ∼ symbol (the tilde) is used herein to indicate "about".

× (Times)

The × symbol (the times symbol), as used herein in regard to the concentration of a solution, means, e.g., that a 5× preparation is five times as concentrated as a 1× preparation, for the same solution composition (ie. for the same relative amounts of all components therein).

Tris

The term "Tris" as used herein means Tris (hydroxymethyl) aminomethane (available from Fisher Scientific, Pittsburgh, Pa.).

X-gal 5-bromo4-chloro-3-indolyl-β-D-galactopyranoside

General Materials & Methods

Unless otherwise noted, standard techniques, vectors, control sequence elements, and other expression system elements known in the field of molecular biology are used for nucleic acid manipulation, transformation, and expression. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY); Berger & Kimmel, *Methods in Enzymology* 152: Guide to Molecular Cloning Techniques (1987) (Academic Press); and Bukhari et al. (eds.), *DNA Insertion Elements, Plasmids and Episomes* (1977) (Cold Spring Harbor Laboratory Press, NY).

The promoters of the present invention include the benzoate promoter from *Pseudomonas fluorescens*, the anthranilate promoter from *Pseudomonas fluorescens*, and their derivatives. The promoters of the present invention also include tandem promoters having a non-catabolite-repressed promoter linked upstream of a natively catabolite-repressed promoter, in which the catabolite repression of the latter promoter is overcome and/or a different improved promoter property is exhibited.

The promoters of the present invention are typically in the form of DNA when in use in an expression system. However, the nucleobase sequence of the promoters may be present in the form of DNA, RNA, or any nucleic acid analog known in the art, e.g., peptide nucleic acid (PNA).

Benzoate Promoters

In a preferred embodiment, a benzoate promoter of the present invention is the *Pseudomonas fluorescens* native benzoate promoter or an improved mutant thereof. The present inventors have found this promoter to be inducible with benzoic acid, benzoic acid analogs (e.g., m-toluic acid), and biologically acceptable salts thereof (e.g., sodium benzoate).

In a preferred embodiment, a benzoate promoter of the present invention comprises the −35 region of the *Pseudomonas fluorescens* native benzoate promoter attached upstream of the −10 region of this native promoter, via a 15-20 nucleotide linker. In a preferred embodiment, the linker is 15 nucleotides long.

In a preferred embodiment, a benzoate promoter of the present invention comprises nucleotides 1275-1280 of SEQ ID NO:1 attached upstream of nucleotides 1296-1301 of SEQ ID NO:1, via a 15-20 nucleotide linker. In a preferred embodiment, the linker is 15 nucleotides long. In a particularly preferred embodiment, the linker is nucleotides 1281-1295 of SEQ ID NO:1, a benzoate promoter of this preferred embodiment thereby comprising nucleotides 1275-1301 of SEQ ID NO:1. In a preferred embodiment, a benzoate promoter of the present invention comprises nucleotides 1275-1301 of SEQ ID NO:1 attached immediately upstream of a spacer segment of about 6 nucleotides, preferably of 6 nucleotides, in length, and terminating with a nucleotide that functions as a transcription start site. In a preferred embodiment, the spacer segment is nucleotides 1302-1307 of SEQ ID NO:1, a benzoate promoter of this preferred embodiment thereby comprising nucleotides 1275-1307 of SEQ ID NO:1.

In a preferred embodiment, a benzoate promoter of the present invention comprises both a "−35 to −10 region" and a benzoate promoter activator (or repressor) protein binding site, preferably an activator protein binding site. In a preferred embodiment, a benzoate promoter of the present invention comprises nucleotides 1275-1301 of SEQ ID NO:1 attached immediately downstream of a spacer region of about 50 nucleotides in length. In a preferred embodiment, a benzoate promoter of the present invention comprises nucleotides 1275-1301 of SEQ ID NO:1 attached immediately downstream of a spacer region of about 45 nucleotides in length. In a preferred embodiment, the spacer region has the sequence of the region shown in SEQ ID NO:1, beginning about 50 nucleotides upstream of nucleotide 1275 and ending with nucleotide 1274. In a preferred embodiment, the spacer region has the sequence of the region shown in SEQ ID NO:1, beginning about 45 nucleotides upstream of nucleotide 1275 and ending with nucleotide 1274. In a preferred embodiment, the spacer region has the sequence of nucleotides 1228-1274 of SEQ ID NO:1, a benzoate pronmoter of this preferred embodiment thereby comprising the sequence of nucleotides 1228-1301.

In a preferred embodiment, a benzoate promoter of the present invention comprises nucleotides 1275-1301 of SEQ ID NO:1 attached immediately upstream of said spacer segment and attached immediately downstream of said spacer region. In a preferred embodiment, a benzoate promoter of the present invention comprises nucleotides 1228-1307 of SEQ ID NO:1.

In a preferred embodiment, in expression systems in which a benzoate promoter according to the present invention is used, the host cell will also contain and express at least one nucleic acid encoding a benzoate promoter activator protein. Even more preferred is the use therein of multiple expressed copies of such a Pben activator protein-encoding nucleic acid. In a preferred embodiment, the Pben activator protein will have an amino acid sequence of SEQ ID NO:2 or the residue 152 (Asn) variant thereof, or an amino acid sequence of residues 21-335 of SEQ ID NO:2 or the residue 152 (Asn) variant thereof. In a preferred embodiment, the nucleic acid encoding the Pben activator protein will contain the sequence of bases 285-1229 of SEQ ID NO:1 or the base 679 mutant variant thereof, or the sequence of bases 225-1229 of SEQ ID NO:1 or the base 679 mutant variant thereof; or the complement thereof of any of these; or the RNA equivalent of any of these.

Anthranilate Promoters

In a preferred embodiment, an anthranilate promoter of the present invention is the *Pseudomonas fluorescens* native anthranilate promoter or an improved mutant thereof. The present inventors have found this promoter to be inducible with anthranilic acid, anthranilic acid analogs (e.g., haloanthranilic acids), and biologically acceptable salts thereof (e.g., sodium anthranilate); and with o-toluate (o-toluate has been found to induce this promoter as well as does anthranilate).

In a preferred embodiment, an anthranilate promoter of the present invention comprises the −35 region of the *Pseudomonas fluorescens* native anthranilate promoter attached upstream of the −10 region of this native promoter, via a 15-20 nucleotide linker, more preferably a 16-19 nucleotide linker. In a preferred embodiment, the linker is 19 nucleotides long.

In a preferred embodiment, an anthranilate promoter of the present invention comprises nucleotides 1239-1244 of SEQ ID NO:7 attached upstream of nucleotides 1264-1268 of SEQ ID NO:7, via a 15-20 nucleotide linker. In a preferred embodiment, the linker is 19 nucleotides long. In a particularly preferred embodiment, the linker is nucleotides 1245-1263 of SEQ ID NO:7, an anthranilate promoter of this preferred embodiment thereby comprising nucleotides 1239-1268 of SEQ ID NO:7. In a preferred embodiment, an anthranilate promoter of the present invention comprises nucleotides 1239-1268 of SEQ ID NO:7 attached immediately upstream of a spacer segment of about 6 nucleotides, preferably of 6 nucleotides, in length, and terminating with a nucleotide that functions as a transcription start site. In a preferred embodiment, the spacer segment is nucleotides 1269-1274 of SEQ ID NO:7, an anthranilate promoter of this preferred embodiment thereby comprising nucleotides 1239-1274 of SEQ ID NO:7.

In a preferred embodiment, an anthranilate promoter of the present invention comprises both a "−35 to −10 region" and an anthranilate promoter activator (or repressor) protein binding site, preferably an activator protein binding site. In a preferred embodiment, an anthranilate promoter of the present invention comprises nucleotides 1239-1268 of SEQ ID NO:7 attached immediately downstream of a spacer region of about 250 nucleotides in length. In a preferred embodiment, an anthranilate promoter of the present invention comprises nucleotides 1239-1268 of SEQ ID NO:7 attached immediately downstream of a spacer region of about 200 nucleotides in length. In a preferred embodiment, an anthranilate promoter of the present invention comprises nucleotides 1239-1268 of SEQ ID NO:7 attached immediately downstream of a spacer region of about 150 nucleotides in length. In a preferred embodiment, an anthranilate promoter of the present invention comprises nucleotides 1239-1268 of SEQ ID NO:7 attached immediately downstream of a spacer region of about 120 nucleotides in length. In a preferred embodiment, an anthranilate promoter of the present invention comprises nucleotides 1239-1268 of SEQ ID NO:7 attached immediately downstream of a spacer region of about 110 nucleotides in length. In a preferred embodiment, an anthranilate promoter of the present invention comprises nucleotides 1239-1268 of SEQ ID NO:7 attached immediately downstream of a spacer region of about 100 nucleotides in length. In a preferred embodiment, an anthranilate promoter of the present invention comprises nucleotides 1239-1268 of SEQ ID NO:7 attached immediately downstream of a spacer region of about 85 nucleotides in length. In a preferred embodiment, an anthranilate promoter of the present invention comprises nucleotides 1239-1268 of SEQ ID NO:7 attached immediately downstream of a spacer region of about 80 nucleotides in length. In a preferred embodiment, an anthranilate promoter of the present invention comprises nucleotides 1239-1268 of SEQ ID NO:7 attached immediately downstream of a spacer region of about 75 nucleotides in length. In a preferred embodiment, an anthranilate promoter of the present invention comprises nucleotides 1239-1268 of SEQ ID NO:7 attached immediately downstream of a spacer region of about 70 nucleotides in length. In a preferred embodiment, an anthranilate promoter of the present invention comprises nucleotides 1239-1268 of SEQ ID NO:7 attached immediately downstream of a spacer region of about 65 nucleotides in length. In a preferred embodiment, an anthranilate promoter of the present invention comprises nucleotides 1239-1268 of SEQ ID NO:7 attached immediately downstream of a spacer region of about 60 nucleotides in length. In a preferred embodiment, an anthranilate promoter of the present invention comprises nucleotides 1239-1268 of SEQ ID NO:7 attached immediately downstream of a spacer region of about 55 nucleotides in length. In a preferred embodiment, an anthranilate promoter of the present invention comprises nucleotides 1239-1268 of SEQ ID NO:7 attached immediately downstream of a spacer region of about 50 nucleotides in length.

In a preferred embodiment, the spacer region has the sequence of the region shown in SEQ ID NO:7, beginning about 100 nucleotides upstream of nucleotide 1239 and ending with nucleotide 1238. In a preferred embodiment, the spacer region has the sequence of the region shown in SEQ ID NO:7, beginning about 85 nucleotides upstream of nucleotide 1239 and ending with nucleotide 1238. In a preferred embodiment, the spacer region has the sequence of the region shown in SEQ ID NO:7, beginning about 80 nucleotides upstream of nucleotide 1239 and ending with nucleotide 1238. In a preferred embodiment, the spacer region has the sequence of the region shown in SEQ ID NO:7, beginning about 75 nucleotides upstream of nucleotide 1239 and ending with nucleotide 1238. In a preferred embodiment, the spacer region has the sequence of the region shown in SEQ ID NO:7, beginning about 70 nucleotides upstream of nucleotide 1239 and ending with nucleotide 1238. In a preferred embodiment, the spacer region has the sequence of the region shown in SEQ ID NO:7, beginning about 65 nucleotides upstream of nucleotide 1239 and ending with nucleotide 1238. In a preferred embodiment, the spacer region has the sequence of the region shown in SEQ ID NO:7, beginning about 60 nucleotides upstream of nucleotide 1239 and ending with nucleotide 1238. In a preferred embodiment, the spacer region has the sequence of the region shown in SEQ ID NO:7, beginning about 55 nucleotides upstream of nucleotide 1239 and ending with nucleotide 1238. In a preferred embodiment, the spacer region has the sequence of the region shown in SEQ ID NO:7, beginning about 50 nucleotides upstream of nucleotide 1239 and ending with nucleotide 1238. In a preferred embodiment, the spacer region has the sequence of nucleotides 1139-1238 of SEQ ID NO:7, an anthranilate promoter of this preferred embodiment comprising nucleotides 1139-1238 of SEQ ID NO:7.

In a preferred embodiment, an anthranilate promoter of the present invention comprises nucleotides 1239-1274 of SEQ ID NO:7 attached immediately upstream of said spacer segment and attached immediately downstream of said spacer region. In a preferred embodiment, an anthranilate promoter of the present invention comprises nucleotides 1139-1274 of SEQ ID NO:7.

In a preferred embodiment, in expression systems in which an anthranilate promoter according to the present invention is used, the host cell will also contain and express at least one nucleic acid encoding an anthranilate promoter activator protein. Even more preferred is the use of multiple expressed copies of such a Pant activator protein-encoding nucleic acid. In a preferred embodiment, the Pant activator protein will have an amino acid sequence of SEQ ID NO:9 or the residue 268 (Ala) variant thereof. In a preferred embodiment, the nucleic acid encoding the Pant activator protein will contain the sequence of bases 1-990 of SEQ ID NO:8 or the base 802 variation thereof; or the complement thereof of any of these; or the RNA equivalent of any of these.

Mutant and Closely Related Activator Proteins and Polynucleotides Encoding Them The same methods as described below for use in obtaining mutant promoters may similarly be used to obtain mutant activator proteins and the coding sequences and genes thereof In this case, at least a portion of the gene encoding a given activator protein, e.g., all or part of the coding sequence thereof, may be used as, or be used to form a probe for use in hybridization probing; or may provide a base sequence to be used in the form of an information string, identical or at least 90% identical thereto, to search a database for structurally related sequences for testing. Likewise all or part of the amino acid sequence of the activator protein may be used as an information string to perform such searching. The resulting sequences identified by hybridization or bioinformatic searching are then tested for promoter activation activity and/or for improved properties.

Thus, also included within the present invention are transcriptional activator proteins having an amino acid sequence at least 90% identical to and heterologous to that of: a Pben activator protein having an amino acid sequence of any one of residues 1-335 of SEQ ID NO:2, residues 1-335 of SEQ ID NO:2 containing Asn152, residues 21-335 of SEQ ID NO:2, and residues 21-335 of SEQ ID NO:7 containing Asn152; and a Pant activator protein having an amino acid sequence of any one of residues 1-330 of SEQ ID NO:9 and residues 1-330 of SEQ ID NO:9 containing Ala268. The present invention also includes polynucleotides encoding said mutant and closely related transcriptional activator proteins.

Tandem Promoters

In a preferred embodiment, a tandem promoter of the present invention comprises a (natively) non-catabolite-repressed promoter attached upstream of a natively catabolite-repressed promoter, in which the catabolite repression of the latter promoter is overcome and/or a different improved promoter property is exhibited.

In a preferred embodiment, both the non-catabolite-repressed promoter and the natively catabolite-repressed promoter are selected from the prokaryotes. In a preferred embodiment, both the non-catabolite-repressed promoter and the natively catabolite-repressed promoter are selected from the bacteria. In a preferred embodiment, both the non-catabolite-repressed promoter and the natively catabolite-repressed promoter are selected from the Proteobacteria; preferably Gram negative Proteobacteria. In a preferred embodiment, both the non-catabolite-repressed promoter and the natively catabolite-repressed promoter are selected from the "Pseudomonads and closely related bacteria" or from a Subgroup thereof, as defined below.

In a preferred embodiment, both promoters are selected from the same species. In a preferred embodiment, both promoters are obtained from the same species in a genus selected from among the "Pseudomonads and closely related bacteria" or among a Subgroup thereof, as defined below. In a preferred embodiment, both promoters are selected from organisms of the genus *Pseudomonas*. In a preferred embodiment, both promoters are selected from the same species in the genus *Pseudomonas*. In a preferred embodiment, both promoters are selected from *Pseudomonas fluorescens*. In a preferred embodiment, both promoters are selected from *Pseudomonas fluorescens* biotype A.

The individual promoters selected for use in a tandem promoter according to the present invention may be activatable promoters, repressible promoters, or a combination thereof. In a preferred embodiment at least one of, and preferably both of, the individual promoters will be activatable promoters. Where a repressible promoter is present as a promoter element in such a tandem promoter, preferably the cell in which the tandem promoter is utilized will also contain at least one, and preferably more than, one copy of an expressible coding sequence for a repressor protein that mediates the regulation of the promoter. Where an activatable promoter is present as a promoter element in such a tandem promoter, preferably the cell in which the tandem promoter is utilized will also contain at least one, and preferably more than, one copy of an expressible coding sequence for an activator protein that mediates the regulation of the promoter.

In a preferred embodiment, both promoters are obtained as native promoters of genes or operons encoding enzyme(s) and/or pathway(s) capable of enabling a cell to utilize (e.g., to import, export, transport, or metabolize) alternative carbon source(s). In a preferred embodiment, the non-catabolite-repressed promoter is a native promoter of a gene or operon encoding enzyme(s) and/or pathway(s) capable of biocatalytically degrading anthranilate, i.e. an "anthranilate promoter." In a preferred embodiment, the natively catabolite-repressed promoter is a native promoter of a gene or operon encoding enzyme(s) and/or pathway(s) capable of biocatalytically degrading benzoate, i.e. a "benzoate promoter." In a preferred embodiment, the anthranilate promoter is an anthranilate promoter as described above. In a preferred embodiment, the benzoate promoter is a benzoate promoter as described above.

In a preferred embodiment, a tandem promoter of the present invention is a construct formed by linking the *Pseudomonas fluorescens* native anthranilate promoter to, and upstream of, the *Pseudomonas fluorescens* native benzoate promoter. The present inventors have found such a promoter arrangement to be inducible with anthranilic acid, anthranilic acid analogs (e.g., haloanthranilic acids), and biologically acceptable salts thereof (e.g., sodium anthranilate); with benzoic acid and biologically acceptable salts thereof; and with o-toluate (o-toluate has been found to induce this promoter as well as does anthranilate).

In a preferred embodiment, the non-catabolite-repressed promoter is attached immediately upstream of the natively catabolite-repressed promoter. This attachment may be made directly between the promoters (or directly between native nucleic acid segments containing the promoters) or by means of an, e.g., polynucleotide linker connecting the promoters (or segments) to one another. In a preferred embodiment, the non-catabolite-repressed promoter is attached upstream of the natively catabolite-repressed promoter, via an inter-promoter linker. Preferably, the inter-promoter linker will be a polynucleotide, provided that that polynucleotide linker contains no sequence that functions as a transcription termination signal. In a preferred embodiment the inter-promoter linker is a polynucleotide of about 100 nucleotides in length. In a preferred embodiment, the inter-promoter linker is less than 100 nucleotides in length. In a preferred embodiment the inter-promoter linker is a polynucleotide of length equal to or less than 90 nucleotides. In a preferred embodiment the inter-promoter linker is a polynucleotide of length equal to or less than 80 nucleotides. In a preferred embodiment the inter-promoter linker is a polynucleotide of length equal to or less than 70 nucleotides. In a preferred embodiment the inter-promoter linker is a polynucleotide of length equal to or less than 60 nucleotides. In a preferred embodiment the inter-promoter linker is a polynucleotide of length equal to or less than 50 nucleotides. In a preferred embodiment the inter-promoter linker is a polynucleotide of length equal to or less than 40 nucleotides. In a preferred embodiment the inter-promoter linker is a polynucleotide of length equal to or less than 30 nucleotides. In a preferred embodiment the inter-promoter linker is a polynucleotide of length equal to or less than 20 nucleotides. In a preferred embodiment, the inter-promoter linker is equal to or less than 10 nucleotides. In a preferred embodiment the inter-promoter linker is a polynucleotide at least about 5 nucleotides, or at least about 10 nucleotides, or at least about 20 nucleotides, or at least about 30 nucleotides, or at least about 40 nucleotides in length. In a preferred embodiment the inter-promoter linker is a polynucleotide about 5 to about 50 nucleotides, or about 10 to about 50 nucleotides, or about 20 to about 50 nucleotides, or about 30 to about 50 nucleotides in length. In a preferred embodiment the inter-promoter linker is a polynucleotide having a length of 43 nucleotides. In a preferred embodiment the inter-promoter linker has the sequence of SEQ ID NO:14.

In a preferred embodiment, a tandem promoter comprises an anthranilate promoter sequence selected from the group consisting of nucleotides 1221-1365, 1221-1371, 1329-1365, and 1329-1371 of SEQ ID NO:13 attached upstream of a benzoate promoter sequence selected from the group consisting of nucleotides 1430-1503, 1430-1509, 1477-1503, and 1477-1509 of SEQ ID NO:13. In a preferred embodiment, a tandem anthranilate-benzoate promoter of the present invention comprises, for the benzoate promoter portion, both a "−35 to −10 region" and a benzoate promoter activator (or repressor) protein binding site, preferably an activator protein binding site. In a preferred embodiment, a tandem promoter comprises nucleotides 1329-1503 of SEQ ID NO:13. In a preferred embodiment, a tandem promoter comprises nucleotides 1329-1509 of SEQ ID NO:13. In a preferred embodiment, a tandem promoter comprises nucleotides 1221-1503 of SEQ ID NO:13. In a preferred embodiment, a tandem promoter comprises nucleotides 1221-1509 of SEQ ID NO:13. In a preferred embodiment, a tandem promoter comprises nucleotides 1329-1544 of SEQ ID NO:13. In a preferred embodiment, a tandem promoter comprises nucleotides 1221-1544 of SEQ ID NO:13.

In a preferred embodiment, an anthranilate activator protein coding sequence or a benzoate activator protein coding sequence is included in, and expressed within, a system using, respectively, a Pant-containing or Pben-containing tandem promoter of the present invention Where the tandem promoter contains both a Pant and a Pben, preferably an anthranilate promoter activator protein coding sequence is selected, for example, the anthranilate activator protein (AntR) described above in regard to Pant promoters. Even more preferred in any expression system is the presence of such an expressed coding sequence in multiple copies.

Sources of Native Promoters for Use in Constructing Tandem Promoters Tandem promoters according to the present invention may be constructed, e.g., by obtaining from prokaryotic cells, preferably bacterial cells, native promoters from genes or operons encoding enzyme(s) responsible for utilization of alternative carbon sources, i.e. carbon sources other than glucose. In a preferred embodiment, the bacterial cells will be chosen from among the bacterial cells belonging to the "Pseudomonads and closely related bacteria," or any one of the 19 Subgroups thereof, as defined below.

Bacteria are known that are capable of utilizing a wide range of alternative carbon sources. In a preferred embodiment, a native promoter selected for use in constructing a tandem promoter will be obtained from a gene or operon from which is expressed an enzyme(s) having degradative activity toward at least one alternative carbon source chosen from among:

Straight-chain, Branched-chain, Cyclic, and Alicyclic Homo- and Hetero-Hydrocarbons (saturated or unsaturated) and derivatives thereof;

Aromatic and Alkylaryl Compounds and derivatives thereof, e.g., benzene, naphthalene, anthracene, phenanthrene, toluene, xylene, biphenyl;

Heterocyclic compounds and derivatives thereof, e.g., steroids, sterols, allantoins, cyclic terpenes, yohimbines, indoles, imidazoles, oxazines, quinolines, phenazines, xanthenes;

Alcohols & Polyols and derivatives thereof, e.g., ethanol, phenol, naphthol, cresol, catechol, glycerol, benzyl alcohol, menthanol;

Acids, Esters, Anhydrides, and derivatives thereof, e.g., acetate, salicylate, benzoate, hydroxybenzoate, anthranilate, phthalate, benzylalkaioates, gentisate, amino acids (e.g., glutamate); mono-, di-, and tri-carboxylic acids; fatty acids, lipids, and related compounds;

Aldehydes, Ketones, Ethers and derivatives thereof;

Halogenated Organic Compounds and derivatives thereof, e.g., chlorobenzoate, chlorophenols, iodonaphthalene, bromoxylene, fluoropentane, trichloropropane;

Organo-Phosphorus Compounds and derivatives thereof, e.g., organophosphonates, organophosphates, organophosphites, phospha-compounds, phospho-compounds;

Organo-Sulphur Compounds and derivatives thereof, e.g., organosulfonates, organosulfates, organosulfites, thia-compounds, thio-compounds;

Organo-Nitrogen Compounds and derivatives thereof, e.g., organonitrates, nitroorganics (e.g., nitrobenzoate, nitrophenol), cyano compounds, hydrazines, amines, imines, amides, imides, purines, pyrimidines, aza-compounds, azo-compounds;

Other Hetero-Organic compounds, e.g., organo-boron compounds, organo-silicon compounds, organometallic compounds, multi-heteroatom-organic compounds; and Multi-functional organic compounds.

The genes and operons encoding these biodegradative activities may be either catabolite-repressed or non-catabolite-repressed, as described above. The native promoters thereof may be readily obtained by one of ordinary skill in the art by methods well known in the art, e.g., by isolating mRNA encoding such an enzyme and using the nucleic acid sequence of the mRNA or cDNA made therefrom, to probe the bacterial genome (or a record of the genomic sequence thereof) for occurrence(s) of the corresponding DNA gene. This is followed by identification of regulatory regions, including a transcription start site, located in the segment of DNA immediately upstream of (i.e. 5' to) the coding sequence. Expression constructs containing such regulatory region nucleic acid sequences are then formed and the expression construct(s) tested for induction in bacterial host cells by one or more alternative carbon source compounds, both in the presence and absence of glucose. This provides catabolite-repressed and non-catabolite-repressed promoters that may be used in constructing a tandem promoter according to the present invention.

A variety of catabolite repressed and non-catabolite-repressed genes and operons are known that either (a) encode enzymes that utilize (e.g., that transport, anabolize, or catabolize) alternative carbon sources or (b) encode regulatory genes that control expression from such enzyme-encoding gene(s) and operon(s). The promoter of a typical gene or operon of this type is regulated in that transcription therefrom depends upon, le. the promoter is induced or derepressed by, the presence of a relevant alternative carbon source or an analog compound thereof.

Examples of such catabolite repressed genes and operons include, e.g.:

the styABCD operon of *Pseudomonas fluorescens* ST, which encodes enzymes required for the conversion of styrene to phenylacetate [Ref. 8];

the xylCMABN operon of *P. putida* mt-2, which encodes enzymes required for the transformation of toluene to benzoate and the transformation of xylenes to toluates [Ref. 9];

the alkBFGHJKL operon of *Burkholderia cepacia*, which encodes enzymes, including alkane hydroxylase, required for metabolism of alkanes and alkenes [Ref. 10];

the *P. aeruginosa* gene, oprD, which encodes a specific porin that facilitates the uptake of basic amino acids, and of the carbapenem antibiotic, imipenem, a thienamycin derivative [Ref. 11];

the *P. aeruginosa* gene, aotJ, which is part of an operon encoding enzymes required for the transport of arginine and ornithine [Ref. 12]; and the *P. putida* and *P. aeruginosa* genes, bkdR, which encode a protein regulating expression of an operon encoding a branched-chain keto acid dehydrogenase complex that is required for the metabolism of the branched-chain amino acids [Ref 13].

Examples of such non-catabolite-repressed genes and operons include, e.g.:

the ttgDEF operon of *P. putida* DOT-TIE, which encodes enzymes of a secondary toluene efflux system [Ref. 14];

the *P. aeruginosa gene*, gdhb, which encodes an arginine-inducible NAD(+)-dependent glutamate dehydrogenase [Ref. 15]; and the putA and putP genes of *P. putida* mt-2, which encode enzymes necessary for proline utilization [Ref. 16].

Mutant and Closely Related Sequences of Promoters and Polypeptides

Mutant promoters made from a promoter(s) of a preferred embodiment hereof may also be created using any of the various random and/or directed, mutagenesis techniques known in the art. In a preferred embodiment, site-specific mutagenesis will be performed (e.g. via mutagenic oligonucleotide-directed mutagenesis). In a preferred embodiment, an improved mutant promoter will be selected from a library of mutants made by an error-prone polymerase chain reaction (EP-PCR) performed on a promoter polynucleotide. Multiple rounds of mutagenesis may be performed either upon the pool of polynucleotides resulting from a previous round or upon one or more mutant promoters selected therefrom. Advantageous mutations identified in improved promoters may also be combined to obtain further increases in improvement (e.g., cumulative improvements).

In addition to generating mutant tandem promoters by performing one or more of the techniques described above upon a non-mutant tandem promoter (i.e. a tandem promoter in which the individual promoter elements are themselves of native sequence), individual mutant promoters may be used in forming a tandem promoter(s) according to the present invention. For example, two mutant promoters may be linked together, or a mutant promoter and a non-mutant promoter may be linked together, to form a tandem promoter according to the present invention. In addition, directed mutagenesis and/or recombination may be performed (e.g., using a technique such as is described in WO 91/16427) in order to create multiple promoter-promoter combinations in a given round.

Closely related promoters may be obtained by use of polynucleotides containing tandem and/or native promoter constructs and/or elements as hybridization probes, under stringent hybridization conditions, according to any of the various protocols known in the art. An exemplary stringent hybridization protocol is set forth below. Alternatively, a peptide nucleic acid (PNA), or other nucleic acid analog, having a base sequence of such a promoter may be used as a hybridization probe. Preferably the probe will contain a base sequence of at least about 6, at least about 8, at least about 10, at least about 15, at least about 20, at least about 25, at least about 30, at least about 35, at least about 40, at least about 45, or at least about 50 bases in length. In a preferred embodiment, the probe will contain a base sequence of not more than about 100, about 80, about 60, or about 50 bases in length. In a preferred embodiment, the probe will contain a base sequence of about 20 to about 50, or about 25 to about 45, or about 30 to about 40 bases in length.

In order to perform hybridization probing of target nucleic acids, e.g., target DNA at least suspected of containing a promoter, the target DNA to be probed is denatured, blotted crosslinked onto a nitrocellulose or nylon membrane according to standard protocols (see Sambrook et al. [Cold Spring Harbor Press], *Current Protocols in Molecular Biology* [John Wiley and Sons, Inc.]). The blot is then pre-hybridized using standard buffers as described in Sambrook et al. or Current Protocols or using a commercially available hybridization buffer such as EXPRESSHYB (BD Biosciences Clontech, Palo Alto, Calif.). Pre-hybridization may be performed at temperatures ranging from 50-65° C.

The probe to be used (e.g., DNA representing or containing an, e.g., anthranilate or benzoate, promoter fragment) may be labeled to identify specifically bound target DNA and/or the probe nucleic acid may be used as a primer to enzymatically copy specifically bound target DNA. The probe may be labeled according to any of the techniques known in the art. For example, the probe may be labeled with any detectable label, including, but not limited to a: peptide tag, an immunogenic moiety, avidin, biotin, a fluorescent or colored moiety, a detectable chelate, or a radionuclide moiety. In a preferred embodiment, a nucleic acid, preferably DNA, is used as the probe. In a preferred embodiment, the DNA of the probe is labeled. In a preferred embodiment, the label is a radioactive moiety, e.g., a radionuclide-containing compound such as $\gamma$-$^{32}$P dATP. Kits for performing such labeling are commercially available: for example, the HIGH PRIME DNA labeling kit (Roche Molecular Biochemicals, Indianapolis, Ind.), in conjunction with a radionuclide-containing nucleoside-5'-triphosphate, such as $\gamma$-$^{32}$P dATP, may be used. The probe or labeled probe is then boiled and added to the pre-hybridization buffer. The blot is incubated with the probe at 50-65° C. overnight, then washed twice with 2×SSC/0.5%SDS for 5 minutes per wash at room temperature. Then the blot is washed twice with 0.1×SSC/0.1%SDS for 15 minutes per wash at 50-65° C. The blot is then developed as appropriate for viewing the specifically bound labeled probe. For example, if a radionuclide moiety is used as the label on the probe, the blot is used to expose a film or a phosphor screen for viewing.

Alternately, an oligo or set of oligos may be designed that hybridize to known promoter elements (i.e., the −35 and −10 sequences with intervening sequence), or to known activator protein binding sites; a set of degenerate oligos can be designed, at least one of which can hybridize to the target sequence of interest. These may be used as probes for Southern blot analysis as described above, or may be used to initiate synthesis of single (one oligo) or double (two oligos) stranded DNA that may be homologous to the promoter of interest. DNA synthesis may be carried out with, e.g., Taq polymerase (with extension carried out at 72° C. or as indicated in the manufacturer's protocol), or other polymerase, with buffers supplied by the manufacturer, 1-5 mM concentration of primer, and 0.2-1 mM final concentration dNTP mix. Annealing temperature can be varied to attain optimal amplification. Extension times for the polymerase may be 20-60 seconds, depending upon length of desired product. A linker could be added to the single-stranded fragment to allow for synthesis of a second strand and amplification, if necessary. Double-stranded fragments may then be sequenced using primers designed for extension/amplification. If restriction sites are also designed onto the oligo, this fragment could subsequently be directly cloned into a standard vector, such as pUC18, e.g., for sequence analysis;

The target nucleic acid to which the probe has specifically bound is then selected by means of selecting probe-target hybrids that have been viewed. In a preferred embodiment, a selected target nucleic acid, will be at least 90% homologous, i.e. at least 90% identical in base sequence to the probe or the complementary base sequence thereof (wherein T and U are considered equivalent bases for these purposes). In a preferred embodiment, a selected target nucleic acid will be at least about 95% homologous thereto. In a preferred embodiment, a selected target nucleic acid will be at least about 98% homologous thereto. Where such a target nucleic acid is situated as a portion within a larger polynucleotide molecule, the target nucleic acid, or a fragment containing said target nucleic acid, may be recovered therefrom by any means known in the art, including, e.g., endonuclease digestion and exonuclease digestion.

Alternatively, the base sequence of the probe may be used, in the form of an information string, to perform searching of a nucleotide sequence record, such as a paper or electronic database record of nucleotide sequences present in polynucleotides containing with a polynucleotide source. The search parameters may specify that a successful match must be 100% identical (100% homologous) or less than 100% identical (heterologous) to the probe information string. Preferably, the search parameters will be selected so that a successful match must be at least 90% homologous, at least 95% homologous, or at least 98% homologous to the probe information string. Preferably, the search parameters will be selected so that a successful match must be heterologous to the probe information string. Once a successful match has been identified, the polynucleotide source corresponding thereto is selected.

Alternatively, a probe information string may be created by altering a first information string representing the nucleobase sequence of a given promoter from a modified information string representing a heterologous nucleobase sequence at least 90% homologous to that of said given promoter. This modified information string may then be used to synthesize a polynucleotide molecule containing the base sequence thereof or may be used to perform searching of a nucleotide sequence record for an identical information string as described above. Upon a successful match, the polynucleotide source corresponding thereto is selected.

Once a polynucleotide at least 90% homologous to the probe sequence is obtained, it is then tested, by forming an expression construct therewith, inserting the expression construct into a transcription system (or transcription and translation system), such as a prokaryotic host cell, and screening the resulting system, e.g., the transformed cell, for the ability of the polynucleotide to direct transcription. Preferably, the screening also involves identifying at least one promoter property improved relative to that of the original promoter.

Alignments and searches for homologous sequences can be performed using the U.S. National Center for Biotechnology Information (NCBI) program, MegaBLAST (currently available at http://www.ncbi.nlm.nih.gov/BLAST/). Use of this program with options for percent identity set at 90% will identify those sequences with 90% or greater homology to the query sequence. Other software known in the art is also available for aligning and/or searching for homologous sequences, e.g., sequences at least 90% homologous to an information string containing a promoter base sequence or activator-protein-encoding base sequence according to the present invention. For example, sequence alignments for comparison to identify sequences at least 90% homologous to a query sequence can be performed by use of, e.g., the GAP, BEST-FIT, BLAST, FASTA, and TFASTA programs available in the GCG Sequence Analysis Software Package (available from the Genetics Computer Group, University of Wisconsin Biotechnology Center, 1710 University Avenue, Madison, Wis. 53705), with the default parameters as specified therein, plus a parameter for the extent of homology set at 90%. Also, for example, the CLUSTAL program (available in the PC/Gene software package from Intelligenetics, Mountain View, Calif.) may be used.

These and other sequence alignment methods are well known in the art and may be conducted by manual alignment, by visual inspection, or by manual or automatic application of a sequence alignment algorithm, such as any of those embodied by the above-described programs. Various useful algorithms include, e.g.: the similarity search method described in W. R. Pearson & D. J. Lipman, *Proc. Nat'l Acad. Sci. USA* 85:244448 (April 1988); the local homology method described in T. F. Smith & M. S. Waterman, in *Adv. Appl. Math.* 2:482-89 (1981) and in *J. Molec. Biol.* 147:195-97 (1981); the homology alignment method described in S. B. Needleman & C. D. Wunsch, *J. Molec. Biol.* 48(3):443-53 (March 1970); and the various methods described, e.g., by W. R. Pearson, in *Genomics* 11(3):635-50 (November 1991); by W. R. Pearson, in *Methods Molec. Biol.* 24:307-31 and 25:365-89 (1994); and by D. G. Higgins & P. M. Sharp, in *Comp. Appl'ns in Biosci.* 5:151-53 (1989) and in *Gene* 73(1): 237-44 (15 Dec. 1988).

In a preferred embodiment, a nucleobase polymer (e.g., a polynucleotide or polynucleotide analog) that is heterologous to, i.e. whose base sequence is heterologous to, the base sequence of a given promoter, promoter region, or other non-codon- or non-anti-codon-containing polynucleotide segment, will be at least 90% homologous thereto; preferably about or at least 93% homologous thereto; preferably about or at least 95% homologous thereto; preferably about or at least 96% homologous thereto; preferably about or at least 97% homologous thereto; preferably about or at least 98% homologous thereto; preferably about or at least 99% thereto.

In a preferred embodiment, a polypeptide (or segment thereof) that is heterologous to, i.e. whose amino acid sequence is heterologous to, the amino acid sequence of a given polypeptide (or segment thereof) will be at least 90% homologous thereto; preferably about or at least 93% homologous thereto; preferably about or at least 95% homologous thereto; preferably about or at least 96% homologous thereto; preferably about or at least 97% homologous thereto; preferably about or at least 98% homologous thereto; preferably about or at least 99% thereto.

In a preferred embodiment, a nucleobase polymer (or segment thereof) that is heterologous to, i.e. whose base sequence is heterologous to, the base sequence of a given codon- or anti-codon-containing polynucleotide (or segment thereof), will be at least 90% homologous thereto; preferably about or at least 93% homologous thereto; even more preferably about or at least 95% homologous thereto; still more preferably about or at least 96% homologous thereto. In a preferred embodiment, such a nucleobase polymer has such a degree of homology to the given codon- or anti-codon-containing polynucleotide that the amino acid sequence encoded by the nucleobase polymer will be at least 90% homologous to the amino acid sequence of the given polynucleotide; preferably about or at least 93% homologous thereto; preferably about or at least 95% homologous thereto; preferably about or at least 96% homologous thereto; preferably about or at least 97% homologous thereto; preferably about or at least 98% homologous thereto; preferably about or at least 99% thereto.

In a preferred embodiment, a nucleobase polymer (or segment thereof) that is heterologous to, i.e. whose base sequence is heterologous to, the base sequence of a given codon- or anti-codon-containing polynucleotide (or segment thereof), is about or at least 97% homologous thereto; preferably about or at least 98% homologous thereto; preferably about or at least 99% thereto.

Expression Constructs

In an expression construct, e.g., a gene or operon, according to the present invention, a nucleic acid containing a transcription product-encoding sequence will be operably linked to a promoter according to the present invention, spacer. Where the transcription product is an mRNA or a precursor molecule thereto, the spacer will be a ribosome-binding-site-containing spacer ("RBS spacer").

A "transcription product-encoding polynucleotide" is any polynucleotide that contains a transcription product-encoding sequence, wherein the transcription product is any functional or structural RNA molecule, including, but not limited to, e.g., mRNA, rRNA, tRNA, cRNA, gRNA, hnRNA, miRNA, mtRNA, nRNA, ncRNA, pRNA, satRNA, scRNA, siRNA, snRNA, snoRNA, srpRNA, stRNA, tmRNA, vRNA, anti-sense RNA (also called "aRNA"), aptamer RNA, chromosomal RNA, enzyme-inhibitor RNA, genetic-control-element RNA, plastid RNA, ribozyme RNA, self-cleaving RNA, self-splicing RNA, telomerase RNA (TER or TERC), X-chromosome-inactivator RNA (XIST RNA), or a precursor RNA of any such RNA molecule. In a preferred embodiment, the transcription product will be an mRNA or a precursor RNA molecule thereto.

Other elements may be included in an expression construct. Such elements include, but are not limited to, e.g.: transcriptional enhancer sequences; translational enhancer sequences; leader peptide-encoding sequences, e.g., for intracellular-targeting-peptides or secretion signal peptides; propeptide-, pre-peptide-, and pre-pro-peptide-coding sequences; other promoters; translational start and stop signals; polyadenylation signals; transcription terminators; introns; and tag sequences, such nucleotide sequence "tags" and "tag" peptide coding sequences (a "tag" facilitates identification, separation, purification, or isolation of an expressed polynucleotide, for which a nucleotide sequence tag is used, or of an expressed polypeptide, for which a "tag" peptide coding sequence is used).

At a minimum, an expression construct according to the present invention will include (in addition to a promoter and either a spacer or an RBS-spacer, operably linked to a transcription product-encoding sequence), a transcriptional terminator. Where the transcription product is an mRNA or pre-mRNA, the expression construct will, at minimum, further include translational start and stop signals operably linked to the transcription product-encoding sequence. The term "operably linked," as used herein, refers to any configuration in which the transcriptional and any translational regulatory elements are covalently attached to the encoding sequence in such disposition(s), relative to the encoding sequence, that in and by action of the host cell, the regulatory elements can direct the expression of the coding sequence. Every regulatory element in the expression construct must be "operably linked" to the transcription product-encoding sequence. In cases wherein the cell processes the expression construct before transcription or processes a precursor RNA transcribed from the expression construct, the regulatory element(s) must be so positioned that the cell's processing systems can manipulate the expression construct or the pre-RNA to operably link the regulatory element(s) therein. Likewise, in cases wherein the expression construct is present in the cell in distinct segments of polynucleotide(s), the segments, i.e. the polynucleotide molecules or regions collectively containing the regulatory element(s) and transcription product-encoding sequence(s), must be so positioned that the cell can manipulate the segments to create or to re-connect the expression construct wherein the regulatory elements are operatively linked to the transcription product-encoding sequence, and/or are so positioned that the cell's processing systems can manipulate a to-be-transcribed pre-RNA to operably link the regulatory element(s) thereto.

Any prokaryotic ribosome binding site (RBS) may be utilized in such an expression construct. Preferably a bacterial RBS is utilized. In preferred embodiment, an RBS operative in Gram positive bacteria is used; even more preferably an RBS operative in Gram negative bacteria is used. Many specific and a variety of consensus RBSs are known, e.g., those described in and referenced by D. Frishman et al., Starts of bacterial genes: estimating the reliability of computer predictions, *Gene* 234(2):257-65 (8 Jul. 1999); and B. E. Suzek et al., A probabilistic method for identifying start codons in bacterial genomes, *Bioinformatics* 17(12):1123-30 (December 2001). In addition, either native or synthetic RBSs may be used, e.g., those described in: EP 0207459 (synthetic RBSs); O. Ikehata et al., Primary structure of nitrile hydratase deduced from the nucleotide sequence of a *Rhodococcus* species and its expression in *Escherichia coli, Eur. J. Biochem.* 181(3):563-70 (1989) (native RBS sequence of AAGGAAG, SEQ ID NO:42); or J. A. Wells et al., Cloning, sequencing, and secretion of *Bacillus amyloliquefaciens* subtilisin in *Bacillus subtilis, Nucl. Acids Res.* 11(22):7911-25 (1983) (native RBS sequence of GAGAGG, SEQ ID NO:43).

Furthermore, one or more marker genes or reporter genes may be used in an expression system to verify expression. Many such useful marker or reporter genes are known in the art. See, e.g., U.S. Pat. No. 4,753,876 to Hemming et al., and DL Day et al., in *J. Bact.* 157(3):937-39 (March 1984). In a preferred embodiment, the marker gene is selected from among the antibiotic resistance-conferring marker genes. In a preferred embodiment, the marker gene is selected from among the tetracycline and kanamycin resistance genes. In a preferred embodiment, a reporter gene is selected from among those encoding: (1) fluorescent proteins (e.g., GFP); (2) colored proteins; and (3) fluorescence- or color-facilitating or -inducing proteins, the latter class (3) including, e.g., luminases, alkaline phosphatases, and beta-galactosidases. Alkaline phosphatases hydrolyze BCIP to produce a blue color, and hydrolyze PNPP to produce a yellow color. Beta-galactosidases hydrolyze X-gal to create a blue-colored derivative, and hydrolyze ONPG to produce a yellow color. Fluorescent substrates are also available for alkaline phosphatase and β-galactosidase.

Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al; U.S. Pat. Nos. 4,695,455 and 4,861,595 to Barnes et al.; U.S. Pat. No. 4,755,465 to Gray et al.; and U.S. Pat. No. 5,169,760 to Wilcox.

Vectors

A great many bacterial vectors are known in the art as useful for expressing proteins in bacteria, and any of these may be used for expressing the genes according to the present invention. Such vectors include, e.g., plasmids, cosmids, and phage expression vectors. Examples of useful plasmid vectors include, but are not limited to, the expression plasmids pMB9, pBR312, pBR322, pML122, RK2, RK6, and RSF1010. Other examples of such useful vectors include those described by, e.g.: N. Hayase, in *Appl. Envir. Microbiol.* 60(9):3336-42 (September 1994); A. A. Lushnikov et al, in *Basic Life Sci.* 30:657-62 (1985); S. Graupner & W. Wackernagel, in *Biomolec. Eng.* 17(1): 11-16. (October 2000); H. P. Schweizer, in *Curr. Opin. Biotech.* 12(5):439-45 (October 2001); M. Bagdasarian & K. N. Timmis, in *Curr. Topics Microbiol. Immunol.* 96:47-67 (1982); T. Ishii et al., in *FEMS Microbiol. Lett.* 116(3):307-13 (Mar. 1, 1994); I. N. Olekhnovich & Y. K. Fomichev, in *Gene* 140(1):63-65 (Mar. 11, 1994); M. Tsuda & T. Nakazawa, in *Gene* 136(1-2):257-62 (Dec. 22, 1993); C. Nieto et al., in *Gene* 87(1):14549 (Mar. 1, 1990); J. D. Jones & N. Gutterson, in *Gene* 61(3):299-306 (1987); M. Bagdasarian et al., in *Gene* 16(1-3):237-47 (Dec 1981); H. P. Schweizer et al., in *Genet. Eng.* (NY) 23:69-81 (2001); P. Mukhopadhyay et al., in *J. Bact.* 172(1):477-80 (January 1990); D. O. Wood et al., in J. Bact. 145(3):1448-51 (March 1981); and R. Holtwick et al., in *Microbiology* 147(Pt 2):337-44 (February 2001).

Further examples of useful *Pseudomonas* expression vectors include those listed in Table 3.

TABLE 3

Some Examples of Useful Expression Vectors

| Replicon | Vector(s) |
|---|---|
| pPS10 | PCN39, pCN51 |
| RSF1010 | PKT261-3 |
|  | PMMB66EH |
|  | PEB8 |
|  | PPLGN1 |
| RK2/RP1 | PRK415 |
|  | PJB653 |
| pRO1600 | PUCP |
|  | PBSP |

The expression plasmid, RSF1010, is described, e.g., by F. Heffron et al., in *Proc. Nat'l Acad. Sci. USA* 72(9):3623-27 (September 1975), and by K. Nagahari & K. Sakaguchi, in *J. Bact.* 133(3):1527-29 (March 1978). Plasmid RSF1010 and derivatives thereof are particularly useful vectors in the present invention. Exemplary, useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such a, e.g., pMYC1803. Other exemplary useful vectors include those described in U.S. Pat. No. 4,680,264 to Puhler et al.

In a preferred embodiment, an expression plasmid is used as the expression vector. In a preferred embodiment, RSF1010 or a derivative thereof is used as the expression vector. In a preferred embodiment, pMYC1050 or a derivative thereof, or pMYC1803 or a derivative thereof, is used as the expression vector.

A vector can then be transformed into a bacterial host cell.

Transformation

Transformation of the host cells with the vector(s) may be performed using any transformation methodology known in the art, and the bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or CaCl/Mg$^{2+}$ treatment.

In addition to the above elements of an expression construct, the bacterial host cell will also contain at least one, and preferably more than one, copy of a gene containing a coding sequence of an activator or repressor protein of the promoter. This gene may be attached to the expression construct, or it may be part of a separate nucleic acid. In a preferred embodiment, an anthranilate activator protein having the amino acid sequence encoded by the complement of the coding sequence shown at nucleotides 4-993 of SEQ ID NO:7 will be utilized; and a benzoate activator protein encoded by nucleotides 225-1229 or nucleotides 285-1229 of SEQ ID NO:1 will be utilized. Preferably, the activator- (or repressor-) encoding gene will be constitutively expressed in the bacterial host cell. When expression of the (e.g., exogenous) coding sequence is desired, the host cell will be contacted with an activator (or de-repressor) compound to induce expression. In a preferred embodiment, the bacterial host cell will be contacted with anthranilic or benzoic acid or a biologically acceptable salt (preferably a sodium salt) thereof, in the case of anthranilate and benzoate promoters, respectively. In a preferred embodiment for a tandem promoter, the bacterial host cell will be contacted with an inducer compound that induces either the natively catabolite-repressed promoter element or the (natively) non-catabolite-repressed promoter element thereof. In a preferred embodiment of a tandem promoter, benzoic acid, anthranilic acid, or biologically acceptable salt(s) (preferably a sodium salt) thereof, will be used as the inducer (activator) compound.

Host Cells

In a preferred embodiment, the host cell in which the promoter is used will be selected from the prokaryotes. In a preferred embodiment, the host cell is selected from the bacteria. In a preferred embodiment, the host cell is selected from the Proteobacteria. In a preferred embodiment, the host cell is selected from the "Pseudomonads and closely related bacteria" or from a Subgroup thereof, as defined below. In a preferred embodiment, the host cell is selected from the genus *Pseudomonas*. A particularly preferred species of *Pseudomonas* is *P. fluorescens*; even more preferred is *Pseudomonas fluorescens* biotype A.

In a preferred embodiment, both the organism from which the native promoter(s) are obtained and the host cells in which a promoter according to the present invention is utilized, will be selected from the prokaryotes. In a preferred embodiment, both the organism from which the native promoter(s) are obtained and the host cells in which a promoter according to the present invention is utilized, will be selected from the bacteria. In a preferred embodiment, both the bacteria from which the native promoter(s) are obtained and the bacterial host cells in which a promoter according to the present invention is utilized, will be selected from the Proteobacteria. In a preferred embodiment, both the bacteria from which the native promoter(s) are obtained and the bacterial host cells in which a promoter according to the present invention is utilized, will be selected from the Pseudomonads and closely related bacteria or from a Subgroup thereof, as defined below.

In a preferred embodiment, both the promoter source organism and the host cell will be selected from the same species. Preferably, the species will be a prokaryote; more preferably a bacterium, still more preferably a Proteobacterium. In a particularly preferred embodiment, both the promoter source organism and the host cell will be selected from the same species in a genus selected from the Pseudomonads and closely related bacteria or from a Subgroup thereof, as defined below; more preferably from the genus *Pseudomonas*. Especially preferred is the species *Pseudomonas fluorescens*; even more preferably, *Pseudomonas fluorescens* biotype A.

In a preferred embodiment, the host cells in which the promoter is used will lack biocatalyst(s) effective to degrade the inducer compound: e.g., benzoate or anthranilate or an analog thereof, and/or the degradation product(s) thereof, if any, that is directly responsible for induction; and/or gratuitous inducer compounds. Such host cells are readily obtained as knock-out mutants. For example, the present inventors have found that, in the case of an anthranilate promoter, inactivation of at least the antA portion of the host cell's antABC operon does inhibit the consumption of an anthranilate inducer and thereby permits the inducer to effect lasting induction. The antA open reading frame encodes the large subunit of the first enzyme utilized in the pathway for degradation of anthranilate. Similarly, in the case of a benzoate promoter, the inventors have found that inactivation of the benAB portion of the host cell's benABCD operon, e.g., by deletion or mutation, does inhibit the consumption of a benzoate inducer, thereby improving the level of induction; inactivation of at least the beta portion would work similarly, as this encodes the large subunit of the first enzyme utilized in the pathway for degradation of benzoate.

Gene knock-outs may be constructed according to any method known effective in the art. Gene inactivation by insertion of a gene has been previously described. See, e.g., D L Roeder & A Collmer, *Marker-exchange mutagenesis of a pectate lyase isozyme gene in Erwinia chrysanthemi*, J Bacteriol. 164(1):51-56 (1985). Briefly, a portion of the gene to be disrupted in amplified and cloned into a vector containing a selectable marker, such as an antibiotic resistance gene, that is not able to replicate in the target host. Homologous recombination between the chromosomal copy of the gene and the portion of the target gene contained on the plasmid results in the disruption of the chomosomal copy of the gene and incorporation of the antibiotic resistance marker. Alternatively, transposon mutagenesis and selection for desired phenotype (such as the inability to metabolize benzoate or anthranilate) may be used to isolate bacterial strains in which target genes have been insertionally inactivated. See, e.g., K Nida & P P Cleary, *Insertional inactivation of streptolysin S expression in Streptococcus pyogenes*, J Bacteriol. 155(3):1156-61 (1983). Specific mutations or deletions in a particular gene can be constructed using cassette mutagenesis, for example, a described in J A Wells et al., *Cassette mutagenesis: an efficient method for generation of multiple mutations at defined sites*, Gene 34(2-3):315-23 (1985); whereby direct or random mutations are made in a selected portion of a gene, and then incorporated into the chromosomal copy of the gene by homologous recombination.

Pseudomonads and Closely Related Bacteria

The "Pseudomonads and closely related bacteria," as used herein, is co-extensive with the group defined herein as "Gram(−) Proteobacteria Subgroup 1." "Gram(−) Proteobacteria Subgroup 1" is more specifically defined as the group of Proteobacteria belonging to the families and/or genera described as falling within that taxonomic "Part" named "Gram-Negative Aerobic Rods and Cocci" by R. E. Buchanan and N. E. Gibbons (eds.), *Bergey's Manual of Determinative Bacteriology*, pp. 217-289 (8th ed., 1974) (The Williams & Wilkins Co., Baltimore, Md., USA) (hereinafter "Bergey (1974)"), and the genus, *Acinetobacter*. Table 4 presents the families and genera of organisms listed in the Bergey taxonomic "Part."

TABLE 4

Families and Genera Listed in the Part, "Gram-Negative Aerobic Rods and Cocci" (in Bergey (1974))

| | |
|---|---|
| Family I. Pseudomonadaceae | *Gluconobacter* |
| | *Pseudomonas* |
| | *Xanthomonas* |
| | *Zoogloea* |
| Family II. Azotobacteraceae | *Azomonas* |
| | *Azotobacter* |
| | *Beijerinckia* |
| | *Derxia* |
| Family III. Rhizobiaceae | *Agrobacterium* |
| | *Rhizobium* |
| Family IV. Methylomonadaceae | *Methylococcus* |
| | *Methylomonas* |
| Family V. Halobacteriaceae | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

"Gram(−) Proteobacteria Subgroup 1" contains all Proteobacteria classified thereunder, as well as all Proteobacteria that would be classified thereunder according to the criteria used in forming that taxonomic "Part." As a result, "Gram(−) Proteobacteria Subgroup 1" excludes, e.g.: all Gram-positive bacteria; those Gram-negative bacteria, such as the Enterobacteriaceae, which fall under others of the 19 "Parts" of this Bergey (1974) taxonomy; the entire "Family V. Halobacteriaceae" of this Bergey (1974) "Part," which family has since been recognized as being a non-bacterial family of Archaea; and the genus, *Thermus*, listed within this Bergey (1974) "Part," which genus which has since been recognized as being a non-Proteobacterial genus of bacteria.

Also in accordance with this definition, "Gram(−) Proteobacteria Subgroup 1" further includes those Proteobacteria belonging to (and previously called species of) the genera and families defined in this Bergey (1974) "Part," and which have since been given other Proteobacterial taxonomnic names. In some cases, these re-namings resulted in the creation of entirely new Proteobacterial genera. For example, the genera *Acidovorax*, *Brevundimonas*, *Burkholderia*, *Hydrogenophaga*, *Oceanimonas*, *Ralstonia*, and *Stenotrophomonas*, were created by regrouping organisms belonging to (and previously called species of) the genus *Pseudomonas* as defined in Bergey (1974). Likewise, e.g. the genus *Sphingomonas* (and the genus *Blastomonas*, derived therefrom) was created by regrouping organisms belonging to (and previously called species of) the genus *Xanthomonas* as defined in Bergey (1974). Similarly, e.g., the genus *Acidomonas* was created by regrouping organisms belonging to (and previously called species of) the genus *Acetobacter* as defined in Bergey (1974). Such subsequently reassigned species are also included within "Gram(−) Proteobacteria Subgroup 1" as defined herein.

In other cases, Proteobacterial species falling within the genera and families defined in this Bergey (1974) "Part" were simply reclassified under other, existing genera of Proteobacteria. For example, in the case of the genus *Pseudomonas*, *Pseudomonas enalia* (ATCC 14393), *Pseudomonas nigrifaciens* (ATCC 19375), and *Pseudomonas putrefaciens* (ATCC 8071) have since been reclassified respectively as *Alteromonas haloplanktis*, *Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have since been reclassified respectively as *Pseudoalteromonas nigrifaciens* and *Pseudoalteromonas piscicida*. Such subsequently reassigned Proteobacterial species are also included within "Gram(−) Proteobacteria Subgroup 1" as defined herein.

Likewise in accordance with this definition, "Gram(−) Proteobacteria Subgroup 1I" fiurter includes Proteobacterial species that have since been discovered, or that have since been reclassified as belonging, within the Proteobacterial families and/or genera of this Bergey (1974) "Part." In regard to Proteobacterial families, "Gram(−) Proteobacteria Subgroup 1" also includes Proteobacteria classified as belonging to any of the families: Pseudomonadaceae, Azotobacteraceae (now often called by the synonym, the "Azotobacter group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram(−) Proteobacteria Subgroup1" include: 1) Azotobacter group bacteria of the genus *Azorhizophilus*; 2)

Pseudomonadaceae family bacteria of the genera *Cellvibrio, Oligella*, and *Teredinibacter;* 3) Rhizobiaceae family bacteria of the genera *Chelatobacter, Ensifer, Liberibacter* (also called "*Candidatus Liberibacter*"), and *Sinorhizobium;* and 4)Methylococcaceae family bacteria of the genera *Methylobacter, Methylocaldum, Methylomicrobium, Methylosarcina*, and *Methylosphaera.*

In a preferred embodiment, the bacteria are selected from "Gram(−) Proteobacteria Subgroup 1," as defined above.

In a preferred embodiment, the bacteria are selected from "Gram(−) Proteobacteria Subgroup 2." "Gram(−) Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beijerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera; Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); *Oceanimonas* (4); and *Acinetobacter* (160).

Exemplary species of "Gram(−) Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophaga flava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); *Oceanimonas doudoroffii* (ATCC 27123); and *Acinetobacter calcoaceticus* (ATCC 23055).

In a preferred embodiment, the bacteria are selected from "Gram(−) Proteobacteria Subgroup 3." "Gram(−) Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas; Oceanimonas;* and *Acinetobacter.*

In a preferred embodiment, the bacteria are selected from "Gram(−) Proteobacteria Subgroup 4." "Gram(−) Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas; Oceanimonas;* and *Acinetobacter.*

In a preferred embodiment, the bacteria are selected from "Gram(−) Proteobacteria Subgroup 5." "Gram(−) Proteobacteria Subgroup 5" is defined as the group of Proteobacteria of the following genera: *Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas; Oceanimonas;* and *Acinetobacter.*

In a preferred embodiment, the host cell is selected from "Gram(−) Proteobacteria Subgroup 6." "Gram(−) Proteobacteria Subgroup 6" is defined as the group of Proteobacteria of the following genera: *Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas; Oceanimonas;* and *Acinetobacter.*

In a preferred embodiment, the bacteria are selected from "Gram(−) Proteobacteria Subgroup 7." "Gram(−) Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas; Oceanimonas;* and *Acinetobacter.*

In a preferred embodiment, the bacteria are selected from "Gram(−) Proteobacteria Subgroup 8." "Gram(−) Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Pseudomonas; Stenotrophomonas; Xanthomonas; Oceanimonas;* and *Acinetobacter.*

In a preferred embodiment, the bacteria are selected from "Gram(−) Proteobacteria Subgroup 9." "Gram(−) Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas; Oceanimonas;* and *Acinetobacter.*

In a preferred embodiment, the bacteria are selected from "Gram(−) Proteobacteria Subgroup 10." "Gram(−) Proteobacteria Subgroup 10" is defined as the group of Proteobacteria of the following genera: *Burkholderia; Ralstonia; Pseudomonas; Stenotrophomonas; Xanthomonas;* and *Acinetobacter.*

In a preferred embodiment, the bacteria are selected from "Gram(−) Proteobacteria Subgroup 11." "Gram(−) Proteobacteria Subgroup 11" is defined as the group of Proteobacteria of the genera: *Pseudomonas; Stenotrophomonas; Xanthomonas;* and *Acinetobacter.*

In a preferred embodiment, the bacteria are selected from "Gram(−) Proteobacteria Subgroup 12." "Gram(−) Proteobacteria Subgroup 12" is defined as the group of Proteobacteria of the following genera: *Burkholderia; Ralstonia; Pseudomonas.*

In a preferred embodiment, the bacteria are selected from "Gram(−) Proteobacteria Subgroup 13." "Gram(−) Proteobacteria Subgroup 13" is defined as the group of Proteobacteria of the following genera: *Burkholderia; Raistonia; Pseudomonas; Xanthomonas;* and *Acinetobacter.*

In a preferred embodiment, the bacteria are selected from "Gram(−) Proteobacteria Subgroup 14." "Gram(−) Proteobacteria Subgroup 14" is defined as the group of Proteobacteria of the following genera: *Pseudomonas* and *Xanthomonas.*

In a preferred embodiment, the bacteria are selected from "Gram(−) Proteobacteria Subgroup 15." "Gram(−) Proteobacteria Subgroup 15" is defined as the group of Proteobacteria of the genus *Pseudomonas.*

In a preferred embodiment, the bacteria are selected from "Gram(−) Proteobacteria Subgroup 16." "Gram(−) Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomnonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beijerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronti* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans (ATCC 19244); Pseudomonas pertucinogena* (ATCC 190); *Pseudomonas pictorum* (ATCC 23328); *Pseudomonas psychrophila; Pseudomonas fulva* (ATCC 31418); *Pseudomonas monteilli* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis;* and *Pseudomonas xiamenensis.*

In a preferred embodiment, the bacteria are selected from "Gram(−) Proteobacteria Subgroup 17." "Gram(−) Proteobacteria Subgroup 17" is defined as the group of Proteobacteria known in the art as the "fluorescent Pseudomonads" including those belonging, e.g. to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii;* and *Pseudomonas veronii.*

In a preferred embodiment, the bacteria are selected from "Gram(−) Proteobacteria Subgroup 18." "Gram(−) Proteobacteria Subgroup 18" is defined as the group of all subspecies, varieties, strains, and other sub-special units of the species *Pseudomonas fluorescens,* including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); and *Pseudomonas fluorescens* subsp. *cellulosa* (NCMB 10462).

In a preferred embodiment, the bacteria are selected from "Gram(−) Proteobacteria Subgroup 19." "Gram(−) Proteobacteria Subgroup 19" is defined as the group of all strains of *Pseudomonas fluorescens* biotype A. A particularly preferred strain of this biotype is *P. fluorescens* strain MB101 (see U.S. Pat. No. 5,169,760 to Wilcox), and derivatives thereof.

In a particularly preferred embodiment, the bacteria are selected from "Gram(−) Proteobacteria Subgroup 1." In a particularly preferred embodiment, the bacteria are selected from "Gram(−) Proteobacteria Subgroup 2." In a particularly preferred embodiment, the bacteria are selected from "Gram(−) Proteobacteria Subgroup 3." In a particularly preferred embodiment, the bacteria are selected from "Gram(−) Proteobacteria Subgroup 5." In a particularly preferred embodiment, the bacteria are selected from "Gram(−) Proteobacteria Subgroup 7." In a particularly preferred embodiment, the bacteria are selected from "Gram(−) Proteobacteria Subgroup 12." In a particularly preferred embodiment, the bacteria are selected from "Gram(−) Proteobacteria Subgroup 15." In a particularly preferred embodiment, the bacteria are selected from "Gram(−) Proteobacteria Subgroup 17." In a particularly preferred embodiment, the bacteria are selected from "Gram(−) Proteobacteria Subgroup 18." In a particularly preferred embodiment, the bacteria are selected from "Gram(−) Proteobacteria Subgroup 19."

An expression system according to the present invention can be cultured in any fermentation format. For example, batch, fed-batch, semi-continuous, and continuous fermentation modes of any volume may be employed herein.

In the present invention, growth, culturing, and/or fermentation of the host cells is performed within a temperature range permitting survival of the host cells, preferably a temperature within the range of about 4° C. to about 55° C., inclusive. Thus, e.g., the terms "growth" (and "grow," "growing"), "culturing" (and "culture"), and "fermentation" (and "ferment," "fermenting"), as used herein in regard to the host cells of the present invention, inherently and necessarily means "growth," "culturing," and "fermentation," within a temperature range of about 4° C. to about 55° C., inclusive. In addition, "growth" is used to indicate both biological states of active cell division and/or enlargement, as well as biological states in which a non-dividing and/or non-enlarging cell is being metabolically sustained, the latter use of the term "growth" being synonymous with the term "maintenance."

In addition, growth "under conditions permitting expression" when used in regard to the bacterial host cells and expression systems of the present invention, is defined herein to mean: (1) growth of the recombinant bacterial host cells per se, where the promoter used in the control sequence operably linked to the coding sequence is a constitutive promoter; and (2) where the promoter used in the control sequence operably linked to the coding sequence is a regulated promoter, (a) growth of the recombinant bacterial host cells in the presence of (i.e. in contact with) an inducer thereof, and (b) growth of the recombinant bacterial host cells in the absence of an inducer thereof, followed by addition of such an inducer to the system, thereby causing contact between the cell and the inducer.

Biocatalyst Preparation

Once the coding sequence(s) under control of the promoter is expressed, the resulting gene product(s) and/or secondary products (e.g., metabolites) resulting from expression of the gene product(s) can be separated, isolated, and/or purified using any recovery and/or purification methods known in the art as useful for such a product, e.g., a protein, nucleic acid, or other molecule. Alternatively, the host cells themselves can be used, e.g., in whole cell bioreactors or in other applications.

EXAMPLES

Materials & Methods

Promoters and Promoter-Plasmid Constructs

The following promoter nucleotide sequences are referred to herein,
  Pben509: nucleotides c994-c1502 of SEQ ID NO:1.
  Pben278: nucleotides g1228-c1502 of SEQ ID NO:1.
  Pben88: nucleotides g1228-c1316 of SEQ ID NO:1 with deletion of g1306.
  Pant713: nucleotides c592-c1304 of SEQ ID NO:7.
  Pant705: nucleotides c592-g1296 of SEQ ID NO:7.
  Pant311: nucleotides c994-c1304 of SEQ ID NO:7.
  Pant289: nucleotides 994-1283 of SEQ ID NO:7 with deletion of g1269 and t1278.
  AntR+Pant (also Pant+AntR): a1-c1395 of SEQ ID NO:13.
  Ptandem: SEQ ID NO:13.

The following promoterless plasmid constructs are referred to herein.
  pDOW1017: No Promoter, but carrying a promoterless lacZ reporter gene.
  pDOW1033: No Promoter, but carrying a promoterless phoA reporter gene.

The plasmid promoter constructs listed in Tables 5 and 6 are referred to herein.

TABLE 5

Plasmid Individual Promoter Constructs

| Promoter Type | Plasmid Designation | Promoter or Activator-Promoter Sequence Identity | Construct Description |
|---|---|---|---|
| Benzoate | pDOW1028 | SEQ ID NO:1 N1228-N1502 | Pben278::lacZ |
| | pDOW1041 | SEQ ID NO:1 N1228-N1502 | Pben278::phoA |
| | pDOW1019 | SEQ ID NO:1 N994-N1502 | Pben509::lacZ |
| | pDOW1102 | SEQ ID NO:1 N1228-N1316 with deletion of g1306 | Pben88::lacZ |
| | pDOW1081 | SEQ ID NO:1 N1228-N1316 with deletion of g1306 | Pben88::phoA |
| | pDOW1083 | SEQ ID NO:1 N1228-N1316 with deletion of g1306 and substitution of native -10 'tacggt' 1296-1301 by 'tataat' | Pben88(-10con)::phoA |
| | pDOW1126 | SEQ ID NO:1 N1-N1316 with deletion of g1306 | BenR-Pben88(-10con)::lacZ |
| | pDOW1090 | SEQ ID NO:1 N1-N1316 with deletion of g1306 | BenR-Pben88(-10con)::phoA |
| | pDOW1100 | SEQ ID NO:1 N1228-N1316 with deletion of g1306 and substitution of native -10 'tacggt' 1296-1301 by 'taaggt' | Pben88(-10benAc)::lacZ |

TABLE 5-continued

Plasmid Individual Promoter Constructs

| Promoter Type | Plasmid Designation | Promoter or Activator-Promoter Sequence Identity | Construct Description |
|---|---|---|---|
| | pDOW1084 | SEQ ID NO:1 N1228-N1316 with deletion of g1306 and substitution of native -10 'tacggt' 1296-1301 by 'taaggt' | Pben88(-10benAc)::phoA |
| Anthranilate | pDOW1039 | SEQ ID NO:7 N1-N1304 | AntR-Pant |
| | pDOW1101 | SEQ ID NO:7 N994-N1304 | Pant311::lacZ |
| | pDOW1035 | SEQ ID NO:7 N1-N1304 | AntR-Pant::lacZ |
| | pDOW1056 | SEQ ID NO:7 N1-N1304 | AntR-Pant::phoA |
| | pDOW1029 | SEQ ID NO:7 N592-N1304 | Pant713::lacZ |
| | pDOW1095 | SEQ ID NO:7 N1-N1283 with deletion of t1278 | AntR-Pant(-10wt)::phoA |
| | pDOW1082 | SEQ ID NO:7 N994-N1283 with deletion of g1269 and t1278 and substitution of native -10 region 'ttaat' 1264-1268 by consensus -10 region 'tataat' | Pant289(-10con)::phoA |
| | pDOW1098 | SEQ ID NO:7 N1-N1283 with deletion of g1269 and t1278 and substitution of native -10 region 'ttaat' 1264-1268 by consensus -10 region 'tataat' | AntR-Pant289(-10con)::phoA |
| Mosaic | pDOW1099 | SEQ ID NO:7 N1-N1283 with deletion of g1269 and t1278 and substitution of native Pant -10 region 'ttaat' 1264-1268 by native Pben -10 region 'tacggt' | AntR-Pant289(-10ben)::phoA |

TABLE 6

Plasmid Tandem Promoter Constructs

| Plasmid Designation | Promoter or Activator-Promoter Sequence Identity | Construct Description |
|---|---|---|
| pDOW1057 | SEQ ID NO:13 | AntR-Ptandem::lacZ |
| pDOW1111 | SEQ ID NO:13 N1085-N1541 | Pant311-Pben278::lacZ |
| pDOW1107 | SEQ ID NO:13 N1-N1518 with deletion of g1508 | AntR-Ptandem[Pben88(-10wt)]::lacZ |
| pDOW1108 | SEQ ID NO:13 N1-N1518 with deletion of g1508 and substitution of Pben native -10 'tacggt' 1498-1503 by 'tataat' | AntR-Ptandem[Pben88(-10con)]::lacZ |
| pDOW1109 | SEQ ID NO:13 N1-N1518 with deletion of g1508 and substitution of Pben native -10 'tacggt' 1498-1503 by 'taaggt' | AntR-Ptandem[Pben88(-10benAc)]::lacZ |

The oligonucleotides listed in Table 7 are utilized in the following examples.

TABLE 7

Oligonucleotides Used Herein

| Primer Name | Sequence (all listed 5'→3') | |
|---|---|---|
| AntAKO5 | GGAATTCTTCGTGACGATGCG | (SEQ ID NO:16) |
| AntAKO3 | CGGGATCCGCTCGCGATGCTGC | (SEQ ID NO:17) |
| lacZPE | GGATGTGCTGCAAGGC | (SEQ ID NO:18) |

TABLE 7-continued

Oligonucleotides Used Herein

| Primer Name | Sequence (all listed 5'→3') | |
|---|---|---|
| lacZPE2 | GTAACCATGGTCATCGC | (SEQ ID NO:19) |
| M13forward | GTAAAACGACGGCCAGT | (SEQ ID NO:20) |
| M13reverse | AACAGCTATGACCATG | (SEQ ID NO:21) |
| Bambenwtshort | CGGGATCCGTATCAGGCGCCTCACCGTACGTGCTC | (SEQ ID NO:22) |
| Bambenconshort | CGGGATCCGTATCAGGCGCCTCATTATACGTGCTC | (SEQ ID NO:23) |
| BambenAcshort | CGGGATCCGTATCAGGCGCCTCACCTTACGTGCTC | (SEQ ID NO:24) |
| Bamantwtshort | CGGGATCCGCTAACGGTGAGCCATTAAGCGGCTGC | (SEQ ID NO:25) |
| Bamantconshort | CGGGATCCGCTAACGGTGAGCATTATAGCGGCTGC | (SEQ ID NO:26) |
| BenactKO-for | CGCGACACATTGCTGCCCAG | (SEQ ID NO:27) |
| BenactKO-rev | AGTATCAGCCATCGCACCTT | (SEQ ID NO:28) |
| 1803H3seq | GTCCTGCAATTTCAGCCGA | (SEQ ID NO:29) |
| BenL278 | CCTTAATTAAGTTAAGCGACGTGCGC | (SEQ ID NO:30) |
| 3'Antactiv | CCCAAGCTTCTATCGAGGCAAGCCAG | (SEQ ID NO:31) |
| Benact5' | AGCTTTGTTTAAACGCATGACGTTGTTGATTC | (SEQ ID NO:32) |
| H3_5'BenAKOclean | CCCAAGCTTGCCATGAGGCGGAAAACGCTGC | (SEQ ID NO:33) |
| H3_3'BenBKOclean | CCCAAGCTTCGGTGATCGCCACGCTGTCGC | (SEQ ID NO:34) |
| BenKOmega | CATACGTCATGGCCCTCCGTTGTTC | (SEQ ID NO:35) |
| InvbenKOmega | GAACAACGGAGGGCCATGACGTATG | (SEQ ID NO:36) |
| 5'BenA_Seq | CTGCTGGAAAACGCCTGCCTGGAG | (SEQ ID NO:37) |
| Seq_3'BenB | GAGCACTTCAAGCATCGACAGGAAC | (SEQ ID NO:38) |
| 1261-8378F | CTTCAGATCCAGACTCACCAG | (SEQ ID NO:39) |
| 1261-103R | GACCATGATTACGCCAAGCGC | (SEQ ID NO:40) |
| M13R21 | CACACAGGAAACAGCTATGAC | (SEQ ID NO:41) |

Host Cells:

E. coli JM109 (obtained from Promega Corp.), E. coli TOP10 (obtained from Invitrogen Corp.), and Pseudomonas fluorescens biotype A (strains MB 101 and MB214). P. fluorescens MB214 is a derivative of strain MB101 (a wild-type prototrophic P. fluorescens biovar A). MB214 had been prepared by integrating the E. coli lacIZYA operon (deleted of the lacZ promoter region) into the chromosome of strain MB 101 to provide a host cell wherein the lac promoter and its derivatives can be regulated by lactose or IPTG to drive inducible expression of transgenes of interest. The MB101 strain is Lac(−) whereas the MB214 strain is Lac(+).

Inducer Compounds

As used in the Examples below, an "anthranilate" inducer means sodium anthranilate, and a "benzoate" inducer means sodium benzoate.

Transformation Protocols

E. coli: Transformations of E. coli were performed as per the manufacturer's protocol, using strain JM109 chemically competent cells from Promega (Madison, Wis.).

P. fluorescens: Electroporation of P. fluorescens was performed by subculturing 1 mL of an overnight culture (grown in rich medium; the present examples used Luria-Bertni Broth, Miller (ie. LB Broth, Miller) (available from Difco, Detroit, Mich.) into 50 mL LB Broth, Miller and incubating at 30° C. with shaking until an A600 measurement falls within the range of 0.4-0.6. The resulting cells were washed twice with 50 mL cold ddH20 and resuspend in 1 mL cold ddH20. To 100 µL aliquots of competent cells were added approximately 10 ng of a plasmid of interest, in a 0.2 cm gap electroporation cuvette (Bio-Rad Laboratories, Inc., Hercules, Calif.). Electroporation was performed under the following conditions: 200 Ohms, 25 µF, 2.25 kV. This was followed by the addition of 1 mL cold LB broth. Cells were permitted to recover on ice for 2 minutes, then incubated at 30° C., with no shaking, for 2 hours to overnight. Cells were then plated on selective medium; the present examples used LB agar Miller (Luria-Bertani) (available from Difco, Detroit, Mich.), supplemented with 15 µg/mL tetracycline (Fisher Scientific, Pittsburgh, Pa.) as the selective medium.

Cell Growth Protocols:

Cell growth for induction: Strains of interest were grown overnight (at 30° C. with shaking at 250 rpm) in 1×M9 minimal salts medium (diluted from a 5× preparation purchased from Fisher Scientific, Pittsburgh, Pa.) supplemented with 0.5% or 1% (w/v) glucose, 1 mM $MgSO_4$, and trace elements (for trace elements, the present examples used a solution containing salts of sodium, magnesium, manganese, iron, and cobalt, all at less than 0.5 mg/mL final concentration). Strains were then subcultured 1:4 in the same medium to a volume of 10 or 20 mL and then induced with 0-10 mM concentrations of anthranilate or benzoate, as indicated.

Cell growth for plasmid propagation: E. coli cells containing a plasmid of interest were grown overnight in 50-200 mL of LB Broth, Miller, supplemented with 15 μg/ML tetracycline or 100 μg/mL ampicillin (depending on the plasmid to be isolated) at 37° C., with shaking at 250 rpm. Plasmids preparations were performed using the NUCLEOSPIN kit (plasmid DNA purification "miniprep" kit for use with culture volumes up to 5 mL; available from BD Biosciences Clontech, Palo Alto, Calif.) or the NUCLEOBOND kit (plasmid DNA purification "midiprep" kit for use with culture volumes up to 200 ml; available from BD Biosciences Clontech, Palo Alto, Calif.).

Induction Protocols:

Strains of interest were grown overnight at 30° C. in 1×M9 medium supplemented with 0.5% or 1% (w/v) glucose, 1 mM $MgSO_4$, and 5L/L trace elements (as described above), and optionally tetracycline at 15 ug/mL. These were then subcultured 1:4 or 1:5 in the same medium and then induced with indicated concentrations of anthranilate, benzoate, or other inducer, for a desired amount of time (e.g., for 2, 4, 6, 8, 12, or 24 hours, or overnight). Samples were taken at indicated times and those samples were assayed for reporter gene activity. Results are reported at time points taken at a given number of hours post-induction; time points are indicated by either a numeral for the number of hours, and in some cases this number is immediately preceded by the letter "I" indicating post-induction.

EP-PCR Protocol

The following protocol was used for error-prone PCR mutagenesis (see "Mutagenesis of Cloned DNA," in F. M. Ausubel, Current Protocols in Molecular Biology on CD-ROM (2002) (John Wiley & Sons, New York, N.Y.)). The following reagents were combined: 63 μL water, 10 μL 0.1M Tris (pH 8.3), 5 μL 1M KCl, 0.7 μL 1M $MgCl_2$, 4 μL dNTP mix (either mix #1 [25 mM dCTP, 25 mM dTTP, 5 mM dATP, 5 mM dGTP] or mix #2 [20 mM DCTP, 20 mM dTTP; 2 mM dATP, 2 mM dGTP]), 2 μL 100 μM M13forward primer (GTAAAACGACGGCCAGT) (SEQ ID NO:16), 2 μL 100 μM M13reverse primer (AACAGCTATGACCATG) (SEQ ID NO:17), 1 μL (~5 ng) template (consisting of a Pant or Pben promoter polynucleotide cloned into pNEB193, a plasmid available from New England BioLabs, Beverly, Mass.), 2 μL 25 mM $MnCl_2$, and 1 μL Taq polymerase (5 Units/μL, obtained from Invitrogen Corp.). PCR conditions were as follows: 94° C. for 3 min.; 30 cycles of 30 sec. at 94° C., 30 sec. at 50° C., and 90 sec. at 72° C.; hold at 4° C. PCR products were purified using MICROCON YM-100 or MICROCON-PCR columns (nucleic acid purification columns, Millipore Corp., Bedford, Mass.) according to the manufacturer's instructions for AMICON devices. Products were digested with BamHI and HindIII (New England BioLabs) in 1×NEB-UFFER BAMH I+BSA (BamH I restriction endonuclease buffer, available from New England BioLabs) and purified by gel extraction using either QIAEX II (gel extraction kit, from Qiagen, Valencia, Calif.), for fragments of 300 bp and smaller, or PREP-A-GENE (DNA purification kit, from Bio-Rad Laboratories), for fragments larger than 300 bp. The fragments were then cloned upstream of the lacZ or phoA reporter gene of pDOW1017 or pDOW1033, respectively.

Knock-Out Protocols

Construction of AntA Knock-Out. An internal fragment of the antA gene was amplified using primers AntAKO5 (GGAATTCTTCGTGACGATGCG) (SEQ ID NO:16) and AntAKO3 (CGGGATCCGCTCGCGATGCTGC) (SEQ ID NO:17) from P. fluorescens genomic DNA (EcoRI and BamHI sites, respectively, shown in italics). The reaction mixture was formed by combining: 5 μL 10.times.buffer (i.e. the buffer supplied by Invitrogen with the Taq polymerase, which buffer contained 200 mM Tris-HCl (pH 8.4) and 500 mM KCl), 2.5 μL 50 mM $MgCl_2$, 1 μL 10 mM dNTPs, 0.5 μL 100 μM AntKO3, 0.5 μL 100 μM AntKO5, 1 μL (5 Units/μL) Taq polymerase (Invitrogen Corp., Carlsbad, Calif.), 0.5 μL P. fluorescens MB214 genomic DNA (~50 ng), and 39 μL $ddH_2O$. The PCR cycle conditions used were: 2 min. at 96° C.; 30 cycles of 30 sec. at 96° C., 30 sec. at 52° C., and 30 sec. at 72° C. The resulting PCR product was cloned into a plasmid unable to replicate in P. fluorescens (a pUC type plasmid was used, though, e.g., pBR type plasmids will also work). The resulting plasmid was transformed into electrocompetent P. fluorescens cells, and the transformants were selected with the appropriate antibiotic. Since the plasmid cannot replicate in P. fluorescens, only those bacteria which have the plasmid integrated at the antA locus, resulting in two truncated antA ORFs separated by the plasmid backbone, can be selected. Several transformants were cultured in M9 medium+1.0% glucose, 5 mM anthranilate, at 30° C. with shaking for 24 hours, and culture supernatants were analyzed by HPLC for anthranilate concentration.

Construction of BenAB Knock-Out. Generally, following the above-described method for deletion of the AntA gene in P. fluorescens, the plasmid pDOW1139 was constructed to facilitate deletion of the benAB genes as follows. The 3' portion of the benR gene and the 5' portion of the benC gene were amplified using P. fluorescens MB214 genomic DNA as template. The benR region was amplified using primers H3__5'benAKOclean and BenKOmega. The benC region was amplified using primers H3__3'BenBKOclean and Invben-KOmega. For both reactions, the cycling conditions were 95° C. for 5 minutes; (94° C., 30 seconds; 55° C., 30 seconds; 72° C., 1 minute) for 35 times; then 72° C. for 5 minutes. This reaction was performed using Taq polymerase (Invitrogen) according to the manufacturer's protocol. The benR and benC fragments were fused using primers H3__5'benAKOclean and H3__3'benBKOclean, with both fragments as template. This fusion reaction employed KOD HOTSTART DNA polymerase (Novagen) under conditions of 94° C. for 2 minutes; (94° C., 30 seconds; 50° C., 30 seconds; 68° C., 1.5 minutes) for 35 times; then 68° C. for 5 minutes. The expected 1.1 kb fragment was gel purified using QIAEX II (Qiagen) and cloned into SrfI-digested plasmid DNA to form plasmid, pDOW1139. pDOW1139 was then transformed into P. fluorescens). Transformants were selected by plating on LB medium with tetracycline for selection. Since the plasmid could not replicate in P. fluorescens, colonies resistant to tetracycline arose from the plasmid being integrated into the chromosome. The site of integration of the plasmid was analyzed by PCR. To obtain strains that lost the integrated plasmid by recombination between the homologous regions, single colonies of the first transformants were inoculated into liquid LB medium, grown overnight, and then plated onto selective medium to counterselect for loss of the plasmid (data not shown). Isolates having the expected phenotype were selected. DNA from the resulting strains was analyzed by PCR to confirm removal of the benAB region using primers 5'BenA_seq, Seq_3'BenB, M13R21, 1261-8378F and 1261-103R.

Inactivation of the *P. fluorescens* Chromosomal BenR Gene. The open reading frame (ORF) upstream of the benA gene e FIG. ). A DNA fragment containing a portion of the ORF was amplified by PCR using the BenactKOfor and BenactKOrev primers, and *P. fluorescens* MB214 genomic DNA as template. Recombinant Taq polymerase (from Invitrogen Corp.) was used according to the manufacturer's protocol. The cycling profile [94° C. for 2 min.; (94° C. for 30 sec, 62° C. for 30 sec, 72° C. for 30 sec) for 30 cycles; then 72° C. for 7 min] was used. The resulting products were cloned into the pCR2.1 vector (form Invitrogen Corp.) and transformed into *E. coli* Top10 cells. Transformants were screened for insert by colony PCR using the above primers/conditions, and the positive clones were further confirmed by DNA sequencing. The resulting plasmids were then used to insertionally inactivate the corresponding chromosomal ORFs. DNA samples were prepared using a NucLEoBoND plasmid midiprep kit (from Clontech Corp.) and 4 µg of plasmid DNA was transformed into *P. fluorescens* strain MB101. The resulting transformants were screened again by colony PCR. To do this, putative knockout clones were picked into 20 µl $H_2O$ and incubated at 100° C. for 10 min. PCR was performed on the DNA of the resulting lysed cells, using PCR reaction conditions of: 20 µl pre-incubated clone, 5 µl 10×buffer, 3 µl 25 mM $MgCl_2$, 1 µl 10 mM dNTP, 5 µl 5 µM BenactKO-for, 5 µl 5 µM M13F (−40) and M13R (−21), 0.5 µl Taq polymerase (5U/µl; from Promega Corp.), and 5.5 µl $H_2O$. PCR reaction cycle conditions used were: 94° C. for 1 min; (94° C., 1 min; 50° C., 30 sec; 72° C. 2 min.) for 30 times; then 72° C. for 10 min, followed by 4° C. hold. MB101 genomic DNA and pDOW1125 were used as controls. Inactivation of this BenR gene resulted in inability of the knock-out host cells to activate transgenic Pben-reporter gene constructs, as well as inability to metabolize benzoate.

Site-Directed Mutagenesis Protocol

Oligonucleotides used for site directed mutagenesis are found listed among SEQ ID NOs:16-41. Construction of the Pben −10 promoter mutants was conducted as follows. The plasmid pDOW1022 was used as template for polymerase chain reaction (PCR) with 1 uM primer benL278 and 1 µM of bambenconshort, bambenwtshort, or bambenAcshort. Recombinant Taq polymerase (from Invitrogen Corp.) was used according to the manufacturer's instructions. The reaction cycling protocol was 94° C. for 2 min.; (30 sec at 94° C., 30 sec at 62° C., and 30 sec at 72° C.) for 25 times; then 72° C. for 7 min. The resulting products were cloned into the pCR2.1 vector (Invitrogen Corp.) and transformed into *E. coli* TOP10. The insert containing the mutated promoter was digested with BamHI and PacI and subsequently ligated to pDOW1033 digested with the same restriction enzymes yielding plasmids pDOW1081 and 1083-1084, which have a promoter::phoA transcriptional fusion. These plasmids were used as templates to re-amplify the mutant promoters using the primer 1803H3seq and either bambenconshort, bambenwtshort or bambenAcshort and using a recombinant Taq polymerase (from Promega Corp.), according to the manufacturer's instructions. Reaction cycling conditions were 94° C. for 1 min., (1 min at 94° C., 30 sec at 50° C., and 1 min. at 72° C.) for 30 times; then 72 ° C. for 7min. The resulting products were digested with HindIII and BamHI, and subsequently ligated to pDOW1017 that had been digested with the same restriction enzymes. This resulted in formation of promoter:: lacZ fusions pDOW1102, 1106 and 1100.

Construction of Pant-10 promoter mutants was conducted as follows. The plasmid pDOW1039 was used as template for PCR with 1 uM primer 3' Antactiv and 1 uM of primer bamantwtshort or bamantconshort. Recombinant Taq polymerase (from Invitrogen Corp.) was used according to the manufacturer's instructions. The reaction cycling protocol was 94° C. for 2 min.; (30 sec at 94° C., 30 sec at 60° C., and 30 sec at 72° C.) for 25 times; then 72° C. for 7 min. The resulting products were digested with HindHI and BamHI, and cloned into the same sites of pDOW1033: plasmids pDOW1095 and 1098 contain antR-Pant::phoA fusions, with variations of the −10 region of the promoter.

DNA Sequencing Protocol

Cloned inserts were sequenced using ABI PRISM BIG-DYE V2.0 or V3.0 DNA sequencing kit from (Applied Biosystems, Inc., Foster City, Calif.) as follows: 4 µL of premix (containing buffer, Taq polymerase, and dye terminators, as supplied in the Applied Biosystems kit), 50 fmol of plasmid template, 3.2-5 pmol of desired sequencing primer, and 2 µL of 5×buffer (as supplied in the Applied Biosystems kit) were combined (to a fiaal volume of 20 µL). The PCR cycling profile used was: 45 cycles of 30 sec. at 95° C., 20 sec. at 50° C., and 4 min. at 60° C. Samples were purified using SEPHA-DEX G-50 (a bead-form, dextran gel for chromatographic purification of nucleic acids, from Sigma Chemical Company, St. Louis, Mo.), dried, resuspended in formamide, and then run on an ABI3100 automated DNA sequencer (a 16 capillary array, automated DNA sequencer, from Applied Biosystems, Inc.).

Primer Extension Protocol

RNA Isolation. An RNA isolation procedure was followed in order to identify the transcription start sites under the control of the *P. fluorescens* Pant and Pben promoters. The procedure used is as follows. An overnight culture of *P. fluorescens* MB101 carrying the appropriate plasmid was grown in 1×M9 medium supplemented with 1% glucose (w/v), 1 mM $MgSO_4$, and trace elements (as described above) was subcultured 1:4 (v/v) in the same medium to a final volume of 50 mL. The culture was induced with 5 mM benzoate or anthranilate as appropriate for 8 or 24 hours. Cells were pelleted and total RNA isolated using an RNEAsY kit (a "maxi" bacterial RNA isolation kit from Qiagen, Valencia, Cal.). The RNA was resuspended to a final volume of 200 µL and treated with 10 Units of DNAse I (ribonuclease-free, from Ambion, Inc., Austin, Tex.) according to manufacturer's protocol. Following DNAseI treatment, the RNA was purified using an RNEASY column (a "midi" or "mini" RNA purification column, from Qiagen) as appropriate (the RNEASY "midi" column was used for RNA amounts up to 1 mg; the RNEASY "mini" column was used for RNA amounts up to 100 µg). Once purified, the RNA concentration was determined using RIBOGREEN (RNA quantitation kit, from Molecular Probes, Inc., Eugene, Oreg.), following the manufacturer's protocol.

Primer Labeling: This was performed by mixing 1 µL 10 µM primer (either lacZPE, GGATGTGCTGCAAGGC (SEQ ID NO:18), or lacZPE2, GTAACCATGGTCATCGC (SEQ ID NO:19)), 1 µL 10×T4 polynucleotide kinase buffer (700 mM Tris-HCl (pH 7.6), 100 mM $MgCl_2$, 50 mM dithiothreitol (DTT)), 5 µL $^{32}$P-γATP (50 µCi, Amersham-Pharmacia), 1 µL T4 kinase (New England BioLabs), and 2 µL dd$H_2$O; and incubating the resulting reaction mixture at 37° C. for 30-60 min. Following incubation, 5 µL of the reaction mixture was reserved to use for a "sequencing ladder" analysis. 20 µL TE (10 mM Tris, 1 mM EDTA (pH8.0)) was added to the other 5 µL and mixed and the result was spun through a MICROSPIN G-25 column (Amersham-Pharmacia, Piscataway, N.J.) to remove unincorporated nucleotides, thereby yielding a final concentration of 0.2 µM labeled primer.

Sequencing ladder: This was performed according to the protocol that came with the FMOL kit (DNA sequencing kit from Promega Corp.), using 1 picomole (pmol) of the labeled primer described above. Plasmid template used corresponds with that contained in the strain from which RNA was isolated for the extension reaction.

Primer Extension reaction: Primer extension reactions were performed by mixing 10-20 µg of total RNA with 0.2 pmol primer to yield a final volume of 12 µL, followed by incubation at 70° C. 10 min. Then, the following were added: 4 µL 5×SUPERSCRIPT II buffer (250 mM Tris-HCl (pH 8.3), 375 mM KCl, 15 mM $MgCl_2$, available from Life Technologies, now Invitrogen Corp., Carlsbad, Calif.), 2 µL 1M DTT, 1 µL 10 mM dNTPs, and 1 µL SUPERSCRIPT II (reverse transcriptase, from Life Technologies, now Invitrogen), followed by incubation at 42° C. for 1 hour. Then the resulting mixture was treated by either an addition of 5 µL sequencing stop solution (containing formamide and tracking dye, as supplied in the Promega FMOL kit) or, in those cases where the signal was weak, by: precipitation with 2 µL 3M sodium acetate/40 µL 100% ethanol, followed by centrifugation for 10 minutes to pellet suspended matter, drying of the pellet, and resuspension in 4 µL $H_2O$+2 µL sequencing stop solution. The product mixture resulting from the primer extension reaction was then electrophoresed on a LONG RANGER gel (made from 6% pre-mixed gel solution, from Biowhittaker Molecular Applications, Rockland, Me.) containing 8M Urea and 1.2×TBE (ie. Tris-Borate-EDTA, as diluted from 10×TBE obtained from Fisher Scientific, Pittsburgh, Pa.) next to the sequencing ladder, with 0.6×TBE as an electrophoretic "running" buffer. The gel was dried and exposed to a phosphor screen (from Molecular Dynamics, now Amersham Biosciences, Inc., Piscataway, N.J.) to detect radiolabeled DNA fragment, and imaged on the TYPHOON PHOSPHORIMAGER (Molecular Dynamics, now Amersham Biosciences, Inc., Piscataway, N.J.).

Primer extension using Thermoscript reverse transcriptase: 30 ng total RNA, 1 µL 0.2 µM primer, and $ddH_2O$ to a final volume of 12 µL were mixed and then incubated at 70° C. for 10 min. To this mixture were added 4 µL 5×cDNA synthesis buffer (250 mM Tris acetate (pH 8.4), 375 mM potassium acetate, 40 mM magnesium acetate), 1 µL 0.1M DTT, 2 µL 10 mM dNTPs, 1 µL THERMOSCRIPT RT (reverse transcriptase from Invitrogen Corp.), and the resulting mixture was incubated at 55° C. for 1 hour. The reaction product was precipitated, dried, and resuspended in 4 µL ddH2O+2 µL stop solution (described above). All reactions were heated at 70° C. for 2 minutes immediately before being loaded onto the gel as described above. The gel was run as described above.

Microtiter β-Galactosidase Assay

We prepared enough of the following assay medium to provide for each sample well of a 96-well plate (i.e. for all those wells used, with at least one well being used for each time point measured during the reaction course for each sample): 152 µL Z buffer (0.06M $Na_2HPO_4.7H_2O$, 0.04M $NaH_2PO_4.H_2O$, 0.01M KCl, 0.001M $MgSO_4.7H_2O$)+8 µL 1M β-mercaptoethanol. For each 900 µL of the resulting mix, we added one drop of 0.1%SDS and two drops of $CHCl_3$, mixed (using a vortex-type mixer), and then added 144 µL thereof to each well. 16 µL of cells were then added to each well and the plate sealed with a plastic plate sealer. The plate was then mixed (by vortex) for 10 seconds, and then equilibrated to incubation temperature (room temperature) for 5 minutes. 50 µL 4 mg/mL ONPG was then added. When a significant yellow color developed, 90 µL stop solution (1M $Na_2CO_3$) was added and the reaction time recorded. The resulting color intensity for each sample was then read at A420 and A550. In addition, the cell density of each culture providing the 16 µL of cells used in each sample was read at A600. Miller Units were calculated as follows:

1000 * ((A420−(1.75*A550))/(time(in minutes) *0.1 * A600)).

Alkaline Phosphatase Assas

For this assay we prepared SIGMA FAST (p-nitrophenyl phosphate (PNPP) substrate, from Sigma-Aldrich Corp., St. Louis, Mo.) by adding one of each tablet provided by the manufacturer (one table each PNPP and Tris; stored at −20° C.) to 20 mL $ddH_2O$, giving a final concentration of 1 mg/mL PNPP and 0.2M Tris. At each time point, for each sample, 50 µL SIGMA FAST substrate was combined with 5 µL of cells. The result was then incubated at room temperature for 30 minutes. The resulting color intensity for each sample was then read at A410. In addition, the cell density of each culture providing the 5 µL of cells used in each tested sample was read at A600 (i.e. the cell cultures were read in a 96 well plate). The value of A410/(0.1 * A600) was then calculated to express alkaline phosphatase activity/cell.

Example 1

Cloning and Analysis of a Benzoate-Inducible Promoter

Benzoate is an inexpensive, essentially nontoxic compound, making it an ideal candidate for an inducer. A 509 bp region of P. fluorescens DNA was cloned. This region was found located upstream of a putative benA translational start site (FIG. 5), which was part of the coding sequence of a subunit of benzoate dioxygenase. The cloned region was found to contain a benzoate-inducible promoter (Pben), and was named "Pben509".

Benzoate-inducible promoter activity was tested by fusing the DNA fragment containing the putative promoter sequence of Pben509, or of Pben278 (described below), upstream of an easily assayable reporter gene (i.e. either lacZ, which encodes β-galactosidase and was used as the chief reporter gene, orphoA). The resulting plasmid was transformed into P. fluorescens MB101. Following addition of sodium benzoate, induction of β-galactosidase activity was measured using the chromogenic substrate o-nitrophenol-β-D-galactopyranoside (ONPG) (see FIG. 6). Similar experiments were carried out using the phoA reporter gene and the chromogenic substrate p-nitrophenyl phosphate (PNPP). P. fluorescens strains carrying these constructs show β-galactosidase or alkaline phosphatase activity, respectively, upon addition of 1-10 mM sodium benzoate. Varying the concentration of the inducer and/or the time of induction resulted in varying levels of reporter gene expression (data not shown).

Figure 6:
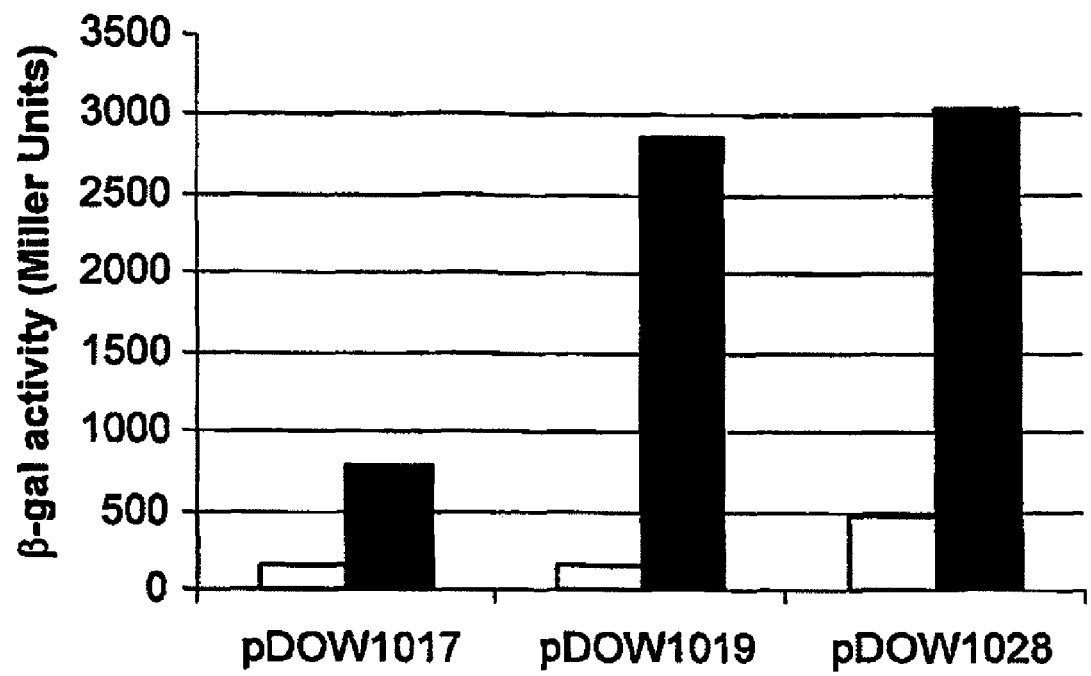
FIG. 6 presents a bar chart showing β-galactosidase induction under the control of Pben509 (pDOW1019) or Pben278 (pDOW1028), in the presence of 0 mm (□) or 10 nM (■) sodium benzoate. pDOW1017 is a vector with no promoter. Results shown are average measurements from triplicate wells assayed at 24 hours post-induction (host cells were grown in a defined salts medium for 24 hours prior to induction).

A truncated version of the promoter-plus-reporter gene construct, containing a 275 bp portion upstream of the predicted translational start site (FIG. 5), which portion was named "Pben278", was found to retain activity similar to that of Pben509 (see FIG. 6).

Both Pben 509 and Pben278 promoter activity was found to be inhibited during fermentation, due to the presence of a small, but significant concentration of glucose. Thus, these promoters are catabolite-repressed.

Northern analysis indicated that expression from Pben occurred only upon addition of the inducer compound (e.g., sodium benzoate), demonstrating that inducible expression of Pben is not leaky like that of the lac family of promoters (data not shown). Primer extension analysis of total RNA isolated from induced cultures of MB101 carrying either Pben509 or Pben278 fused to lacZ indicated that the transcriptional start site was 196 nucleotides (nt) upstream of the predicted benA translational start site. This indicates that the promoter sequence and the positive regulatory cis acting elements are contained within 82 bp upstream of the transcriptional start in the Pben278 clone.

The literature teaches that cis, cis-muconate, a benzoate metabolite, acts to induce the benABCD operon of other bacteria such as *Acinetobacter* sp. and *P. putida*. However, both cis, cis-muconate and the presumed preceding compound in the known metabolic pathway for benzoate degradation, i.e. catechol, fail to induce activity of either Pben509 or Pben278 (data not shown). As a result, either benzoate or an initial benzoate derivative, e.g., 2-hydro-1,2-dihydroxy-benzoate, may be directly responsible for inducing the benzoate promoter.

Example 2

Cloning and Analysis of an Anthranilate-Inducible Promoter

Anthranilate, like benzoate, is an inexpensive low toxic compound that can be utilized by *P. fluorescens*, making it an ideal compound to investigate as an inducer. Four promoter constructs have been cloned upstream of either a lacZ or phoA reporter and have been found to possess similar activity upon induction with anthranilate: Pant713, Pant705, Pant311, and Pant+antR coding sequence (CDS) (FIG. 7). Pant713 and Pant705 have the same 5' end, but Pant713 contains the predicted ribosome binding site of the antA gene, whereas Pant705 does not (see the underlined CCTCC, nucleotides 1299 through 1303 of SEQ ID NO:7, in the final octamer shown for Pant713). In an effort to determine the minimal region of DNA necessary for anthranilate-induced activation, the Pben713 construct was truncated on the 5' terminus to 311 base pairs (bp) The Pant311 construct was found to retain activity similar to that of Pant713 (data not shown). Expansion of the promoter clone to include the transcriptional activator gene 5' of the antA open reading frame (ORF) increased expression levels of the lacZ fusion. The transcriptional start site was mapped to 31 nucleotides upstream of the predicted antA translational start site, for both Pant713 and the expanded clone that includes the transcriptional activator AntR (data not shown; also see FIG. 7). The presence of antR in multi-copy with the lacZ fusion was found to enable faster and stronger induction (see FIG. 8).

Figure 8:
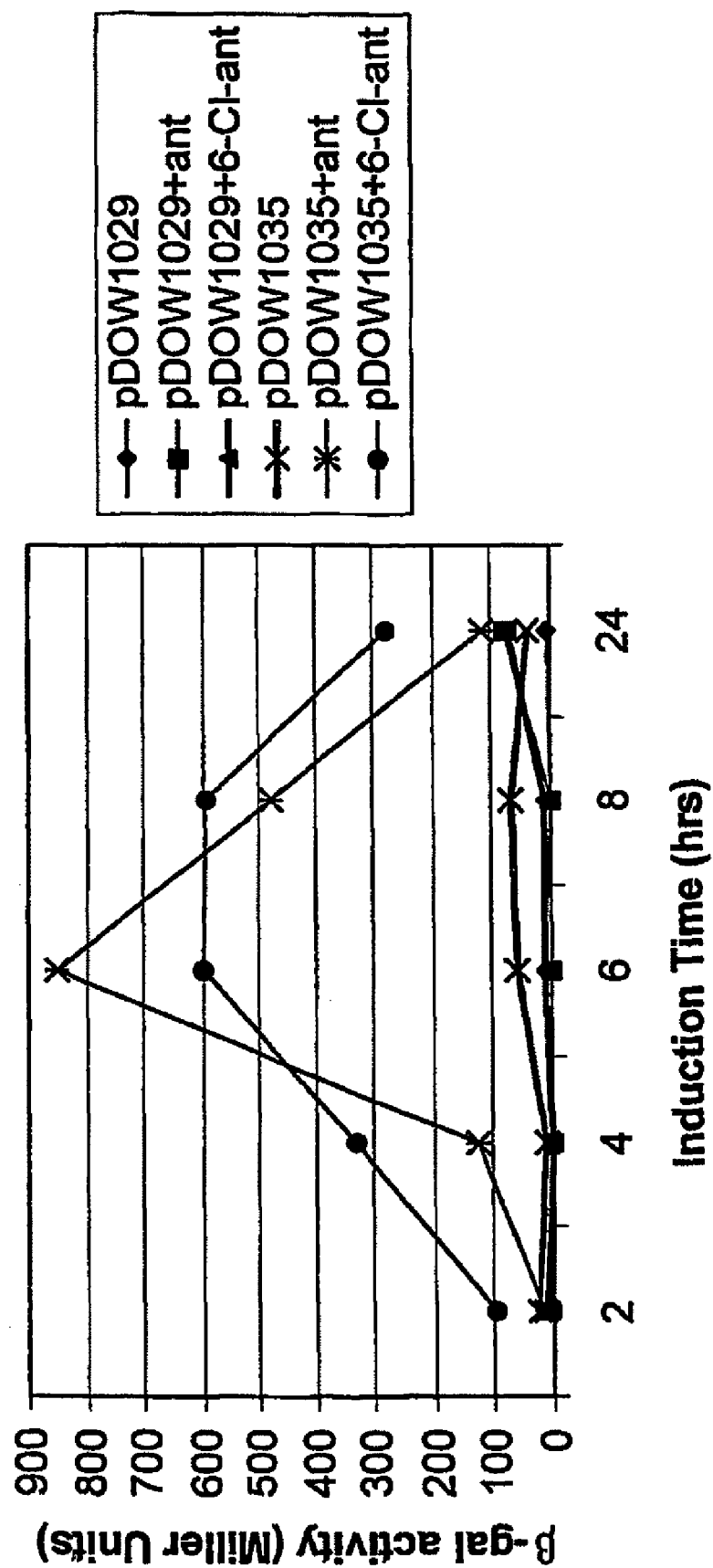
FIG. 8 presents a graph comparing the activity of a Pant713 construct (pDOW1029) versus an antR/Pant construct (pDOW1035), when induced with either 5 mM anthranilate or 2 mM 6-chloroanthranilate. In all constructs, the promoter was fused to a β-galactosidase-encoding sequence. The activity of the β-galactosidase reporter was followed over an 8 hour time course post-induction. The results show the activity of pDOW1035 following induction occurs much faster and is much higher than that of pDOW1029.

In addition, further increasing expression of the AntR has been found to result in more improved anthranilate-inducible expression by Pant promoters. For example, as shown in FIG. 8, both pDOW1029- and pDOW1035-constructs were induced in *P. fluorescens* host cells. FIG. 8 demonstrates a substantial difference in the rates of induction and the maximum levels of induction achieved for each of these promoters during the 24 hour time course of the study. pDOW1029 contains the Pant713 promoter, which lacks the antR coding sequence; pDOW1035 contains the full activator CDS. The *P. fluorescens* host cell used contains an actively expressed, chromosomal copy of the antR CDS. Thus, the results shown in FIG. 8 for pDOW1029 are for a system in which the antR gene is present in a single copy, while the results for pDOW1035 represent a two-copy system. These results demonstrate that the presence of an extra copy of the antR gene dramatically improves both the rate and level of response of the Pant promoter. Such improved expression can alternatively be obtained, or further enhanced, by driving antR expression with a very strong promoter. Improved induction/expression can also be obtained, as described below, by using a host cell in which a key gene (e.g., antA) responsible for degradation of the inducer compound (e.g., anthranilate) has been inactivated. Moreover, mutating the activator and/or promoter sequences (and selecting for mutants with increased activity) could also enhance the activator/promoter interaction and thereby allow for more improved anthranilate-inducible expression by Pant.

The anthranilate promoter was also found to be inducible by anthranilate analogs, including the halo-substituted anthranilic acid derivatives: 3-chloro-, 4-chloro-, 5-chloro- and 6-chloro-anthranilate. 6-chloroanthranilate is found to act as a gratuitous inducer of anthranilate metabolism, i.e. it is not metabolized by *P. fluorescens* yet induces expression from the anthranilate promoter. For example, 6-chloroanthranilate was found to induce the Pant713 and antR/Pant constructs (FIG. 8). Taken together, these results indicate that anthranilate itself induces the metabolic pathway; and that it is possible to utilize substituted anthranilate compounds as gratuitous inducers as an alternative to inactivating the anthranilate metabolic pathway of the host organism.

Example 3

Construction and Testing of a Fused, Pant-Pben Tandem Promoter

The relative strength of the Pant promoter with multi-copy antR was found to be approximately ⅕ that of the Pben278 promoter. However, unlike the catabolite-repressed Pben promoter, the activity of the Pant promoter was not inhibited during fermentation A fusion of these two promoters was created by linking them together, as shown in SEQ ID NO:3, i.e. by cloning a fragment antR and Pant, upstream of the Pben278 promoter fused to lacZ.

Figure 9A:
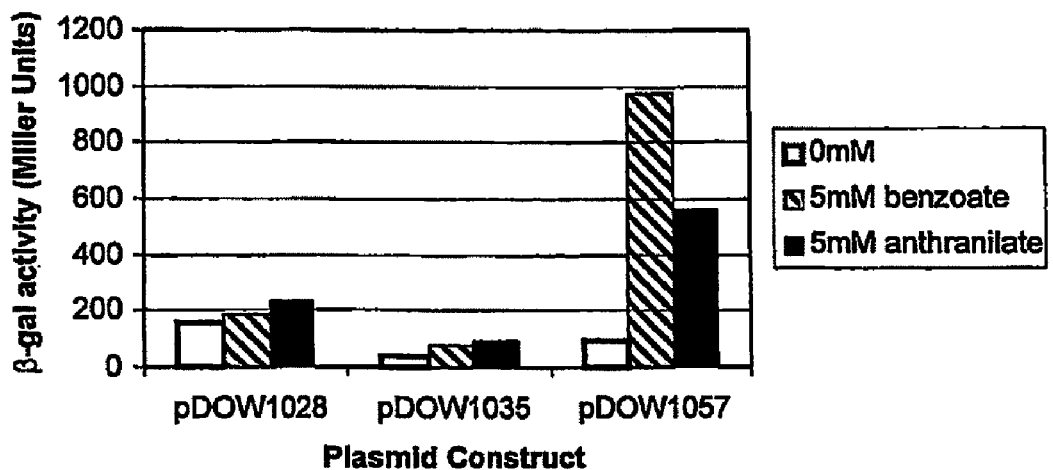
FIG. 9A presents results at 5 hours post-induction and FIG. 9B presents results at 24 hours post-induction.
Figure 9B:
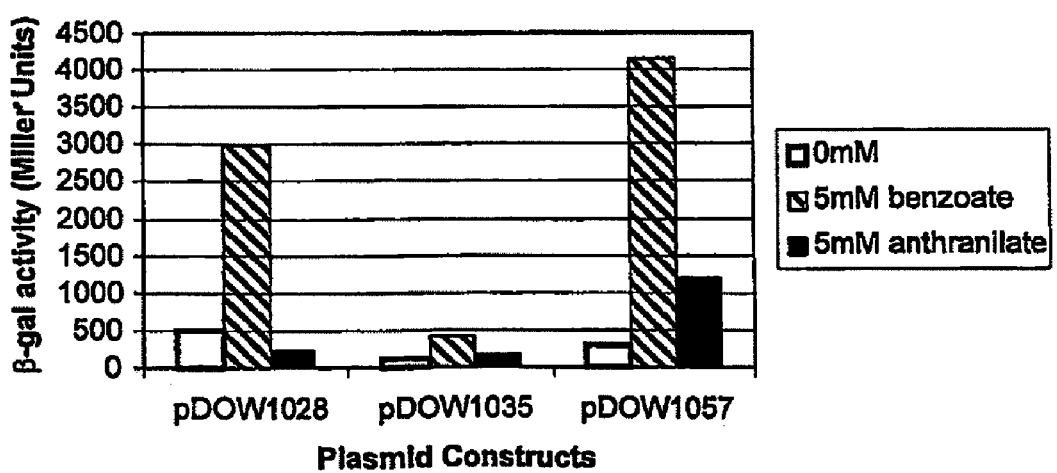

The strength of the tandem "'antR/Pant'-'Pben278'" construct, induced with anthranilate, was surprisingly found to be improved over that of "antR/Panf" alone upon induction with anthralate. The strength of the tandem promoter upon induction with benzoate was found to be similar to that of Pben278 alone (FIG. 9). The induction of greater β-galactosidase activity from the tandem promoter, upon addition of anthranilate in the presence of glucose, indicates that transcription from the tandem promoter, in which a natively catabolite-repressed Pben is located proximal to the coding sequence, surprisingly is not blocked by the catabolite repression of Pben. This is even more surprising in light of the fact that both (1) the bacterial source of the Pben and Pant elements in the tandem promoter and (2) the host cell in which induction was tested are the same: *Pseudomonas fluorescens* biotype A. Thus, even though the Pben element is native to the host cell, the upstream presence of the natively non-catabolite-repressed promoter (Pant) is able to overcome the catabolite repression of the natively catabolite-repressed promoter (Pben). Moreover, the presence of antR and Pant upstream of the Pben promoter appears to relieve the catabolite repression of Pben since the tandem promoter is active during fermentation, in the presence of glucose (see FIGS. 12 and 13).

Example 4

Improved Mutants of Pben509

Figure 10:
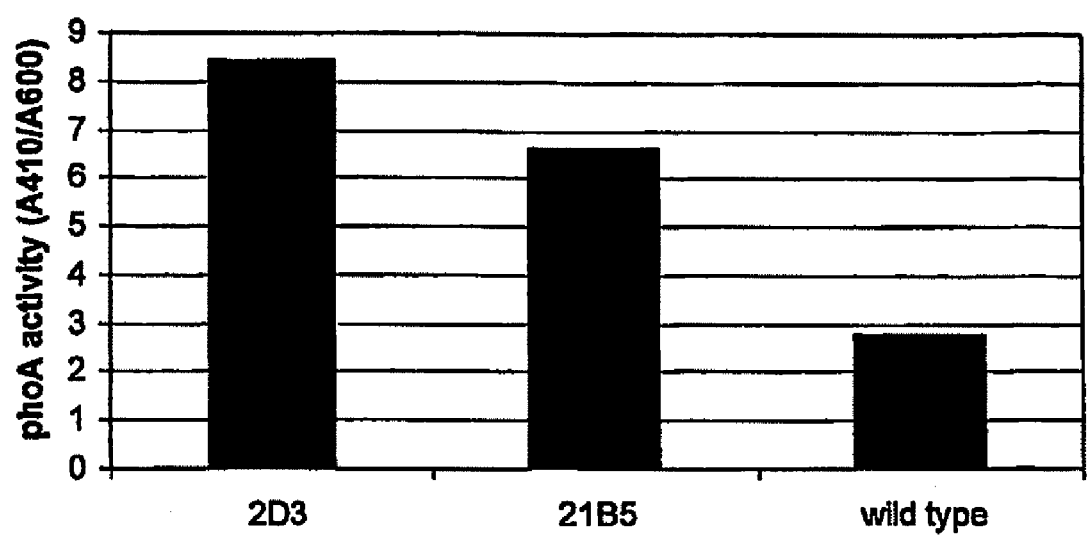
FIG. 10 presents a bar chart comparison of Pben509 activity to that of improved mutants 2d3 and 21b5, created by error prone PCR of Pben509. Expression constructs were formed by fusing promoter-containing fragments to a phoA reporter gene. Cultures containing the constructs were induced with 10 mM benzoate and alkaline phosphatase activity was measured at 24 hours post-induction.

In an effort to improve the Pben promoter, the Pben509 promoter was subjected to mutagenesis by error prone PCR. Mutants were screened for improved activity following induction with 10 mM benzoate at the shake flask scale. The mutants identified showed approximately 2-fold improvement over the wild type promoter (FIG. 10). Positive hits were re-transformed into *P. fluorescens* and re-tested to ensure that the improved activity was in fact due to the new construct.

Sequence analysis (FIG. 11) revealed one change in mutant 2d3 and two changes in mutant 21b5. As illustrated in the attached figure, the mutation in isolate 2d3 and one of the mutations in 21b5 fall within the coding region of the upstream ORF. This region is not contained within the Pben278 construct. The fact that these mutations were isolated in improved promoter mutants indicates that upstream regions may affect transcription, although they are not necessary for activated transcription. The second mutation identified in 21b5 is located five base pairs upstream of the transcriptional start site.

Example 5

Rationally Mutated Pben and Pant Promoters

Figure 14:
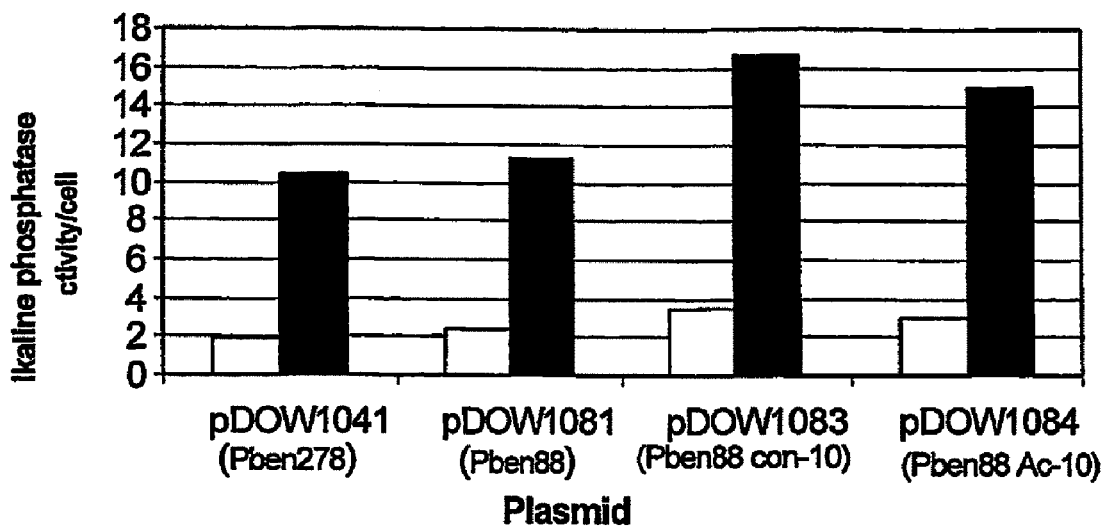
FIG. 14 presents a bar chart showing induction of Pben −10 mutants. The alkaline phosphatase activity of *P. fluorescens* containing the indicated Pben::phoA fusions is shown following 24-hour induction with 0 mM (□) or 5 mM (■) sodium benzoate. Representative experiment of triplicate samples is shown.

Construction and Analysis ofPben—10 Mutants. The native Pben predicted −10 region was mutated in an attempt to improve promoter activity. The promoter itself was truncated to 88 bp, and three derivatives of the $^-10$ were constructed: wild type (TACGGTT, SEQ ID NO:44, consensus (TATAAT, SEQ ID NO:45), and *Acinetobacter* (Ac) Pben-10 (TAAGGT, SEQ ID NO:46), as described in Materials and Methods. The primers were constructed such that one bp (G:C) upstream of the previously identified transcriptional start site was removed and 9 bp downstream of the previously identified transcriptional start site are included. These promoters were fused to the phoA reporter gene and tested for activity in *P. fluorescens* MB 101. FIG. 14 shows that the truncation of Pben promoter to 88 bp is sufficient to confer benzoate-activated expression, although altering the $^-10$ region either to the consensus TATAAT or to the $^-10$ sequence of the *Acinetobacter* Pben promoter did not appear to significantly improve benzoate induced promoter activity.

Figure 15:
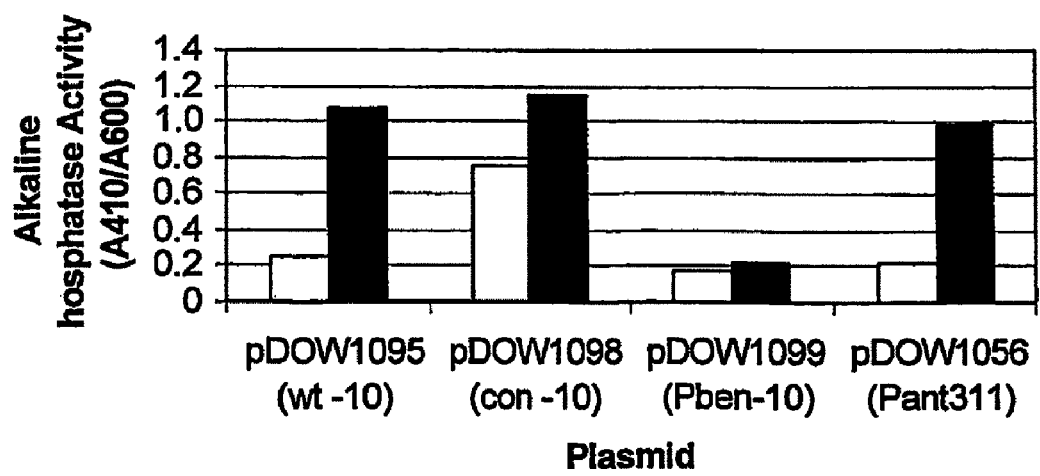
FIG. 15 presents a bar chart showing induction of Pant −10 mutants. The alkaline phosphatase activity of *P. fluorescens* antA::kanR containing the indicated Pant::phoA fusions is shown following 24-hour induction with 0 mM (D) or 5 mM (■) anthranilate. Representative experiment of triplicate samples is shown.

Construction and Analysis of Pant—10 Mutants. As described above for Pben, the predicted $^-10$ region of the Pant promoter was mutated in an attempt to improve promoter activity. In the construction of two Pant $^-10$ mutants, the promoter was truncated to 289 bp. DNA and fragments containing the anthranilate transcriptional activator and the mutant promoter were fused to the phoA reporter gene. The resulting plasmids were transformed into a derivative of MB 101 in which the antA gene has been insertionally inactivated. FIG. 15 shows that, following induction with anthranilate, the 3' truncation of the promoter to 289 bp did not affect activity (pDOW1095). Altering the putative $^-10$ region to consensus $^-10$ (pDOW1098) resulted in the promoter becoming capable of expression even in the absence of inducing compound. Addition of antlranilate did result in higher expression, indicating that the promoter was still inducible.

Example 6

Mutant Ptandem Promoters

The tandem promoter having the sequence as shown in pDOW1057 (SEQ ID NO:13) was mutated in the Pben−10 region as follows to construct mutant Ptandem promoters. A 1.6 kb DNA fragment containing antR and Pant, obtained by digestion of pDOW1039 with HindIII and SmaI, was gel purified (using QIAEX II gel column, from Qiagen Corp.) and ligated into each of pDOW1102 (Pben88wt-10), pDOW1106 (Pben88con-10), and pDOW1100 (Pben88Ac-10), each of which had been digested with HindIII and PmeI. Following transformation into host cells, positive clones were identified for each plasmid by colony PCR and then confirmed by DNA sequencing. The resulting plasmids were named pDOW1107, pDOW1108, and pDOW1109, respectively.

Figure 16A:
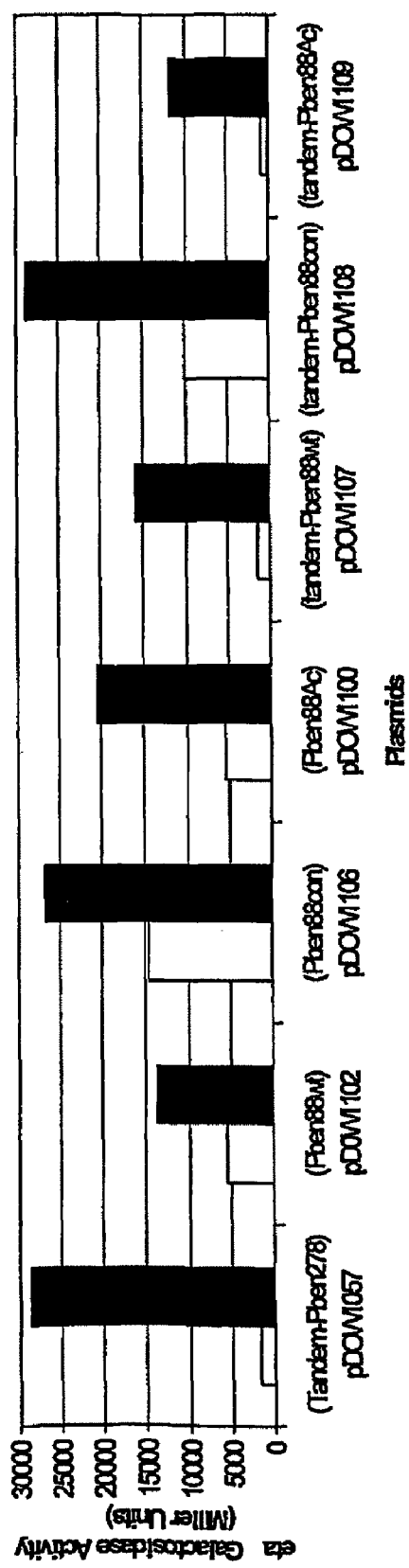
FIG. 16 presents bar charts indicating the effect of Pben88-10 mutations on the activity of the antR-Pant311-Pben tandem promoter. The β-galactosidase activity of *P. fluorescens* containing the indicated tandem promoter::lacZ fusions is shown following 24-hour induction with 0 mM (□) or 5 mM (■) sodium benzoate (FIG. 16A) or anthranilate (FIG. 16B). Representative experiment of triplicate samples is shown
Figure 16B:
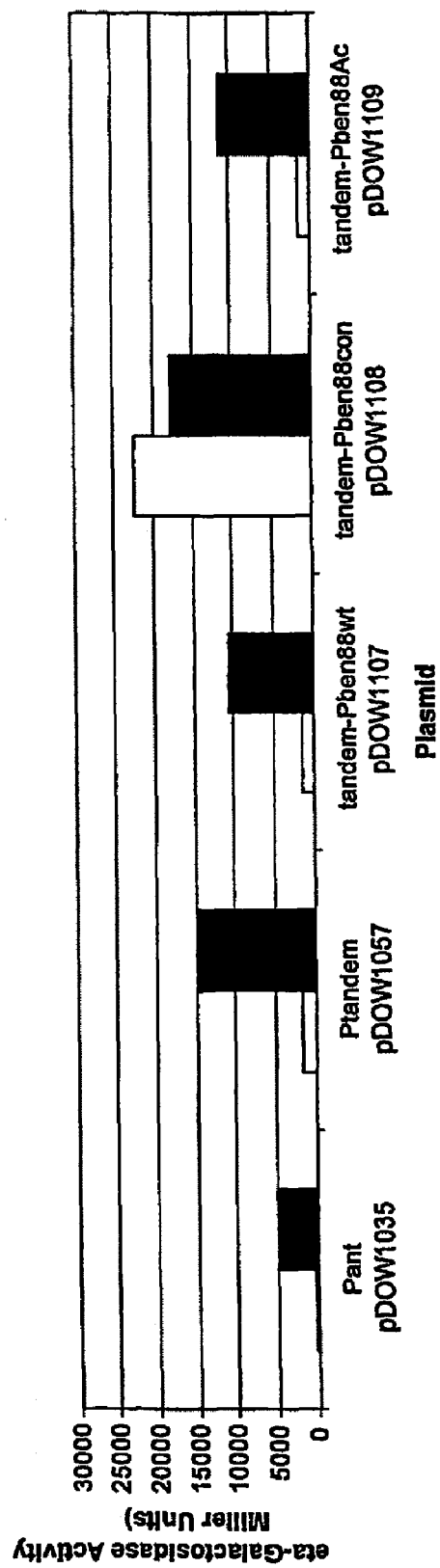

The effect of the Pben mutants on Ptandem activity was assessed at the shake flask scale. As shown in FIG. 16, the mutations did not have a significant effect on benzoate- or anthranilate-induced Ptandem activity. pDOW1107-1109 all showed β-galactosidase activity within 2 fold of that shown by the original construct, pDOW1057. One interesting finding was that the Pben88-10 consensus mutant alone or as part of a tandem promoter appeared to be expressed prior to induction with either benzoate or anthranilate. Addition of benzoate as an inducer resulted in an increased expression from Pben88−10 consensus alone (pDOW1 106), or as part of a tandem (pDOW1108) (FIG. 16A). However, addition of anthranilate did not result in an increase in lacZ expression from the Pben88-10 consensus tandem construct pDOW1108 (FIG. 16B).

Analysis of pDOW1108 at the 20 L scale revealed that MB101 carrying pDOW1108 induced with 2 mM or 5 mM benzoate pulses over a 24-hour period was not only active, but also was able to metabolize benzoate (data not shown). A relatively high level of β-galactosidase activity was detected at IQ, most likely a result of "leaky" expression, as had been detected at the shake flask scale (see FIG. 16A). An initial decrease in activity was consistently detected upon induction with benzoate, but activity then rose to a level greater than that detected at I0. Induction of pDOW1108 at the 20 L scale with 2 mM anthranilate every 4 hours for a 24-hour period showed that although anthranilate was metabolized efficiently, cloned tandem promoter expression as measured by β-galactosidase activity was leaky, as observed at shake flask scale, but actually declined after addition of anthranilate (see FIG. 18). A comparative induction of *P. fluorescens* carrying the original tandem promoter construct pDOW1057 with benzoate at the 20 L scale shows that benzoate is metabolized, as with pDOW1108. However, induction of β-galactosidase activity seems to be delayed compared to similar 2 mM dose inductions of the pDOW1108 construct, where increased activity was detected between 4 and 24 hours as opposed to between 30 and 48 hours post induction (data not shown).

Example 7

Use of Benzoate- and Anthranilate-Induced Promoters for Controlled Gene Expression during Fermentation Testing of the Pben509 lacZ fusion at the 20 L scale revealed transcriptional regulation issues not detected at the shake flask scale. Induction of the fusion with 5 or 10 mM benzoate was not consistently observed (data not shown). A correlation between benzoate consumption and activation of Pben509 was also observed. The presence of glucose is thought to be responsible for the inhibition of reporter gene expression. Subsequent to these experiments, it has been observed in shake flask experiments that metabolism of benzoate follows the depletion of glucose. The benzoate-inducible system may be useful in fermentation processes that utilize carbon sources other than glucose. Shake flask experiments reveal that the highest levels of induction are observed when citrate is used as a carbon source. This observation should hold true for fermentation scale.

Figure 12:
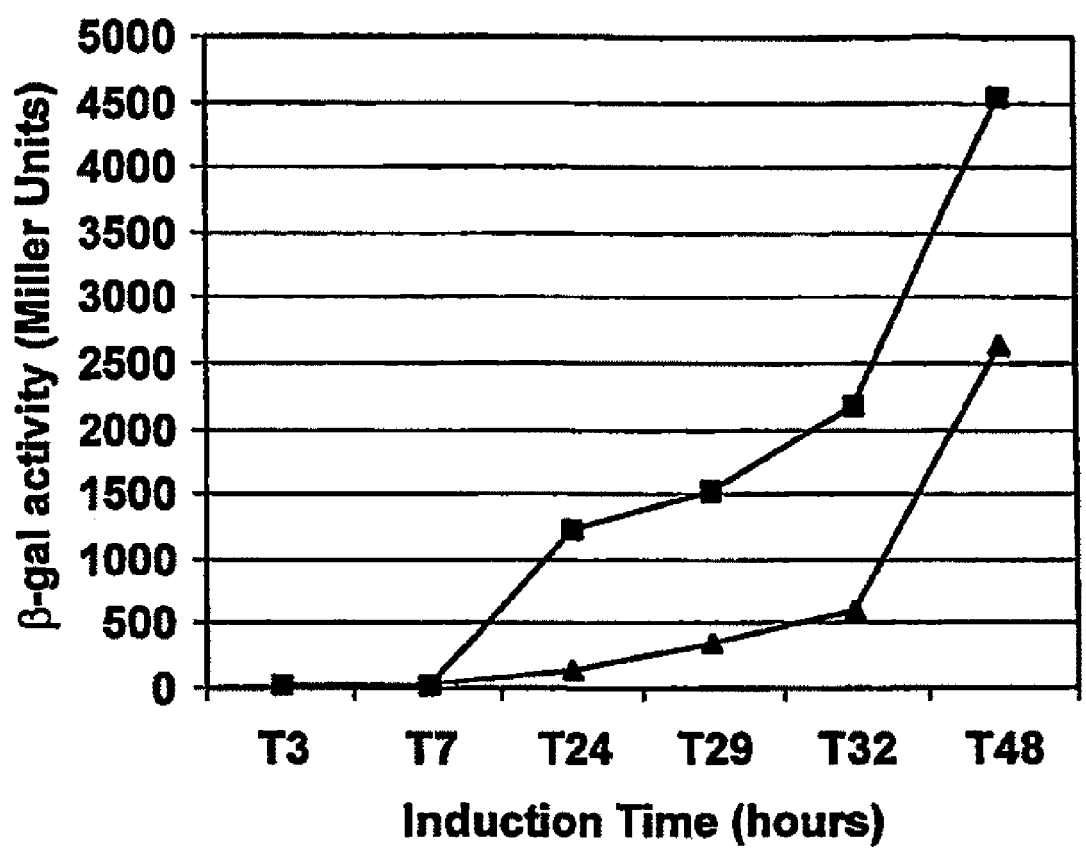
FIG. 12 presents a graph of anthranilate-induced expression in 20 L fermentation conditions. An antR/Pant construct pDOW1035 (■) and a tandem promoter construct pDOW1057 (▲) were induced with 5 mM sodium anthranilate plus a 1 mM/hour anthranilate feed. The activity level for each 20 L fermentation run is shown.
Figure 13A:
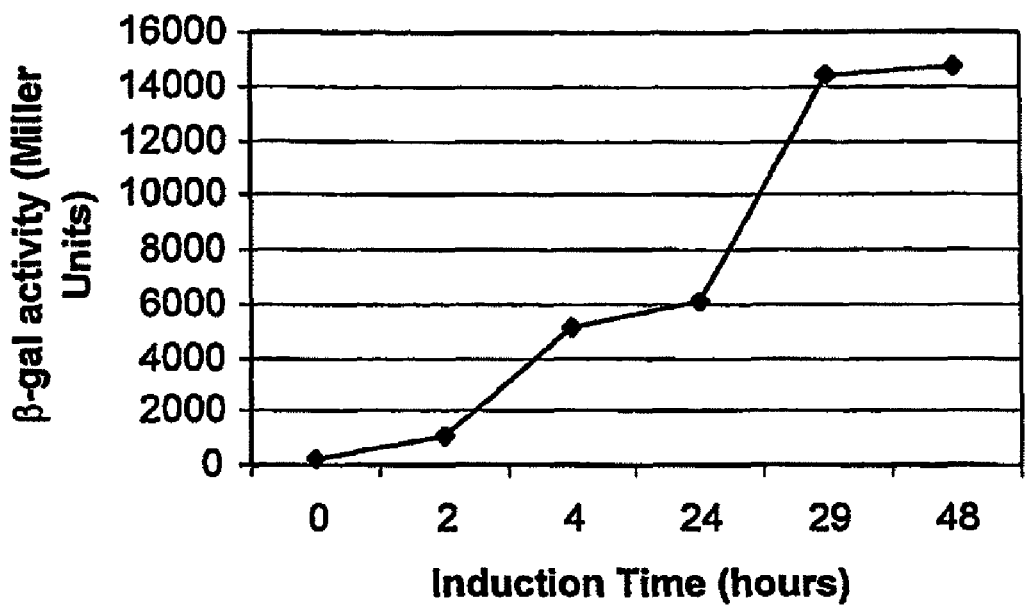
FIG. 13A presents the activity of β-galactosidase expressed from the reporter gene construct.
Figure 13B:
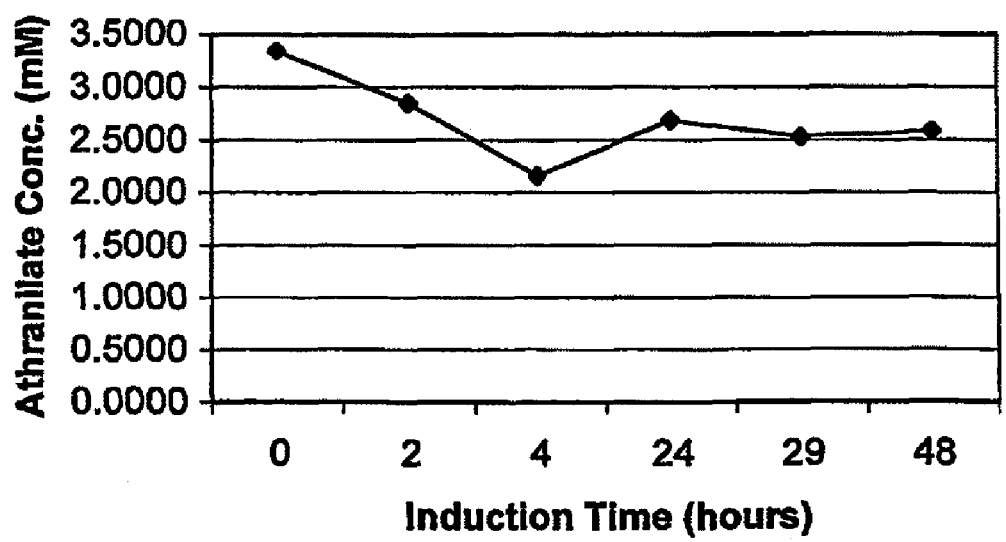
FIG. 13B shows the maintenance of anthranilate concentration, demonstrating that the knockout host cell does not metabolize anthranilate.

Testing of the antR Pant construct and of the tandem promoter construct at the 20 L scale showed activity similar to that observed at the shake flask scale. Because the inducer is consumed by the culture, anthranilate was fed during the course of induction. Activity was observed to increase over time. It is likely that higher activity will be observed in strains that are unable to metabolize the inducer. As observed in shake flask and 20 L fermentation experiments, the tandem promoter construct is more active than the antR Pant construct (FIG. 12). Inactivation of anthranilate metabolism by insertional inactivation of the antA gene allowed for greater expression of the tandem promoter:lacZ fusion at the 20 L scale. As shown in FIG. 13, anthranilate is not metabolized during the course of induction, and the level of β-galactosidase activity observe is much higher that that observed in a strain that does metabolize anthranilate.

Example 8

Characterization of the BenAB Knock-Out Strain

Figure 19:
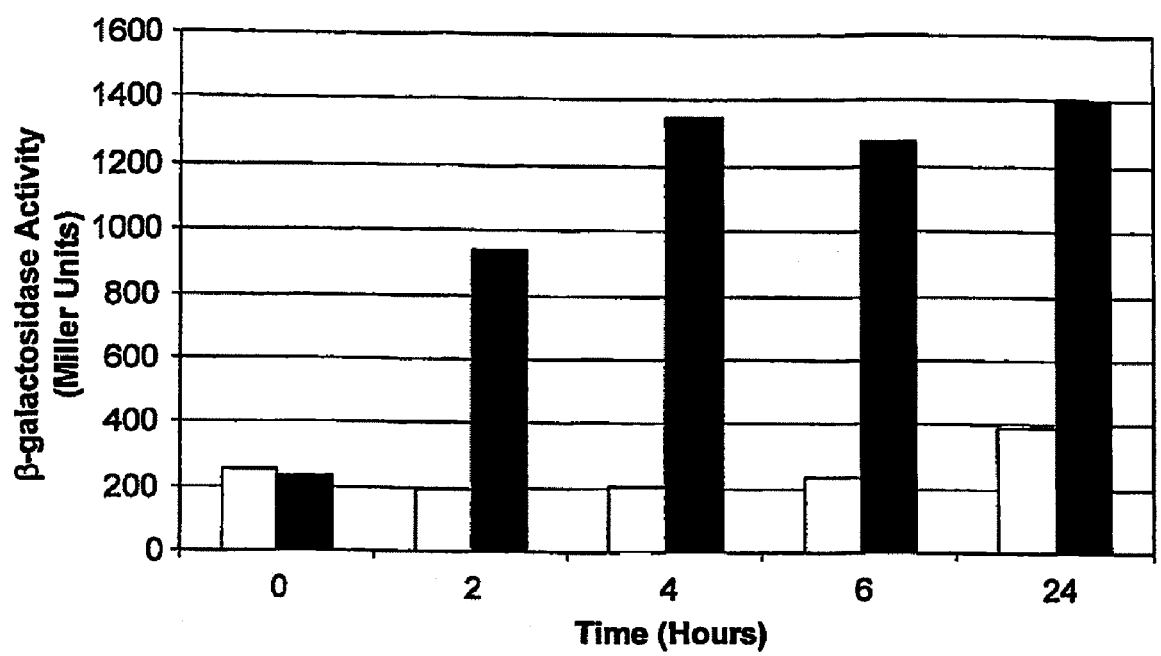
FIG. 19 presents a bar chart demonstrating an analysis of Pben activity in the benAB knock-out strain. β-galactosidase activity of a *P. fluorescens* MB101 benAB knock-out strain carrying pDOW1019 (Pben278::lacZ) is shown as a result of induction with either 0 mM (□) or 5 mM (■) sodium benzoate for up to 24 hours. Cells were grown in LB medium.

To verify whether benzoate is in fact the inducer of the Pben promoter, and not a downstream metabolite thereof, the benAB gene knock-out strain of *P. fluorescens* was further characterized. The benA and benB genes code for the large and small subunits of benzoate 1, 2 dioxygenase, respectively. Two isolated of the benAB knock-out strain were further tested for the ability to metabolize benzoate as follows. Cells were grown in LB-proline-uracil to high density; benzoate was then added to the cultures to a final concentration of ~5 mM before they were returned to incubate for 24 hr. The concentration of benzoate remaining in the cell-free broth, as measured by HPLC, showed that the benAB deletion mutants were unable to metabolize benzoate, while the parent, non-knock-out strain did metabolize benzoate efficiently. To assess whether the Pben promoter is still active in the benAB knockout strain, a plasmid containing a Pben278::lacZ construct was transformed into one of the strains, and transformants were grown in LB medium. Transformants were induced with 0 or 5 mM benzoate and lacZ activity demonstrated that benzoate was indeed the inducer for Pben, rather than a downstream metabolite. See FIG. 19.

Example 9

Effect of Multi-Copy Expression of BenR

A DNA fragment containing the BenR ORF upstream of benA along with Pben promoter was amplified from *P. fluorescens* MB214 genomic DNA using primers Benact5' and Bambenconshort under the following conditions: 94° C. for 1 min; (94° C., 1 min; 50° C., 30 sec; 72° C., 90 sec) for 30 cycles; then 72° C. for 10 min, and 4° C. hold. The PCR product was ligated into the pCR2.1 vector, and the sequence verified. The insert fragment was digested with PmeI and BamHI, and ligated to pDOW1033. The resulting plasmid was stocked as pDOW1090. The same promoter construct was fused to the lacZ reporter by digesting pDOW1090 with BamHI and XhoI to remove the phoA reporter, and replacing it with the 3 Kb BamI-HXhoI fragment of pDOW1035, containing the lacZ reporter gene.

Figure 17:
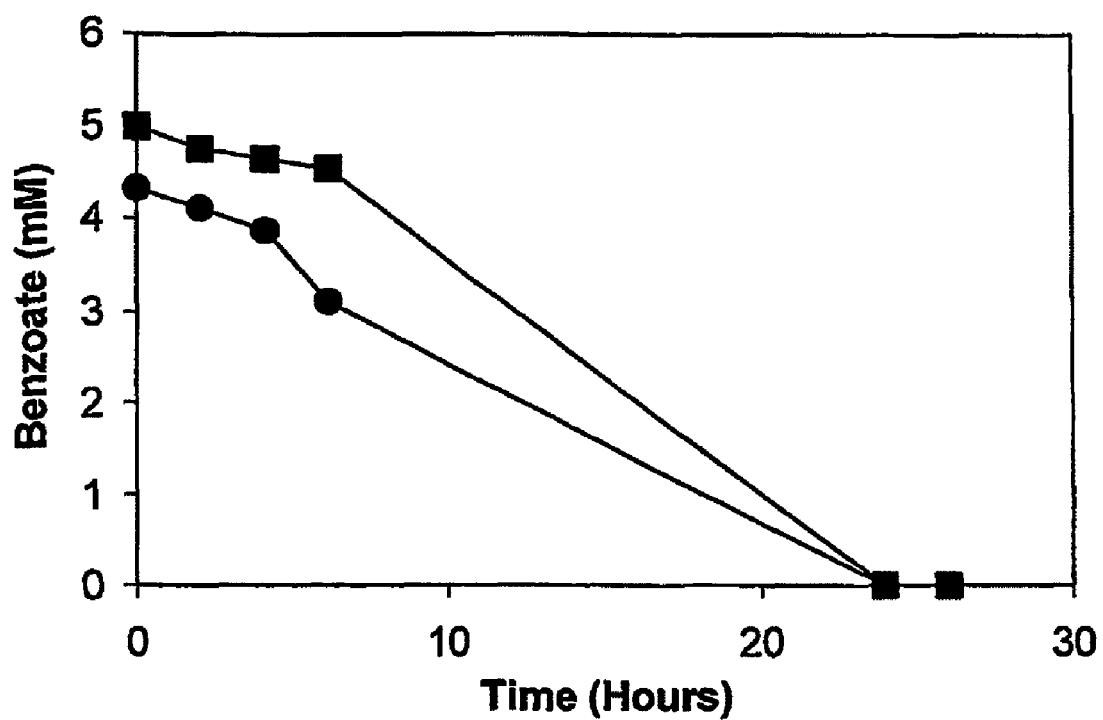
FIG. 17 presents a graph of benzoate consumption during 20 L fermentation when benR is present in multicopy with pDOW1090. Data shown are HPLC analyses measuring the concentration of benzoate throughout the induction of two 20 L fermentors in duplicate fermentations, labeled run "030211I" (●) and run "030211K" (■). The cultures were induced with 5 mM sodium benzoate.
Figure 18A:
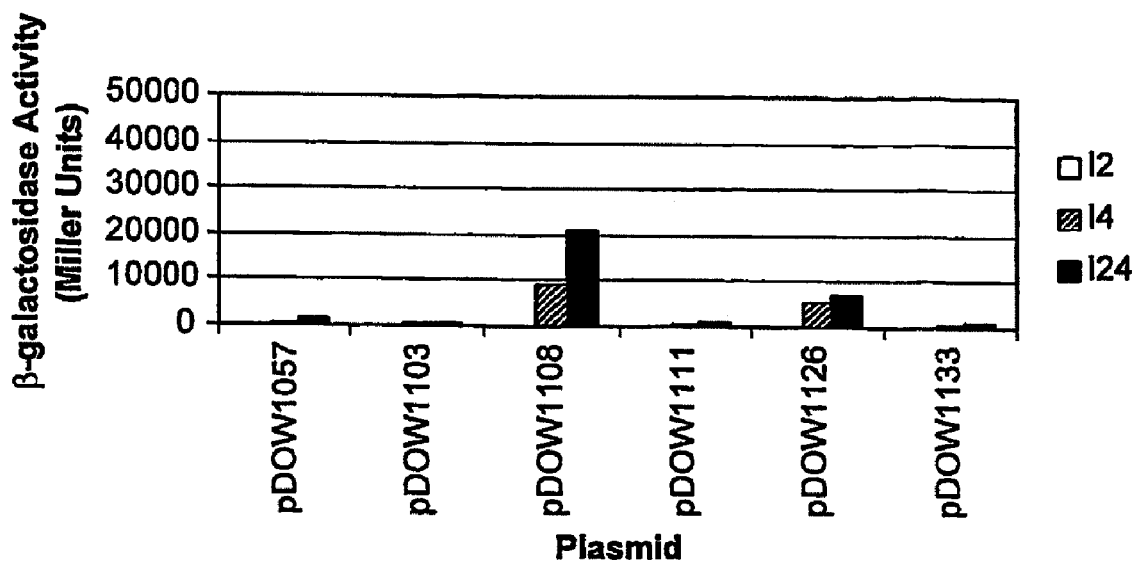
FIG. 18 presents bar chart comparisons of tandem promoter construct activity. The β-galactosidase activity of *P. fluorescens* containing the indicated tandem promoter::lacZ fusions (except for pDOW1035, which is ant activator-Pant311::lacZ; and pDOW1126, which is ben activator Pben88⁻10consensus::lacZ) is shown following induction with 0 or 5 mM sodium benzoate (FIGS. 18A and 18B for 2, 4, and 24 hour time-points) or anthranilate (FIGS. 18C and 18D, for 0, 2, 6, and 24 hour time-points). Representative experiment of triplicate samples is shown. Time points are indicated as "post-induction" by the letter "I".
Figure 18B:
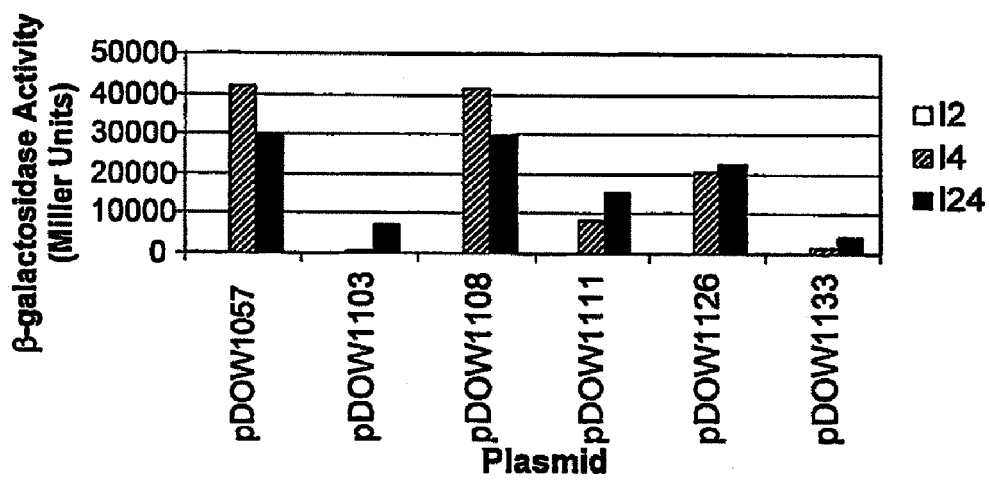
Figure 18C:
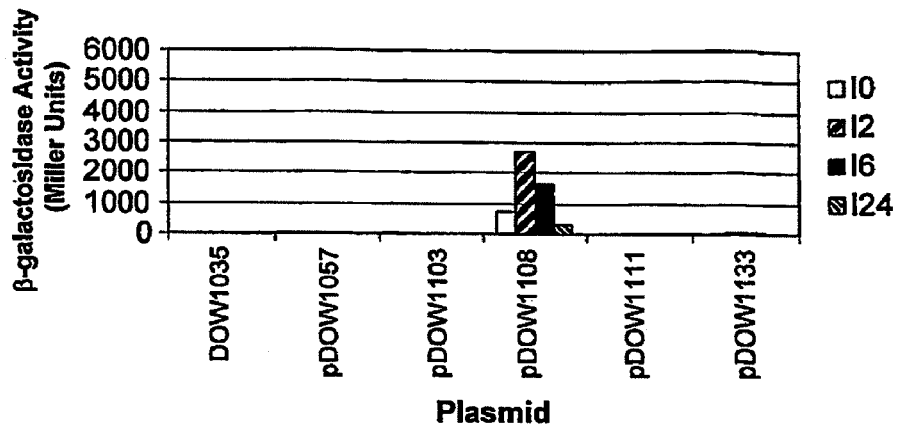
Figure 18D:
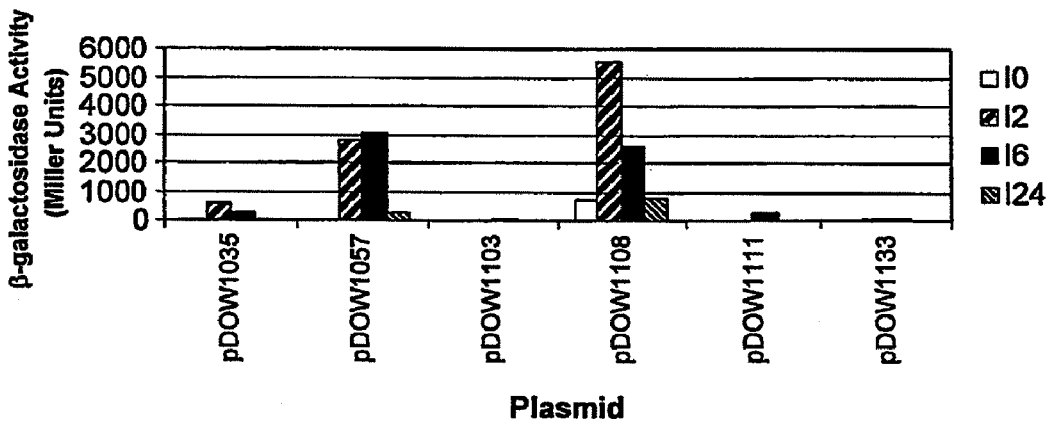

The benR ORF was cloned together with the Pben promoter upstream of the phoA reporter gene to determine whether expression of the transcriptional activator gene in multicopy would improve benzoate activated gene expression. At the shake flask scale, there was observed no significant difference in promoter activity with benR in multicopy. Since it has been shown in the literature that overexpressing the transcriptional activator can overcome catabolite repression, we tested 20 L fermentations of *P. fluorscens* MB 101 carrying pDOW1090. Previous studies showed that MB101 carrying a Pben::lacZ fusion was unable to metabolize benzoate during fermentation with a corn syrup feed. We found that MB101 carrying pDOW1090 is able to metabolize benzoate at the 20 L scale. Benzoate was found to be consistently metabolized in triplicate 20 L fermentations, indicating that the chromosomal Pben promoter was active. Thus, the presence of multi-copy expression of BenR overcame catabolite repression. See FIG. 17.

As a result, we have found that overexpression of benR allows *P. fluorescens* to overcome catabolite repression observed for benzoate metabolism at the 20 L scale when constructs containing Pben alone were tested. Demonstration of benzoate-induced promoter activity at the 20 L scale is an important improvement, since benzoate-induced activation of tandem promoters is greater that that of anthranilate-induced activity at the shake flask scale, even though anthranilate-induced activity under control of Ptandem is already stronger than anthranilate-induced activity of Pant. Both pDOW1057 and pDOW1108 were found to be benzoate-inducible at the 20 L scale. Although the pDOW1108 construct is "leaky", in that significant expression occurs prior to addition of the inducer, this should not present a large problem for its use in protein expression. In addition, because it has been found that Pben is active in the benAB knock-out strain, use of such a knock-out strain will improve benzoate-induced promoter activity for Pben, as well as Ptandem. Likewise, because it has now been shown that induction of the tandem promoter construct pDOW1057 with anthranilate is improved in a strain carrying and insertionally inactivated chromosomal ant4 gene, improved anthranilate-induced promoter activity will be enhanced for Pant, as well as Ptandem.

Consequently, anthranilate- and benzoate-inducible promoters have now been developed for use in bacterial expression systems. These promoters have been found to permit tight regulation of transcription and are inducible with low-cost compounds such as benzoate and anthranilate; the presence of antR in multi-copy also now has been found to significantly improve the activity of the Pant promoter. In addition a new type of tandem promoters has now been developed for use in bacterial expression systems, exemplified by Pant-Pben tandem promoters that have been found to exhibit increased levels of anthranilate-induced gene expression, over Pant itself; were found to be benzoate-inducible, i.e. to the same level as Pben itself; and were found to surprisingly overcome the catabolite repression to which Pben alone was subject. Further, the present work has demonstrated that both the Pant promoter (with antR) and the tandem promoter constructs exhibit anthnnilate-inducible gene expression under fermentation-scale conditions (e.g., at the 20 L scale); the tandem promoter constructs also exhibits benzoate inducible gene expresion under fermentations-scale condiitons.

It is to be understood that the preferred embodiments described above are merely exemplary of the present invention and that the terminology used therein is employed solely for the purpose of illustrating these preferred embodiments; thus, the preferred embodiments selected for the above description are not intended to limit the scope of the present invention. The invention being thus described, other embodiments, alternatives, variations, and obvious alterations will be apparent to those skilled in the art, using no more than routine experimentation, as equivalents to those preferred embodiments, methodologies, protocols, vectors, reagents, elements, and combinations particularly described herein. Such equivalents are to be considered within the scope of the present invention and are not to be regarded as a departure from the spirit and scope of the present invention. AlR such equivalents are intended to be included within the scope of the following claims, the true scope of the invention thus being defined by the following claims.

REFERENCES

1. J. Brosius & A. Holy, Regulation of ribosomal RNA promoters with a synthetic lac operator, *Proc. Nat'l Acad Sci. USA*, 81:6929-6933 (1984).
2. E. Amann et al., Vectors bearing hybrid trp-lac promoter useful for regulated expression of cloned genes in *Escherichia coli*, *Genes* 25:167-178 (1983).
3. J. Sanchez-Romero & V. De Lorenzo, Genetic Engineering of Nonpathogenic *Pseudomonas* strains as Biocatalysts for Industrial and Environmental Processes, in *Manual of Industrial Microbiology and Biotechnology* (A. Demain & J. Davies, eds.) pp.460-74 (1999) (ASM Press, Washington, D.C.).
4. H. Schweizer, Vectors to express foreign genes and techniques to monitor gene expression for Pseudomonads, *Current Opinion in Biotechnology*, 12:439-445 (2001).
5. R. Slater & R. Williams, The Expression of Foreign DNA in Bacteria, in *Molecular Biology and Biotechnology* (J. Walker & R. Rapley, eds.) pp.125-54 (2000) (The Royal Society of Chemistry, Cambridge, UK).
6. D. Goeddel et al., Direct expression in *Escherichia coli* of a DNA sequence coding for human growth hormone, *Nature* 281:544-48 (1979).
7. K. L. Hester et al., Catabolite repression control by crc in 2×YT medium is mediated by post-transcriptional regulation of bkdR expression in *Pseudomonas putida*, *J. Bacteriol.* 182(4): 1150-53 (2000).
8. P. M. Santos et al., Physiological analysis of the expression of the styrene degradation gene cluster in *Pseudomonas fluorescens* ST, *Appl. & Environ Microbiol.* 66(4):1305-10 (2000).
9. W. A. Duetz et al., Catabolite repression of the toluene degradation pathway in *Pseudomonas putida* harboring pWW0 under various conditions of nutrient limitation in chemostat culture, *Appl. & Environ Microbiol.* 62(2):601-06 (1996).
10. M. M. Marin et al., The alkane hydroxylase gene of *Burkholderia cepacia* RR10 is under catabolite repression control, *J Bacteriol.* 183(14):4202-09 (2001).
11. M. M. Ochs et al., Amino acid-mediated induction of the basic amino acid-specific outer membrane porin OprD from *Pseudomonas aeruginosa*, *J. Bacteriol.* 181(17):5426-32 (1999).
12. T. Nishijyo et al., Molecular characterization and regulation of an operon encoding a system for transport of arginine and ornithine and the ArgR regulatory protein in *Pseudomonas aeruginosa*, *J. Bacteriol.* 180(21):5559-66 (1998).
13. K. L. Hester et al., Crc is involved in catabolite repression control of the bkd operons of *Pseudomonas putida* and *Pseudomonas aeruginosa*, *J. Bacteriol.* 182(4): 114449 (2000).
14. G. Mosqueda & J. L. Ramos, A set of genes encoding a second toluene efflux system in *Pseudomonas putida* DOT-TlE is linked to the tod genes for toluene metabolism, *J. Bacteriol.* 182(4):937-43 (2000).
15. C. D. Lu & A. T. Abdelal, The gdhb gene of *Pseudomonas aeruginosa* encodes an arginine-inducible NAD(+)-dependent glutamate dehydrogenase which is subject to allosteric regulation, *J. Bacteriol.* 183(2):490-99 (2001).
16. S. Vilchez et al., Control of expression of divergent *Pseudomonas putida* put promoters for proline catabolism. *Appl. & Environ Microbiol.* 66(12):5221-25 (2000).

---

The invention claimed is:

1. A nucleic acid construct comprising two non-identical promoters in a tandem arrangement, wherein each promoter is responsive to an exogenously supplied compound, wherein the upstream promoter is set forth in nucleotides 1329-1369 of SEQ ID NO:13, wherein the downstream promoter in the tandem arrangement is the catabolite-repressed promoter set forth in nucleotides 1477-1509 of SEQ ID NO:13, and wherein induction of the upstream promoter in the tandem arrangement overcomes the catabolite repression of the downstream promoter.

2. The construct of claim 1 further comprising at least one activator protein binding site.

3. The construct of claim 2 wherein said at least one activator protein binding site is a benzoate activator protein binding site or an anthranilate activator protein binding site.

4. The construct of claim 1 further comprising a nucleotide sequence encoding a transgene of interest.

5. The construct of claim 4 wherein the transgene of interest is operably linked to the catabolite-repressed promoter.

6. A host cell comprising a nucleic acid construct comprising two non-identical promoters in a tandem arrangement, wherein each promoter is responsive to an exogenously supplied compound, wherein the upstream promoter is set forth in nucleotides 1329-1369 of SEQ ID NO:13, wherein the downstream promoter in the tandem arrangement is the catabolite-repressed promoter set forth in nucleotides 1477-1509 of SEQ ID NO:13, and wherein induction of the upstream promoter in the tandem arrangement overcomes the catabolite repression of the downstream promoter.

7. The host cell of claim 6, wherein the construct further comprises a transgene of interest.

8. The host cell of claim 6, wherein the construct further comprises at least one benzoate activator protein binding site and at least one anthranilate activator protein binding site.

9. A process for protein expression comprising growing in the presence of an inducing condition a cell comprising a nucleic acid construct comprising two non-identical promoters in a tandem arrangement, wherein the upstream promoter is set forth in nucleotides 1329-1369 of SEQ ID NO:13, wherein the downstream promoter in the tandem arrangement is the catabolite-repressed promoter set forth in nucleotides 1477-1509 of SEQ ID NO:13, wherein induction of the upstream promoter in the tandem arrangement overcomes the catabolite repression of the downstream promoter, and wherein said construct further comprises a transgene of interest.

10. The process of claim 9 wherein the presence of an inducing condition results in the production of a recombinant protein or peptide encoded by said transgene of interest.

11. The process of claim 9 wherein the inducing condition comprises the presence of anthranilate.

12. The process of claim 11 wherein the inducing condition further comprises the presence of benzoate.

13. The process of claim 9 wherein induction of the upstream promoter overcomes the catabolite repression of the downstream catabolite repressed promoter.

14. The process of claim 10 further comprising isolating the recombinant protein or peptide.

\* \* \* \* \*

SEQUENCE LISTING

```
<160> NUMBER OF SEQ ID NOS: 46

<210> SEQ ID NO 1
<211> LENGTH: 5006
<212> TYPE: DNA
<213> ORGANISM: Pseudomonas fluorescens
<220> FEATURE:
<221> NAME/KEY: misc_feature
<222> LOCATION: (1)...(5006)
<223> OTHER INFORMATION: Benzoate Operon controlling expression of
      benABCD
<220> FEATURE:
<221> NAME/KEY: CDS
<222> LOCATION: (225)...(284)
<223> OTHER INFORMATION: Alternative amino-terminal-portion-encoding
      CDS,starting from alternative putative initator codon (ttg225-227)
      of CDS encoding BenR, giving Met1->Arg335 as the amino acid
      sequence of the Pben activator protein
<220> FEATURE:
<221> NAME/KEY: CDS
<222> LOCATION: (285)...(1229)
```

```
<223> OTHER INFORMATION: Sense strand of ORF encoding the putative Pben
      activator protein, starting from putative initiator codon
      (atg285-287) of CDS encoding BenR,giving Met21->Arg335 as the full
      amino acid sequence of the Pben activator protein
<220> FEATURE:
<221> NAME/KEY: mutation
<222> LOCATION: 679..679
<223> OTHER INFORMATION: An expressed mutation of g679->a679, changing
      agc->aac and giving Ser152->Asn152 upon expression
<220> FEATURE:
<221> NAME/KEY: misc_feature
<222> LOCATION: 1106..1106
<223> OTHER INFORMATION: A mutation of a1106->t1106, found in Pben509
      mutant 2d3
<220> FEATURE:
<221> NAME/KEY: misc_feature
<222> LOCATION: 1223...1223
<223> OTHER INFORMATION: A mutation of c1223->t1223, found in Pben509
      mutant 21b5
<220> FEATURE:
<221> NAME/KEY: misc_signal
<222> LOCATION: (1228)...(1274)
<223> OTHER INFORMATION: Approximate region estimated to contain the
      BenR binding site
<220> FEATURE:
<221> NAME/KEY: promoter
<222> LOCATION: (1275)...(1307)
<223> OTHER INFORMATION: Putative promoter (Pben) from benzoate operon
      (benABCD)
<220> FEATURE:
<221> NAME/KEY: -35_signal
<222> LOCATION: (1275)...(1280)
<223> OTHER INFORMATION: Putative -35 region of Pben promoter
<220> FEATURE:
<221> NAME/KEY: -10_signal
<222> LOCATION: (1296)...(1301)
<223> OTHER INFORMATION: Putative -10 region of Pben promoter
<220> FEATURE:
<221> NAME/KEY: misc_feature
<222> LOCATION: 1296..1301
<223> OTHER INFORMATION: Substitution mutation of Pben -10 region by
      tataat to form -10con mutants,and by taaggt to form -10benAc
      mutants
<220> FEATURE:
<221> NAME/KEY: misc_feature
<222> LOCATION: (1302)...(1302)
<223> OTHER INFORMATION: A mutation of g1302->a1302, found in Pben509
      mutant 21b5
<220> FEATURE:
<221> NAME/KEY: misc_feature
<222> LOCATION: (1306)...(1306)
<223> OTHER INFORMATION: A deletion of g1306 found in mutant promoter
      variants herein
<220> FEATURE:
<221> NAME/KEY: misc_signal
<222> LOCATION: (1307)...(1307)
<223> OTHER INFORMATION: Putative transcription start site under control
      of Pben
<220> FEATURE:
<221> NAME/KEY: misc_signal
<222> LOCATION: (1340)...(1342)
<223> OTHER INFORMATION: Putative native translation initiator codon
<220> FEATURE:
<221> NAME/KEY: CDS
<222> LOCATION: (1340)...(2713)
<223> OTHER INFORMATION: BenA open reading frame encoding benzoate
      1,2-dioxygenase alpha subunit
<220> FEATURE:
<221> NAME/KEY: misc_signal
<222> LOCATION: (2714)...(2716)
<223> OTHER INFORMATION: BenA stop codon
<220> FEATURE:
<221> NAME/KEY: CDS
<222> LOCATION: (2713)...(3198)
<223> OTHER INFORMATION: BenB open reading frame encoding benzoate
      1,2-dioxygenase beta subunit
<220> FEATURE:
<221> NAME/KEY: misc_signal
<222> LOCATION: (3199)...(3201)
```

```
<223> OTHER INFORMATION: BenB stop codon
<220> FEATURE:
<221> NAME/KEY: CDS
<222> LOCATION: (3212)...(4231)
<223> OTHER INFORMATION: BenC open reading frame encoding benzoate
      1,2-dioxygenase electron
<220> FEATURE:
<221> NAME/KEY: misc_signal
<222> LOCATION: 4232..4234
<223> OTHER INFORMATION: BenC stop codon
<220> FEATURE:
<221> NAME/KEY: CDS
<222> LOCATION: (4224)...(5003)
<223> OTHER INFORMATION: BenD open reading frame encoding
      cis-1,2-dihydroxycyclohexa-3,5-diene-1-carboxylate dehydrogenase
<220> FEATURE:
<221> NAME/KEY: misc_signal
<222> LOCATION: 5004..5006
<223> OTHER INFORMATION: BenD stop codon

<400> SEQUENCE: 1
gcatgacgtt gttgatttct catcgattct ccagcgtgcg caatgccgac cacatcatcg      60
tgctggacgg cgggcgaatc ctggaggagg gcagtcatca ccaactgatg gcggcgggtg     120
gacgctatgc cgagttgttc gatgttcagg cgcggggta  tcgctaggtc ccagcgccca     180
cgcccgacga tacctccagg gtatccctcc agactttatc catattggac gcccccctac     240
ccaagcgtca gcctgagccc aataacgata aagagtcgc  gaccatgacc gtgctattga     300
gtgagcgcag ccagattttc cagggcgccg atgcctacgc ggtgtcggac tacgtcaacc     360
agcatgtggg cagccactgc attcgcctgc ctcccagggg ccagcccgg  gcaagtatca     420 gccatcgcac cttcgccagc ctggacctgt gccgcatcag ctacggcgca ccggtgcggg     480
tcacgtcggt ggcgctggag accatctacc acctgcagat cctcttgagc gggcattgcc     540
gctccaactc ccgtggcgag gatgatgtgt tcgggccggg ggaaatcctg ctgatcaatc     600
cggacgaccc ggtagacctg acctattccg ccgactgcga aaaattcatc atcaaactgc     660
cggtgcgcct gctggaaagc gcctgcctgg agcagcactg gagcctgccg cgggcggggg     720
tccgcttcac gacggcccgc cacgcgctca gtgaaatggg cggcttcctg ccgttgctcg     780
ggttgatctg ccatgaggcg gaaaacgctg ccgagcccca catgcaaggc ctgtacgaac     840
gcatcgtggc caacaagctg ctggcattgc tgggcagcaa tgtgtcgcgg gtgaccccccc     900 gggctgccca cggcggtggg tttgaagcgg tgcacgaatt tatccagcag cacctgggcg     960
atgacatcag cgtcgagcag ttgatggccg tggccaacgt cagtgaacgt tcgctgtaca    1020
gcctgtttga gcgccaggtg gggctgtcgc gcgcgattac gtatgccgc  tgcaagctcg    1080 aacgcgtaca tgcacgcttg caactaagca gcacgcgcag cgtgaccgag gtggctttgg    1140
accatgggtt catgcaccta gggcggtttt ccgaagccta tcgcaaacgc ttcggcgaac    1200
tgccgtcgca gacctggaaa cgccatcgtt aagcgacgtg cgcctggcgg atagcgatgt    1260
gcaggcagcg gatattgacg ggcagggcga gcacgtacgg tgagggcgcc tgatacaaga    1320
acaacggagg gcccgcccca tgatcagtac acccgaccga ctcgcctgcc aattgcgcga    1380
gtccgtacag gaagaccccg ccactggggt gttccgctgc cgcgcgaca  tcttcaccga    1440 ccccgacctg tttgccctgg agatgaaaca catcttcgaa ggcgggtgga tctacctggc    1500
ccatgaaagc caggtgccgc agatcaacga ttacttcacc acctggatcg ccgccagcc    1560 ggtggtcatc acccgtgaca agcacggcgc gctgcatggc ctggtcaacg cctgcgcgca    1620
tcgcggcgcc atgttgtgcc ggcgcaaaca aggcaacaag gctcattca  cttgcccctt    1680 ccatggctgg acgttcagca acgccggcaa gctgctcaag gtaaaggacg caaagaccgg    1740
```

```
cgcctacccg  dacagcttcg  actgcgacgg  ctcccatgac  ctcaagcgcc  tggcgcgctt   1800
tgaaaactac  cgcggtttcc  tgttcgccag  cctcagcgat  gcggtgccgg  aactcagcga   1860
ttacttgggt  gaaacccgcg  tcatcatcga  ccagatggtc  gaccaggccc  ctttgggcct   1920
ggaggtgctg  cgcggcagct  cttcctatgt  ctatgacggc  aactggaagc  tgcaaatcga   1980
aaacggcgcc  gacggttacc  acgtcagctc  cgtgcactgg  aactactcgg  cgaccatggg   2040
ccggcgcaac  tacgacgccg  aaggcacgcg  caccgtcgac  gccaatggct  ggtcgaaaag   2100
cctgggcggg  gtctacgcct  tcgaccacgg  gcatatcctg  ctgtggacgc  gcctgcttaa   2160
cccccaagtg  cgcccggtgc  acgctcaccg  cgaggccttg  gccgaacgcc  tgggccaagc   2220
gcgcgccgac  tttatcgtcg  accagacccg  caacctctgt  ctctacccca  atgtgtacct   2280
gatggaccag  ttctcgaccc  agatccgcgt  ggtgcggccc  ctcgccgtgg  ataaaaccga   2340
agtgacaatc  tattgcatgg  cgcccatcgg  cgaaagcgcc  caggagcgcg  ccacgcggat   2400
tcgccagtac  gaagacttct  tcaatgtcag  cggcatgggc  accccggatg  acctcgagga   2460
gttccgcgcc  tgccagaccg  gttaccaggg  cgcgagcacc  ctgtggaatg  acttgagccg   2520
tggcgccaag  cagtgggtcg  agggtgcgga  cgaaaatgcc  ttggccatgg  gtatgcaacc   2580
gcagctcagc  ggggtcaaga  ccgaggacga  gggcttgttt  gtgcgccagc  atgcgcactg   2640
ggcccaaagc  ctgcagcgtg  caatcgagcg  cgaacagcaa  gggctgatag  ccagcgactg   2700
tgaggtgctg  ccatgagcct  tgcccgggac  cacctgctgg  attttctta  ccgtgaagcg   2760
cgcctgctcg  acgaccgcca  atgggatgaa  tggctggcct  gctattcgcc  caaggccgag   2820
ttctggatgc  cgcctgggga  cgatcacgac  actcttaccg  aagacccgca  gcgcgaaatc   2880
tcgctgatct  actaccccaa  ccgtgacggc  ctggaagacc  gcatctttcg  catcaagact   2940
gagcgctcca  gcgccagcac  gcccgagccg  cgcaccgtgc  acatgctgtg  caacctcgaa   3000
gtgctggccg  acgacggcgc  gcaggtggac  ctgcgtttca  actggcacac  cctcagccac   3060
cgctacaaaa  ccaccgacag  ttatttcggt  acctccttct  atcgcctcga  catccgtgcc   3120
gagcagccgt  tgataacgcg  caagaaggtg  gtgctgaaaa  acgattacat  ccaccaggtc   3180
atcgacatct  accatatctg  aggacaccgc  catgacgtat  gccatcgcct  tgaacttcga   3240
ggatggagtg  acccgcttca  tcgactgcaa  ggtgggagaa  aaggtgctcg  atgcggcctt   3300
ccgccaacgc  atcaacctgc  ccatggactg  ctcggacggc  gtgtgcggca  cctgcaaatg   3360
ccgctgtgaa  accggcgcct  acgacctggg  cgacgacttt  atcgacgacg  ccctgagcgc   3420
cgacgaagcg  caggcgcgcc  gggtgctgac  ctgccaaatg  gtgccgcagt  ccgactgcgt   3480
gatcgccgtg  ccggtgccgt  ccagcgcctg  caagaccggc  accacgcact  tgccgcgcac   3540
gctggccggc  atcacccgac  atgccgatgc  ggcgctggag  gtgagtttcg  aactggacca   3600
ggcgccggta  ttcctgcccg  gccagtacgt  gaatatcagc  gtgcccgaca  gtgggcagac   3660
tcgtgcttac  tccttcagca  gtcccccggg  cgacccgcgc  gccagcttcc  tgatcaagca   3720
cgtgcccggc  gggttgatga  gcggttggct  cgagcgcgcc  cagccgggcg  acagcgtggc   3780
gatcaccggc  ccactgggga  gtttctacct  gcgtgaggtg  gcgcggccgc  tgctgttact   3840
ggccggtggt  accggcctgg  cgccgttcct  gtcgatgctt  gaagtgctcg  cgcagcgcca   3900
ggaaacccgc  ccgatccggt  tgatctacgg  cgtaacgcgg  gatcaggacc  tggtgatgat   3960
tgaggcgttg  caggctttta  ccgcgcgttt  gcccgacttc  aacctggtga  cctgcgtggc   4020
tgatccgcac  accactcacc  cgcgccaggg  ctatgtgacc  cagcacatgg  ccgacgaagc   4080
```

-continued

```
cctcaatggc ggcgatgtcg acgtgtacct gtgcggcccg ccgccgatgg tcgatgcggt    4140
gcgcgagcac ttcaagcagc aaagcgtgac cccggccagc ttccattacg agaaattcac    4200
ccctaacgcc gtcgccacgt gcgatgccgc ctgaggactg ccgcatgact caacggttta    4260
acaacaaggt cgcgctggtt accggcgctg cgcaaggcat cggccgacgt gtcgccgaac    4320
gcttgctgga ggaggggcc tggctggtcg cggtggatcg ctccgagctc gtgcatgaat    4380
tgcagcatga gcgagcgcta ctgctgaccg ccgacctgga acaatacagc gagtgcgcac    4440
gggtaatggc cgccgccacg gcgcgtttcg ggcgcataga cgtgctggtc aataacgtcg    4500
gcgggaccat ctgggccaag cctttgagc attatgccga ggctgaaatc gaggccgaag     4560
tgcgccgctc gctgttccct acgttgtggt gctgccattg cgtgctgccc tatatgctgg    4620
agcagggcgc gggcgcgatc gtcaacgtgt cttccgtggc cacgcgcggg gtcaatcgcg    4680
tgccctatgg cgcagccaag ggcggcgtga atgccttgac ggcctgcctg ccctggaga    4740 ctgcaggcag cgggattcgc gtcaacgcca ccgcgcccgg cggcaccgag gcaccgccac    4800
ggcgcatccc gcgcaacagc cagccgcaga gcgagcagga acgtgtgtgg taccagcaga    4860
tcgtcgacca gaccctcgag agcagctcga tgaaacgcta cggcagcatc gacgaacaag    4920
ctggcgcaat tctgttcctg gcctgcgacg aggcctccta catcaccggc gtgaccttgc    4980
cggtgggcgg cggcgacctc ggctaa                                         5006
```

```
<210> SEQ ID NO 2
<211> LENGTH: 335
<212> TYPE: PRT
<213> ORGANISM: Pseudomonas fluorescens
<220> FEATURE:
<221> NAME/KEY: INIT_MET
<222> LOCATION: (1)...(1)
<223> OTHER INFORMATION: Alternative putative initiator methionine for
      BenR, giving Met1->Arg335 as the amino acid
      sequence of the Pben activator protein
<220> FEATURE:
<221> NAME/KEY: INIT_MET
<222> LOCATION: (21)...(21)
<223> OTHER INFORMATION: Putative initiator methionine of BenR, giving
      Met21->Arg335 as the amino acid sequence of the
      Pben activator protein
<220> FEATURE:
<221> NAME/KEY: VARIANT
<222> LOCATION: (152)...(152)
<223> OTHER INFORMATION: A mutation of Ser152->Asn152

<400> SEQUENCE: 2

Met Asp Ala Pro Leu Pro Lys Arg Gln Pro Glu Pro Asn Asn Asp Lys
 1               5                  10                  15

Arg Val Ala Thr Met Thr Val Leu Leu Ser Glu Arg Ser Gln Ile Phe
             20                  25                  30

Gln Gly Ala Asp Ala Tyr Ala Val Ser Asp Tyr Val Asn Gln His Val
         35                  40                  45

Gly Ser His Cys Ile Arg Leu Pro Pro Arg Gly Gln Pro Arg Ala Ser
     50                  55                  60

Ile Ser His Arg Thr Phe Ala Ser Leu Asp Leu Cys Arg Ile Ser Tyr
 65                  70                  75                  80

Gly Ala Pro Val Arg Val Thr Ser Val Ala Leu Glu Thr Ile Tyr His
                 85                  90                  95

Leu Gln Ile Leu Leu Ser Gly His Cys Arg Ser Asn Ser Arg Gly Glu
            100                 105                 110

Asp Asp Val Phe Gly Pro Gly Glu Ile Leu Leu Ile Asn Pro Asp Asp
        115                 120                 125
```

```
Pro Val Asp Leu Thr Tyr Ser Ala Asp Cys Glu Lys Phe Ile Ile Lys
    130                 135                 140

Leu Pro Val Arg Leu Leu Glu Ser Ala Cys Leu Glu Gln His Trp Ser
145                 150                 155                 160

Leu Pro Arg Ala Gly Val Arg Phe Thr Thr Ala Arg His Ala Leu Ser
                165                 170                 175

Glu Met Gly Gly Phe Leu Pro Leu Leu Gly Leu Ile Cys His Glu Ala
            180                 185                 190

Glu Asn Ala Ala Glu Pro His Met Gln Gly Leu Tyr Glu Arg Ile Val
        195                 200                 205

Ala Asn Lys Leu Leu Ala Leu Leu Gly Ser Asn Val Ser Arg Val Thr
    210                 215                 220

Pro Arg Ala Ala His Gly Gly Gly Phe Glu Ala Val His Glu Phe Ile
225                 230                 235                 240

Gln Gln His Leu Gly Asp Asp Ile Ser Val Glu Gln Leu Met Ala Val
                245                 250                 255

Ala Asn Val Ser Glu Arg Ser Leu Tyr Ser Leu Phe Glu Arg Gln Val
            260                 265                 270

Gly Leu Ser Pro Arg Asp Tyr Val Cys Arg Cys Lys Leu Glu Arg Val
        275                 280                 285

His Ala Arg Leu Gln Leu Ser Ser Thr Arg Ser Val Thr Glu Val Ala
    290                 295                 300

Leu Asp His Gly Phe Met His Leu Gly Arg Phe Ser Glu Ala Tyr Arg
305                 310                 315                 320

Lys Arg Phe Gly Glu Leu Pro Ser Gln Thr Trp Lys Arg His Arg
                325                 330                 335

<210> SEQ ID NO 3
<211> LENGTH: 458
<212> TYPE: PRT
<213> ORGANISM: Pseudomonas fluorescens
<220> FEATURE:
<221> NAME/KEY: misc_feature
<222> LOCATION: 1..458
<223> OTHER INFORMATION: BenB expression product, benzoate
      1,2-dioxygenase beta subunit

<400> SEQUENCE: 3

Met Ile Ser Thr Pro Asp Arg Leu Ala Cys Gln Leu Arg Glu Ser Val
1               5                   10                  15

Gln Glu Asp Pro Ala Thr Gly Val Phe Arg Cys Arg Arg Asp Ile Phe
            20                  25                  30

Thr Asp Pro Asp Leu Phe Ala Leu Glu Met Lys His Ile Phe Glu Gly
        35                  40                  45

Gly Trp Ile Tyr Leu Ala His Glu Ser Gln Val Pro Gln Ile Asn Asp
    50                  55                  60

Tyr Phe Thr Thr Trp Ile Gly Arg Gln Pro Val Val Ile Thr Arg Asp
65                  70                  75                  80

Lys His Gly Ala Leu His Gly Leu Val Asn Ala Cys Ala His Arg Gly
                85                  90                  95

Ala Met Leu Cys Arg Arg Lys Gln Gly Asn Lys Gly Ser Phe Thr Cys
            100                 105                 110

Pro Phe His Gly Trp Thr Phe Ser Asn Ala Gly Lys Leu Leu Lys Val
        115                 120                 125

Lys Asp Ala Lys Thr Gly Ala Tyr Pro Asp Ser Phe Asp Cys Asp Gly
    130                 135                 140
```

Ser His Asp Leu Lys Arg Leu Ala Arg Phe Glu Asn Tyr Arg Gly Phe
145                 150                 155                 160

Leu Phe Ala Ser Leu Ser Asp Ala Val Pro Glu Leu Ser Asp Tyr Leu
            165                 170                 175

Gly Glu Thr Arg Val Ile Ile Asp Gln Met Val Asp Gln Ala Pro Leu
        180                 185                 190

Gly Leu Glu Val Leu Arg Gly Ser Ser Tyr Val Tyr Asp Gly Asn
    195                 200                 205

Trp Lys Leu Gln Ile Glu Asn Gly Ala Asp Gly Tyr His Val Ser Ser
210                 215                 220

Val His Trp Asn Tyr Ser Ala Thr Met Gly Arg Arg Asn Tyr Asp Ala
225                 230                 235                 240

Glu Gly Thr Arg Thr Val Asp Ala Asn Gly Trp Ser Lys Ser Leu Gly
            245                 250                 255

Gly Val Tyr Ala Phe Asp His Gly His Ile Leu Leu Trp Thr Arg Leu
        260                 265                 270

Leu Asn Pro Gln Val Arg Pro Val His Ala His Arg Glu Ala Leu Ala
    275                 280                 285

Glu Arg Leu Gly Gln Ala Arg Ala Asp Phe Ile Val Asp Gln Thr Arg
290                 295                 300

Asn Leu Cys Leu Tyr Pro Asn Val Tyr Leu Met Asp Gln Phe Ser Thr
305                 310                 315                 320

Gln Ile Arg Val Val Arg Pro Leu Ala Val Asp Lys Thr Glu Val Thr
            325                 330                 335

Ile Tyr Cys Met Ala Pro Ile Gly Glu Ser Ala Gln Glu Arg Ala Thr
        340                 345                 350

Arg Ile Arg Gln Tyr Glu Asp Phe Phe Asn Val Ser Gly Met Gly Thr
    355                 360                 365

Pro Asp Asp Leu Glu Glu Phe Arg Ala Cys Gln Thr Gly Tyr Gln Gly
370                 375                 380

Ala Ser Thr Leu Trp Asn Asp Leu Ser Arg Gly Ala Lys Gln Trp Val
385                 390                 395                 400

Glu Gly Ala Asp Glu Asn Ala Leu Ala Met Gly Met Gln Pro Gln Leu
            405                 410                 415

Ser Gly Val Lys Thr Glu Asp Glu Gly Leu Phe Val Arg Gln His Ala
        420                 425                 430

His Trp Ala Gln Ser Leu Gln Arg Ala Ile Glu Arg Glu Gln Gln Gly
    435                 440                 445

Leu Ile Ala Ser Asp Cys Glu Val Leu Pro
450                 455

<210> SEQ ID NO 4
<211> LENGTH: 162
<212> TYPE: PRT
<213> ORGANISM: Pseudomonas fluorescens
<220> FEATURE:
<221> NAME/KEY: misc_feature
<222> LOCATION: 1..162
<223> OTHER INFORMATION: BenC expression product, benzoate
      1,2-dioxygenase electron transfer component

<400> SEQUENCE: 4

Met Ser Leu Ala Arg Asp His Leu Leu Asp Phe Leu Tyr Arg Glu Ala
1               5                   10                  15

Arg Leu Leu Asp Asp Arg Gln Trp Asp Glu Trp Leu Ala Cys Tyr Ser
            20                  25                  30

Pro Lys Ala Glu Phe Trp Met Pro Ala Trp Asp Asp His Asp Thr Leu
             35                  40                  45

Thr Glu Asp Pro Gln Arg Glu Ile Ser Leu Ile Tyr Tyr Pro Asn Arg
 50                  55                  60

Asp Gly Leu Glu Asp Arg Ile Phe Arg Ile Lys Thr Glu Arg Ser Ser
 65                  70                  75                  80

Ala Ser Thr Pro Glu Pro Arg Thr Val His Met Leu Cys Asn Leu Glu
                 85                  90                  95

Val Leu Ala Asp Asp Gly Ala Gln Val Asp Leu Arg Phe Asn Trp His
             100                 105                 110

Thr Leu Ser His Arg Tyr Lys Thr Thr Asp Ser Tyr Phe Gly Thr Ser
             115                 120                 125

Phe Tyr Arg Leu Asp Ile Arg Ala Glu Gln Pro Leu Ile Thr Arg Lys
 130                 135                 140

Lys Val Val Leu Lys Asn Asp Tyr Ile His Gln Val Ile Asp Ile Tyr
145                 150                 155                 160

His Ile

<210> SEQ ID NO 5
<211> LENGTH: 340
<212> TYPE: PRT
<213> ORGANISM: Pseudomonas fluorescens
<220> FEATURE:
<221> NAME/KEY: misc_feature
<222> LOCATION: 1..340
<223> OTHER INFORMATION: BenC expression product, benzoate
      1,2-dioxygenase electron transfer component

<400> SEQUENCE: 5

Met Thr Tyr Ala Ile Ala Leu Asn Phe Glu Asp Gly Val Thr Arg Phe
 1               5                  10                  15

Ile Asp Cys Lys Val Gly Glu Lys Val Leu Asp Ala Ala Phe Arg Gln
             20                  25                  30

Arg Ile Asn Leu Pro Met Asp Cys Ser Asp Gly Val Cys Gly Thr Cys
             35                  40                  45

Lys Cys Arg Cys Glu Thr Gly Ala Tyr Asp Leu Gly Asp Asp Phe Ile
 50                  55                  60

Asp Asp Ala Leu Ser Ala Asp Glu Ala Gln Ala Arg Arg Val Leu Thr
 65                  70                  75                  80

Cys Gln Met Val Pro Gln Ser Asp Cys Val Ile Ala Val Pro Val Pro
                 85                  90                  95

Ser Ser Ala Cys Lys Thr Gly Thr Thr His Phe Ala Ala Thr Leu Ala
             100                 105                 110

Gly Ile Thr Arg His Ala Asp Ala Ala Leu Glu Val Ser Phe Glu Leu
             115                 120                 125

Asp Gln Ala Pro Val Phe Leu Pro Gly Gln Tyr Val Asp Ile Ser Val
 130                 135                 140

Pro Asp Ser Gly Gln Thr Arg Ala Tyr Ser Phe Ser Ser Pro Pro Gly
145                 150                 155                 160

Asp Pro Arg Ala Ser Phe Leu Ile Lys His Val Pro Gly Gly Leu Met
                 165                 170                 175

Ser Glu Trp Leu Glu Arg Ala Gln Pro Gly Asp Ser Val Ala Ile Thr
             180                 185                 190

Gly Pro Leu Gly Ser Phe Tyr Leu Arg Glu Val Ala Arg Pro Leu Leu
             195                 200                 205

```
Leu Leu Ala Gly Gly Thr Gly Leu Ala Pro Phe Leu Ser Met Leu Glu
    210                 215                 220
Val Leu Ala Gln Arg Gln Glu Thr Arg Pro Ile Arg Leu Ile Tyr Gly
225                 230                 235                 240
Val Thr Arg Asp Gln Asp Leu Val Met Ile Glu Ala Leu Gln Ala Phe
                245                 250                 255
Thr Ala Arg Leu Pro Asp Phe Asn Leu Val Thr Cys Val Ala Asp Pro
            260                 265                 270
His Thr Thr His Pro Arg Gln Gly Tyr Val Thr Gln His Met Ala Asp
        275                 280                 285
Glu Ala Leu Asn Gly Gly Asp Val Asp Val Tyr Leu Cys Gly Pro Pro
290                 295                 300
Pro Met Val Asp Ala Val Arg Glu His Phe Lys Gln Gln Ser Val Thr
305                 310                 315                 320
Pro Ala Ser Phe His Tyr Glu Lys Phe Thr Pro Asn Ala Val Ala Thr
                325                 330                 335
Cys Asp Ala Ala
            340

<210> SEQ ID NO 6
<211> LENGTH: 260
<212> TYPE: PRT
<213> ORGANISM: Pseudomonas fluorescens
<220> FEATURE:
<221> NAME/KEY: misc_feature
<222> LOCATION: (1)...(260)
<223> OTHER INFORMATION: BenD expression product,
      cis-1,2-dihydroxycyclohexa-3,5-diene-1-carboxylate
      dehydrogenase

<400> SEQUENCE: 6

Met Pro Pro Glu Asp Cys Arg Met Thr Gln Arg Phe Asn Asn Lys Val
1               5                   10                  15
Ala Leu Val Thr Gly Ala Ala Gln Gly Ile Gly Arg Arg Val Ala Glu
                20                  25                  30
Arg Leu Leu Glu Glu Gly Ala Trp Leu Val Ala Val Asp Arg Ser Glu
            35                  40                  45
Leu Val His Glu Leu Gln His Glu Arg Ala Leu Leu Leu Thr Ala Asp
        50                  55                  60
Leu Glu Gln Tyr Ser Glu Cys Ala Arg Val Met Ala Ala Ala Thr Ala
65                  70                  75                  80
Arg Phe Gly Arg Ile Asp Val Leu Val Asn Asn Val Gly Gly Thr Ile
                85                  90                  95
Trp Ala Lys Pro Phe Glu His Tyr Ala Glu Ala Glu Ile Glu Ala Glu
                100                 105                 110
Val Arg Arg Ser Leu Phe Pro Thr Leu Trp Cys Cys His Cys Val Leu
            115                 120                 125
Pro Tyr Met Leu Glu Gln Gly Ala Gly Ala Ile Val Asn Val Ser Ser
        130                 135                 140
Val Ala Thr Arg Gly Val Asn Arg Val Pro Tyr Gly Ala Ala Lys Gly
145                 150                 155                 160
Gly Val Asn Ala Leu Thr Ala Cys Leu Ala Leu Glu Thr Ala Gly Ser
                165                 170                 175
Gly Ile Arg Val Asn Ala Thr Ala Pro Gly Gly Thr Glu Ala Pro Pro
            180                 185                 190
Arg Arg Ile Pro Arg Asn Ser Gln Pro Gln Ser Glu Gln Glu Arg Val
        195                 200                 205
```

```
Trp Tyr Gln Gln Ile Val Asp Gln Thr Leu Glu Ser Ser Ser Met Lys
    210                 215                 220

Arg Tyr Gly Ser Ile Asp Glu Gln Ala Gly Ala Ile Leu Phe Leu Ala
225                 230                 235                 240

Cys Asp Glu Ala Ser Tyr Ile Thr Gly Val Thr Leu Pro Val Gly Gly
                245                 250                 255

Gly Asp Leu Gly
            260

<210> SEQ ID NO 7
<211> LENGTH: 4330
<212> TYPE: DNA
<213> ORGANISM: Pseudomonas fluorescens
<220> FEATURE:
<221> NAME/KEY: misc_feature
<222> LOCATION: (1)...(4330)
<223> OTHER INFORMATION: Anthranilate Operon controlling expression of
      antABC
<220> FEATURE:
<221> NAME/KEY: misc_signal
<222> LOCATION: (1)...(3)
<223> OTHER INFORMATION: Anticodon of stop codon for the CDS of AntR
<220> FEATURE:
<221> NAME/KEY: CDS
<222> LOCATION: (4)...(993)
<223> OTHER INFORMATION: Antisense strand of ORF encoding AntR
<220> FEATURE:
<221> NAME/KEY: variation
<222> LOCATION: (192)...(192)
<223> OTHER INFORMATION: Mutation to A235 from native C235; resulting in
      the anticodon mutation CGC->CGA shown at 233..235,
      thus codon mutation GCG->TCG and amino acid
      mutation of Ala268 to Ser268
<220> FEATURE:
<221> NAME/KEY: misc_signal
<222> LOCATION: (1130)...(1237)
<223> OTHER INFORMATION: Approximate region estimated to contain the
      AntR binding site
<220> FEATURE:
<221> NAME/KEY: promoter
<222> LOCATION: (1239)...(1274)
<223> OTHER INFORMATION: Putative promoter (Pant) from anthranilate
      operon (antABC)
<220> FEATURE:
<221> NAME/KEY: -35_signal
<222> LOCATION: (1239)...(1244)
<223> OTHER INFORMATION: Putative -35 region of Pant promoter
<220> FEATURE:
<221> NAME/KEY: -10_signal
<222> LOCATION: (1264)...(1268)
<223> OTHER INFORMATION: Putative -10 region of Pant promoter
<220> FEATURE:
<221> NAME/KEY: misc_feature
<222> LOCATION: (1264)...(1268)
<223> OTHER INFORMATION: Substitution mutation of Pant -10 region by
      tataat to form -10con mutants
<220> FEATURE:
<221> NAME/KEY: misc_feature
<222> LOCATION: (1269)...(1269)
<223> OTHER INFORMATION: A deletion of g1269 found in mutant promoter
      variants herein
<220> FEATURE:
<221> NAME/KEY: misc_signal
<222> LOCATION: (1274)...(1274)
<223> OTHER INFORMATION: Putative transcription start site under control
      of Pant
<220> FEATURE:
<221> NAME/KEY: misc_feature
<222> LOCATION: (1278)...(1278)
<223> OTHER INFORMATION: A deletion of t1278 found in mutant promoter
      variants herein
<220> FEATURE:
<221> NAME/KEY: misc_signal
<222> LOCATION: (1305)...(1307)
```

<223> OTHER INFORMATION: Putative native translation initiator codon
<220> FEATURE:
<221> NAME/KEY: CDS
<222> LOCATION: (1305)...(2693)
<223> OTHER INFORMATION: AntA open reading frame encoding anthranilate
      dioxygenase large subunit
<220> FEATURE:
<221> NAME/KEY: misc_signal
<222> LOCATION: (2694)...(2696)
<223> OTHER INFORMATION: AntA stop codon
<220> FEATURE:
<221> NAME/KEY: CDS
<222> LOCATION: (2696)...(3184)
<223> OTHER INFORMATION: AntB open reading frame encoding anthranilate
      dioxygenase small subunit
<220> FEATURE:
<221> NAME/KEY: misc_signal
<222> LOCATION: (3185)...(3187)
<223> OTHER INFORMATION: AntB stop codon
<220> FEATURE:
<221> NAME/KEY: CDS
<222> LOCATION: (3323)...(4327)
<223> OTHER INFORMATION: AntC open reading frame encoding anthranilate
      dioxygenase reductase
<220> FEATURE:
<221> NAME/KEY: misc_signal
<222> LOCATION: (4328)...(4330)
<223> OTHER INFORMATION: AntC stop codon

<400> SEQUENCE: 7

```
tcaagtaatg cgcaggcgct tgcgctgcaa tgtctggctg ggcgactcat cgaacagctt      60
gcggtactcc gccgaaaacc gccccaaatg cgtaaacccc caacccaggg cgatttcaga     120
gatggtgcgg atcgagccct gctccagaat ttcttggcgc accgccccca accgatgctt     180
cttcaaatac gccatgggcg acagtgcgaa gtacttgcga aacgcatcga acagtttgaa     240
acgcgacacg cccgccgccg cttccaggtc ttccaggtgc agcgcttcac gggcgttgtc     300
gtggataaat tgccgcgcgc ggatcaggta gtgcggcagt ttcaccccca gcacgtcgcg     360
cagttcttcg gagtagttat tcggttgggc caggatcagg cccttgatca gcgagctttc     420
caggtcgcga gtaaacgccg cctgctcgta cagttcgctg ctgcgctcca gttcggcgat     480
gaaataacgc gccatgcgcc accacgaagc cggtgctccg tccacagcat ccatcaccga     540
ctcaaagcgc agcggcgcat caatgggccg ttgcagcaaa ccttccagcg actcgctcat     600
cgccgcacgg gtgattacca cctgcaactt gcggcagtca ccggaaatcg ccagcacctg     660
atgctcattg ggcgaaatga tcacgccttg gtcgcggttg gaactgagac gttcaccgtt     720
cttgctcagc tcctgctcgc ccaccagtgg caggctcaag ctgtagctgc tgaagtgctc     780
ggcgtcttcg atgtcgatgg tcacatcagt gccgtactcg atcacgccca gggtggtggc     840
gcggatttg aacacgttgg cgctgtggtg aaagcgcagg cgctcggggg ttgccgtcgc     900
caggcgatgg ggcccgcaga tgccggacat ccagctgcgc gcgccttcca ggtcgaagcg     960
ttgaatatga atatcgcgtg tctgactagt catcagggtg cacccacggc ggttaggcgt    1020
ttgcgcgctc tgacggcgcg tcgttgaacc tcgacagcaa gttccaggcc acgccagtgc    1080
agttctcact gggtggatag caacggtcga ctatgtggat aaaccccaga gttttgcgac    1140
catcgcccgc catcacagta gcgcatgccg tcaccggcgc gcaccgtcat gggtatttgc    1200
cgcccaactt tgcggcctac gttccccat taagcggata gcccgccacc gcatcgcagc    1260
cgcttaatgg ctcaccgttt agccatgatc aaaaggtgcc tcccatgagt ggtgcaagaa    1320
ccgtcgagca atggaaatcc tttatcgaaa gctgcctgga cttcgcccg gcggatgaag    1380
tgttccgcat cgcccgcgac atgttcaccg agcccgagtt gttcgacctg gagatgggagc   1440
```

```
tgatcttcga gaagaactgg atctacgcct gccacgaaag cgaactggcc aataaccacg    1500
acttcgtgac gatgcgcgcc ggccgccagc cgatgatcat cacccgtgac ggcgaaggcc    1560
gactcaacgc gttgatcaac gcctgccagc atcgcggtac caccctcacc cgcgtgggca    1620
agggtaacca gtccaccttc acctgcccgt tccacgcctg gtgctacaag agcgatggcc    1680
gactggtaaa ggtcaaggcg ccgggggaat acccggaagg tttcgacaag gccacccgcg    1740
gcctgaaaaa agcgcgcatc gaaagctaca ggggctttgt gtttatcagc ctggacgtga    1800
acggcaccaa cagcctggag gacttcctgg gcgatgccaa agtgttcttc gacatgatgg    1860
tggcgcaatc ggccaccggt gagctggaag tgctgccggg caagtccgcc tacacctacg    1920
acggcaactg gaagctgcaa acgaaaacg gcctggacgg ttatcacgtc agcaccgtgc     1980
actacaacta cgtggccacc gtgcagcatc gcgagcaggt caacaccgaa acgcgcgcag    2040
gttccagcac gacgttggac tacagcaagc tcggcgccgg cgacgccaat accgacgacg    2100
gctggttcgc cttcaacaac ggccacgcg tgttgtttag cgacatgccc aaccccagcg     2160
tgcgctccgg ctacgccacc atcatgccgc gcctggtaga agaacacggc cagcagaagg    2220
ccgagtggat gatgcaccgc ctgcgcaacc tgaatatcta ccccagcctg tttttcctcg    2280
accagatcag ctcgcagttg cgcatcatcc gcccggtggc ctggaacaag accgagatca    2340
tcagccagtg cctgggggtt aagggcgagt ccgacgccga ccgcgaaaac cggattcgtc    2400
agttcgaaga cttcttcaac gtttcaggca tgggcacgcc cgatgacctg gtggagtttc    2460
gcgaagccca gcgtggcttt cagggccgcc tggaacgctg gagcgacatc tcacggggca    2520
gccatcgctg ggagaccggg ccgacgccaa acagcgaggc catcggcatc caaccggcga    2580
tgaccggtac cgaattcacc catgaaggcc tgtacgtcaa ccagcatcgc aactggcagc    2640
agttcctgct aaagggtttg gaccagcgag ccctggcact gcgggaggtg aagtgatgaa    2700
tgcgcaattg cagtaccaga tcgagcagtt cttctatcgc aagtccgagc tgtgcgacgc    2760
ccaggactgg gacgcctacg tgcagttgtt cgacccgcag agtgaattcc acctgccgca    2820
atgggactcc gaacacgtct acacccaaga ccccaagcgc gagatgtcat tgatctacta    2880
cgccaaccgt tcgggcctgg aagaccgtgt gttccgcctg cgcaccggca aagccgcctc    2940
tgccacgccg atgccgcgca cttttgcacct gatcaataac gtacgcattg ccgagcaggc    3000
cgatggcacg ttggaggtgc gttttgaactg gcacacattg ttttatcgcc tggccacgtc    3060
cgagcagttt tacgggcatg ccacgtaccg cctcaagcct gcgggcgaca gctggttgat    3120
catgcgcaag cacgccttgt tgctcaacga caccatcaac tcggtgctgg atttctacca    3180
cctgtaacgg tggtgcatcg ccctgtagga gcgagcttgc tcgcgaaaaa cgtaagtacg    3240
ccgcgttcat tcaggatgtc ccgcgtcatc gttgacgttt ttcgcgagca agggttcat     3300 acctattcac ggagttatgt gaatgaatca caaagtggcc ttcagctttg ccgatggcaa    3360 gacccctgttc ttcccggtgg cgcccatga atcctcctg gacgcggccc tgcgcaacgg     3420
catcaagatc ccgctcgatt gccgcgaagg cgtgtgcggc acctgccagg ggcgctgtga    3480
gtccggcgag tacacccagg actatgtcga tgaggaagcc ctctccagcc tcgacctgca    3540
acaacgcaag atgctcagtt gccaaacccg ggtgaagtcc gacgccacgt tttatttcga    3600
ctttgactca agcctgtgca cgccccagg ccccgtgcag gtgcgcggca ctgtgagcgc     3660
ggtgcagcag gtatcgacca gcaccgccat tttgcaggtg caactggacc agcctctgga    3720 tttttttgccg ggccaatacg cgcgtctgtc ggtgcccggc accgatagct ggcgctccta    3780
ctccttcgcc aaccggccgg gtaatcagtt gcagttcctg gtacgcctgc tgcccgacgg    3840
```

-continued

| | |
|---|---|
| agtcatgagc aactacctgc gtgaacgctg ccaggtgggt gatgaaatgc tgatggaggc | 3900 |
| gcccttgggt gcgttttatc tgcggcacgt cacccaaccg ctggtactgg tggcgggcgg | 3960 |
| caccggggttg tcggcgttgt tgggcatgct cgatgagctg gtcgtcaacg gctgcacaca | 4020 |
| acctgtgcac ctgtactacg gcgtgcgcgg cgccgaagac ttatgtgaag cggcacgtat | 4080 |
| ccacgcctac gcgacgaaaa tcccgaactt cgctacacc gaagtgctga gcgacgcctc | 4140 |
| agtcgagtgg acgggcaaac gcggctacct gaccgaacat tttgacctgg ccgaattgcg | 4200 |
| ggacagatcg gcggatatgt acgtgtgcgg ccccccctcca atggtcgaat ccatccaaca | 4260 |
| atggctggcg gatcagacac ttgatggcgt tcagttgtat tacgaaaagt ttacccagag | 4320 |
| taatatctga | 4330 |

```
<210> SEQ ID NO 8
<211> LENGTH: 993
<212> TYPE: DNA
<213> ORGANISM: Pseudomonas fluorescens
<220> FEATURE:
<221> NAME/KEY: CDS
<222> LOCATION: (1)...(990)
<223> OTHER INFORMATION: Coding sequence for AntR
<220> FEATURE:
<221> NAME/KEY: variation
<222> LOCATION: (802)...(802)
<223> OTHER INFORMATION: Mutation to T802 from native G802; resulting in
      the codon mutation GCG->TCG shown at 802..804, and
      the amino acid mutation of Ala268 to Ser268
<220> FEATURE:
<221> NAME/KEY: misc_signal
<222> LOCATION: (991)...(993)
<223> OTHER INFORMATION: Stop codon for the CDS of AntR
```

<400> SEQUENCE: 8

| | |
|---|---|
| atg act agt cag aca cgc gat att cat att caa cgc ttc gac ctg gaa<br>Met Thr Ser Gln Thr Arg Asp Ile His Ile Gln Arg Phe Asp Leu Glu<br>1                5                10                15 | 48 |
| ggc gcg cgc agc tgg atg tcc ggc atc tgc ggg ccc cat cgc ctg gcg<br>Gly Ala Arg Ser Trp Met Ser Gly Ile Cys Gly Pro His Arg Leu Ala<br>                20                25                30 | 96 |
| acg gca acc ccc gag cgc ctg cgc ttt cac cac agc gcc aac gtg ttc<br>Thr Ala Thr Pro Glu Arg Leu Arg Phe His His Ser Ala Asn Val Phe<br>            35                40                45 | 144 |
| aaa tcc cgc gcc acc acc ctg ggc gtg atc gag tac ggc act gat gtg<br>Lys Ser Arg Ala Thr Thr Leu Gly Val Ile Glu Tyr Gly Thr Asp Val<br>50                  55                60 | 192 |
| acc atc gac atc gaa gac gcc gag cac ttc agc agc tac agc ttg atc<br>Thr Ile Asp Ile Glu Asp Ala Glu His Phe Ser Ser Tyr Ser Leu Ile<br>65                  70                75                80 | 240 |
| ctg cca ctg gtg ggc gag cag gag ctg agc aag aac ggt gaa cgt ctc<br>Leu Pro Leu Val Gly Glu Gln Glu Leu Ser Lys Asn Gly Glu Arg Leu<br>                85                90                95 | 288 |
| agt tcc aac cgc gac caa ggc gtg atc att tcg ccc aat gag cat cag<br>Ser Ser Asn Arg Asp Gln Gly Val Ile Ile Ser Pro Asn Glu His Gln<br>            100                105                110 | 336 |
| gtg ctg gcg att tcc ggt gac tgc cgc aag ttg cag gtg gta atc acc<br>Val Leu Ala Ile Ser Gly Asp Cys Arg Lys Leu Gln Val Val Ile Thr<br>            115                120                125 | 384 |
| tgc gcg gcg atg agc gag tcg ctg gaa ggt ttg ctg caa cgg ccc att<br>Cys Ala Ala Met Ser Glu Ser Leu Glu Gly Leu Leu Gln Arg Pro Ile<br>            130                135                140 | 432 |
| gat gcg ccg ctg cgc ttt gag tcg gtg atg gat gct gtg gac gga gca<br>Asp Ala Pro Leu Arg Phe Glu Ser Val Met Asp Ala Val Asp Gly Ala | 480 |

```
                145                 150                 155                 160
ccg gct tcg tgg tgg cgc atg gcg cgt tat ttc atc gcc gaa ctg gag    528
Pro Ala Ser Trp Trp Arg Met Ala Arg Tyr Phe Ile Ala Glu Leu Glu
                    165                 170                 175 cgc agc agc gaa ctg tac gag cag gcg gcg ttt act cgc gac ctg gaa    576
Arg Ser Ser Glu Leu Tyr Glu Gln Ala Ala Phe Thr Arg Asp Leu Glu
                180                 185                 190 agc tcg ctg atc aag ggc ctg atc ctg gcc caa ccg aat aac tac tcc    624
Ser Ser Leu Ile Lys Gly Leu Ile Leu Ala Gln Pro Asn Asn Tyr Ser
            195                 200                 205 gaa gaa ctg cgc gac gtg ctg ggg gtg aaa ctg ccg cac tac ctg atc    672
Glu Glu Leu Arg Asp Val Leu Gly Val Lys Leu Pro His Tyr Leu Ile
        210                 215                 220 cgc gcg cgg caa ttt atc cac gac aac gcc cgt gaa gcg ctg cac ctg    720
Arg Ala Arg Gln Phe Ile His Asp Asn Ala Arg Glu Ala Leu His Leu
    225                 230                 235                 240 gaa gac ctg gaa gcg gcg gcg ggc gtg tcg cgt ttc aaa ctg ttc gat    768
Glu Asp Leu Glu Ala Ala Ala Gly Val Ser Arg Phe Lys Leu Phe Asp
                    245                 250                 255 gcg ttt cgc aag tac ttc gca ctg tcg ccc atg tcg tat ttg aag aag    816
Ala Phe Arg Lys Tyr Phe Ala Leu Ser Pro Met Ser Tyr Leu Lys Lys
                260                 265                 270 cat cgg ttg ggg gcg gtg cgc caa gaa att ctg gag cag ggc tcg atc    864
His Arg Leu Gly Ala Val Arg Gln Glu Ile Leu Glu Gln Gly Ser Ile
            275                 280                 285 cgc acc tac tct gaa atc gcc ctg ggt tgg ggg ttt acg cat ttg ggg    912
Arg Thr Tyr Ser Glu Ile Ala Leu Gly Trp Gly Phe Thr His Leu Gly
        290                 295                 300 cgg ttt tcg gcg gag tac cgc aag ctg ttc gat gag tcg ccc agc cag    960
Arg Phe Ser Ala Glu Tyr Arg Lys Leu Phe Asp Glu Ser Pro Ser Gln
305                 310                 315                 320 aca ttg cag cgc aag cgc ctg cgc att act tga                        993
Thr Leu Gln Arg Lys Arg Leu Arg Ile Thr
                    325                 330

<210> SEQ ID NO 9
<211> LENGTH: 330
<212> TYPE: PRT
<213> ORGANISM: Pseudomonas fluorescens
<220> FEATURE:
<221> NAME/KEY: INIT_MET
<222> LOCATION: (1)...(1)
<223> OTHER INFORMATION: Putative initiator methionine for AntR, giving
      Met1->Thr330 as the amino acid sequence of the
      putative Pant activator protein
<220> FEATURE:
<221> NAME/KEY: VARIANT
<222> LOCATION: (268)...(268)
<223> OTHER INFORMATION: Mutation to Ser268 from Ala268

<400> SEQUENCE: 9

Met Thr Ser Gln Thr Arg Asp Ile His Ile Gln Arg Phe Asp Leu Glu
 1               5                  10                  15

Gly Ala Arg Ser Trp Met Ser Gly Ile Cys Gly Pro His Arg Leu Ala
                20                  25                  30

Thr Ala Thr Pro Glu Arg Leu Arg Phe His His Ser Ala Asn Val Phe
            35                  40                  45

Lys Ser Arg Ala Thr Thr Leu Gly Val Ile Glu Tyr Gly Thr Asp Val
        50                  55                  60

Thr Ile Asp Ile Glu Asp Ala Glu His Phe Ser Ser Tyr Ser Leu Ser
65                  70                  75                  80
```

```
Leu Pro Leu Val Gly Glu Gln Glu Leu Ser Lys Asn Gly Glu Arg Leu
                85                  90                  95

Ser Ser Asn Arg Asp Gln Gly Val Ile Ile Ser Pro Asn Glu His Gln
            100                 105                 110

Val Leu Ala Ile Ser Gly Asp Cys Arg Lys Leu Gln Val Val Ile Thr
        115                 120                 125

Arg Ala Ala Met Ser Glu Ser Leu Glu Gly Leu Leu Gln Arg Pro Ile
    130                 135                 140

Asp Ala Pro Leu Arg Phe Glu Ser Val Met Asp Ala Val Asp Gly Ala
145                 150                 155                 160

Pro Ala Ser Trp Trp Arg Met Ala Arg Tyr Phe Ile Ala Glu Leu Glu
                165                 170                 175

Arg Ser Ser Glu Leu Tyr Glu Gln Ala Ala Phe Thr Arg Asp Leu Glu
            180                 185                 190

Ser Ser Leu Ile Lys Gly Leu Ile Leu Ala Gln Pro Asn Asn Tyr Ser
        195                 200                 205

Glu Glu Leu Arg Asp Val Leu Gly Val Lys Leu Pro His Tyr Leu Ile
    210                 215                 220

Arg Ala Arg Gln Phe Ile His Asp Asn Ala Arg Glu Ala Leu His Leu
225                 230                 235                 240

Glu Asp Leu Glu Ala Ala Gly Val Ser Arg Phe Lys Leu Phe Asp
                245                 250                 255

Ala Phe Arg Lys Tyr Phe Ala Leu Ser Pro Met Ser Tyr Leu Lys Lys
                260                 265                 270

His Arg Leu Gly Ala Val Arg Gln Glu Ile Leu Glu Gln Gly Ser Ile
            275                 280                 285

Arg Thr Ile Ser Glu Ile Ala Leu Gly Trp Gly Phe Thr His Leu Gly
        290                 295                 300

Arg Phe Ser Ala Glu Tyr Arg Lys Leu Phe Asp Glu Ser Pro Ser Gln
305                 310                 315                 320

Thr Leu Gln Arg Lys Arg Leu Arg Ile Thr
                325                 330

<210> SEQ ID NO 10
<211> LENGTH: 463
<212> TYPE: PRT
<213> ORGANISM: Pseudomonas fluorescens
<220> FEATURE:
<221> NAME/KEY: misc_feature
<222> LOCATION: 1..463
<223> OTHER INFORMATION: AntA expression product, anthranilate
      dioxygenase large subunit

<400> SEQUENCE: 10

Met Ser Gly Ala Arg Thr Val Glu Gln Trp Lys Ser Phe Ile Glu Ser
1               5                   10                  15

Cys Leu Asp Phe Arg Pro Ala Asp Glu Val Phe Arg Ile Ala Arg Asp
            20                  25                  30

Met Phe Thr Glu Pro Glu Leu Phe Asp Leu Glu Met Glu Leu Ile Phe
        35                  40                  45

Glu Lys Asn Trp Ile Tyr Ala Cys His Glu Ser Glu Leu Ala Asn Asn
    50                  55                  60

His Asp Phe Val Thr Met Arg Ala Gly Arg Gln Pro Met Ile Ile Thr
65                  70                  75                  80

Arg Asp Gly Glu Gly Arg Leu Asn Ala Leu Ile Asn Ala Cys Gln His
                85                  90                  95
```

```
Arg Gly Thr Thr Leu Thr Arg Val Gly Lys Gly Asn Gln Ser Thr Phe
                100                 105                 110

Thr Cys Pro Phe His Ala Trp Cys Tyr Lys Ser Asp Gly Arg Leu Val
            115                 120                 125

Lys Val Lys Ala Pro Gly Glu Tyr Pro Glu Gly Phe Asp Lys Ala Thr
        130                 135                 140

Arg Gly Leu Lys Lys Ala Arg Ile Glu Ser Tyr Arg Gly Phe Val Phe
145                 150                 155                 160

Ile Ser Leu Asp Val Asn Gly Thr Asn Ser Leu Glu Asp Phe Leu Gly
                165                 170                 175

Asp Ala Lys Val Phe Phe Asp Met Met Val Ala Gln Ser Ala Thr Gly
            180                 185                 190

Glu Leu Glu Val Leu Pro Gly Lys Ser Ala Tyr Thr Tyr Asp Gly Asn
        195                 200                 205

Trp Lys Leu Gln Asn Glu Asn Gly Leu Asp Gly Tyr His Val Ser Thr
    210                 215                 220

Val His Tyr Asn Tyr Val Ala Thr Val Gln His Arg Glu Gln Val Asn
225                 230                 235                 240

Thr Glu Asn Gly Ala Gly Ser Ser Thr Thr Leu Asp Tyr Ser Lys Leu
                245                 250                 255

Gly Ala Gly Asp Ala Asn Thr Asp Asp Gly Trp Phe Ala Phe Asn Asn
            260                 265                 270

Gly His Ser Val Leu Phe Ser Asp Met Pro Asn Pro Ser Val Arg Ser
        275                 280                 285

Gly Tyr Ala Thr Ile Met Pro Arg Leu Val Glu Glu His Gly Gln Gln
    290                 295                 300

Lys Ala Glu Trp Met Met His Arg Leu Arg Asn Leu Asn Ile Tyr Pro
305                 310                 315                 320

Ser Leu Phe Phe Leu Asp Gln Ile Ser Ser Gln Leu Arg Ile Ile Arg
                325                 330                 335

Pro Val Ala Trp Asn Lys Thr Glu Ile Ile Ser Gln Cys Leu Gly Val
            340                 345                 350

Lys Gly Glu Ser Asp Ala Asp Arg Glu Asn Arg Ile Arg Gln Phe Glu
        355                 360                 365

Asp Phe Phe Asn Val Ser Gly Met Gly Thr Pro Asp Asp Leu Val Glu
    370                 375                 380

Phe Arg Glu Ala Gln Arg Gly Phe Gln Gly Arg Leu Glu Arg Trp Ser
385                 390                 395                 400

Asp Ile Ser Arg Gly Ser His Arg Trp Glu Thr Gly Pro Trp Pro Asn
                405                 410                 415

Ser Glu Ala Ile Gly Ile Gln Pro Ala Met Thr Gly Thr Glu Phe Thr
            420                 425                 430

His Glu Gly Leu Tyr Val Asn Gln His Arg Asn Trp Gln Gln Phe Leu
        435                 440                 445

Leu Lys Gly Leu Asp Gln Arg Ala Leu Ala Leu Arg Glu Val Lys
    450                 455                 460

<210> SEQ ID NO 11
<211> LENGTH: 163
<212> TYPE: PRT
<213> ORGANISM: Pseudomonas fluorescens
<220> FEATURE:
<221> NAME/KEY: misc_feature
<222> LOCATION: 1..163
<223> OTHER INFORMATION: AntB expression product, anthranilate
      dioxygenase small subunit
```

<400> SEQUENCE: 11

```
Met Asn Ala Gln Leu Gln Tyr Gln Ile Glu Gln Phe Phe Tyr Arg Lys
1               5                   10                  15

Ser Glu Leu Cys Asp Ala Gln Asp Trp Asp Ala Tyr Val Gln Leu Phe
            20                  25                  30

Asp Pro Gln Ser Glu Phe His Leu Pro Gln Trp Asp Ser Glu His Val
        35                  40                  45

Tyr Thr Gln Asp Pro Lys Arg Glu Met Ser Leu Ile Tyr Tyr Ala Asn
    50                  55                  60

Arg Ser Gly Leu Glu Asp Arg Val Phe Arg Leu Arg Thr Glu Lys Ala
65                  70                  75                  80

Ala Ser Ala Thr Pro Met Pro Arg Thr Leu His Leu Ile Asn Asn Val
                85                  90                  95

Arg Ile Ala Glu Gln Ala Asp Gly Thr Leu Glu Val Arg Leu Asn Trp
            100                 105                 110

His Thr Leu Phe Tyr Arg Leu Ala Thr Ser Glu Gln Phe Tyr Gly His
        115                 120                 125

Ala Thr Tyr Arg Leu Lys Pro Ala Gly Asp Ser Trp Leu Ile Met Arg
    130                 135                 140

Lys His Ala Leu Leu Leu Asn Asp Thr Ile Asn Ser Val Leu Asp Phe
145                 150                 155                 160

Tyr His Leu
```

```
<210> SEQ ID NO 12
<211> LENGTH: 335
<212> TYPE: PRT
<213> ORGANISM: Pseudomonas fluorescens
<220> FEATURE:
<221> NAME/KEY: misc_feature
<222> LOCATION: 1..335
<223> OTHER INFORMATION: AntC expression product, anthranilate
      dioxygenase reductase
```

<400> SEQUENCE: 12

```
Met Asn His Lys Val Ala Phe Ser Phe Ala Asp Gly Lys Thr Leu Phe
1               5                   10                  15

Phe Pro Val Gly Ala His Glu Ile Leu Leu Asp Ala Ala Leu Arg Asn
            20                  25                  30

Gly Ile Lys Ile Pro Leu Asp Cys Arg Glu Gly Val Cys Gly Thr Cys
        35                  40                  45

Gln Gly Arg Cys Glu Ser Gly Glu Tyr Thr Gln Asp Tyr Val Asp Glu
    50                  55                  60

Glu Ala Leu Ser Ser Leu Asp Leu Gln Gln Arg Lys Met Leu Ser Cys
65                  70                  75                  80

Gln Thr Arg Val Lys Ser Asp Ala Thr Phe Tyr Phe Asp Phe Asp Ser
                85                  90                  95

Ser Leu Cys Asn Ala Pro Gly Pro Val Gln Val Arg Gly Thr Val Ser
            100                 105                 110

Ala Val Gln Gln Val Ser Thr Ser Thr Ala Ile Leu Gln Val Gln Leu
        115                 120                 125

Asp Gln Pro Leu Asp Phe Leu Pro Gly Gln Tyr Ala Arg Leu Ser Val
    130                 135                 140

Pro Gly Thr Asp Ser Trp Arg Ser Tyr Ser Phe Ala Asn Arg Pro Gly
145                 150                 155                 160

Asn Gln Leu Gln Phe Leu Val Arg Leu Leu Pro Asp Gly Val Met Ser
```

-continued

```
                         165                 170                 175

Asn Tyr Leu Arg Glu Arg Cys Gln Val Gly Asp Glu Met Leu Met Glu
        180                 185                 190

Ala Pro Leu Gly Ala Phe Tyr Leu Arg His Val Thr Gln Pro Leu Val
    195                 200                 205

Leu Val Ala Gly Glu Thr Gly Leu Ser Ala Leu Leu Gly Met Leu Asp
210                 215                 220

Glu Leu Val Val Asn Glu Cys Thr Gln Pro Val His Leu Tyr Tyr Gly
225                 230                 235                 240

Val Arg Gly Ala Glu Asp Leu Cys Glu Ala Ala Arg Ile His Ala Tyr
                245                 250                 255

Ala Thr Lys Ile Pro Asn Phe Arg Tyr Thr Glu Val Leu Ser Asp Ala
            260                 265                 270

Ser Val Glu Trp Thr Gly Lys Arg Gly Tyr Leu Thr Glu His Phe Asp
        275                 280                 285

Leu Ala Glu Leu Arg Asp Arg Ser Ala Asp Met Tyr Val Cys Gly Pro
    290                 295                 300

Pro Pro Met Val Glu Ser Ile Gln Gln Trp Leu Ala Asp Gln Thr Leu
305                 310                 315                 320

Asp Gly Val Gln Lys Tyr Tyr Glu Lys Phe Thr Gln Ser Asn Ile
                325                 330                 335

<210> SEQ ID NO 13
<211> LENGTH: 1544
<212> TYPE: DNA
<213> ORGANISM: Artificial Sequence
<220> FEATURE:
<223> OTHER INFORMATION: Construct containing the pDOW1057 Pant-Pben
      tandem promoter
<220> FEATURE:
<221> NAME/KEY: misc_feature
<222> LOCATION: (95)...(1395)
<223> OTHER INFORMATION: Portion containing Pant with activator CDS
<220> FEATURE:
<221> NAME/KEY: misc_feature
<222> LOCATION: (92)...(94)
<223> OTHER INFORMATION: Anticodon of stop codon for the CDS of AntR
<220> FEATURE:
<221> NAME/KEY: CDS
<222> LOCATION: (95)...(1084)
<223> OTHER INFORMATION: Antisense strand of ORF encoding AntR
<220> FEATURE:
<221> NAME/KEY: variation
<222> LOCATION: (283)...(283)
<223> OTHER INFORMATION: Mutation to A235 from native C235; resulting in
      anticodon mutation CGC->CGA, thus codon mutation
      GCG->TCG and amino acid mutation of Ala268 to
      Ser268
<220> FEATURE:
<221> NAME/KEY: misc_signal
<222> LOCATION: (1221)...(1327)
<223> OTHER INFORMATION: Approximate region estimated to contain the
      AntR binding site
<220> FEATURE:
<221> NAME/KEY: misc_feature
<222> LOCATION: (1329)...(1509)
<223> OTHER INFORMATION: Pant-Pben tandem promoter construct
<220> FEATURE:
<221> NAME/KEY: promoter
<222> LOCATION: (1329)...(1365)
<223> OTHER INFORMATION: Putative promoter (Pant) from anthranilate
      operon (antABC)
<220> FEATURE:
<221> NAME/KEY: -35_signal
<222> LOCATION: (1329)...(1333)
<223> OTHER INFORMATION: Putative -35 region of Pant promoter
<220> FEATURE:
<221> NAME/KEY: -10_signal
```

```
<222> LOCATION: (1355)...(1359)
<223> OTHER INFORMATION: Putative -10 region of Pant promoter
<220> FEATURE:
<221> NAME/KEY: misc_signal
<222> LOCATION: (1371)...(1371)
<223> OTHER INFORMATION: Putative native transcription start site under
      control of Pant
<220> FEATURE:
<221> NAME/KEY: misc_feature
<222> LOCATION: (1396)...(1429)
<223> OTHER INFORMATION: linker
<220> FEATURE:
<221> NAME/KEY: misc_feature
<222> LOCATION: (1430)...(1541)
<223> OTHER INFORMATION: Portion containing Pben
<220> FEATURE:
<221> NAME/KEY: misc_signal
<222> LOCATION: (1430)...(1476)
<223> OTHER INFORMATION: Approximate region estimated to contain the
      BenR binding site
<220> FEATURE:
<221> NAME/KEY: promoter
<222> LOCATION: (1477)...(1509)
<223> OTHER INFORMATION: Putative promoter (Pben) from benzoate operon
      (benABCD)
<220> FEATURE:
<221> NAME/KEY: -35_signal
<222> LOCATION: (1477)...(1482)
<223> OTHER INFORMATION: Putative -35 region of Pben promoter
<220> FEATURE:
<221> NAME/KEY: -10_signal
<222> LOCATION: (1498)...(1503)
<223> OTHER INFORMATION: Putative -10 region of Pben promoter
<220> FEATURE:
<221> NAME/KEY: misc_feature
<222> LOCATION: (1508)...(1508)
<223> OTHER INFORMATION: Substitution mutation of Pben -10 region by
      tataat to form -10con mutants, and by taaggt to form
      -10benAc mutants
<220> FEATURE:
<221> NAME/KEY: misc_signal
<222> LOCATION: (1509)...(1509)
<223> OTHER INFORMATION: Putative transcription start site
<220> FEATURE:
<221> NAME/KEY: misc_signal
<222> LOCATION: (1542)...(1544)
<223> OTHER INFORMATION: Putative native translation initiator codon
      attached to Pben

<400> SEQUENCE: 13
agcttgcatg cctgcaggtt taaacagtcg actctagact taattaacta tcgcaggcaa      60
gccagctccc acagattgtt tttcatccag ttca agt aat gcg cag gcg ctt gcg     115
                                       Thr Ile Arg Leu Arg Lys Arg
                                           -330            -325 ctg caa tgt ctg gct ggg cga ctc atc gaa cag ctt gcg gta ctc cgc       163
Gln Leu Thr Gln Ser Pro Ser Glu Asp Phe Leu Lys Arg Tyr Glu Ala
        -320            -315            -310 cga aaa ccg ccc caa atg cgt aaa ccc cca acc cag ggc gat ttc aga       211
Ser Phe Arg Gly Leu His Thr Phe Gly Trp Gly Leu Ala Ile Glu Ser
    -305            -300            -295 gat ggt gcg gat cga gcc ctg ctc cag aat ttc ttg gcg cac cgc ccc       259
Ile Thr Arg Ile Ser Gly Gln Glu Leu Ile Glu Gln Arg Val Ala Gly
    -290            -285            -280 caa ccg atg ctt ctt caa ata cga cat ggg cga cag tgc gaa gta ctt       307
Leu Arg His Lys Lys Leu Tyr Ser Met Pro Ser Leu Ala Phe Tyr Lys
-275            -270            -265            -260 gcg aaa cgc atc gaa cag ttt gaa acg cga cac gcc cgc cgc cgc ttc       355
Arg Phe Ala Asp Phe Leu Lys Phe Arg Ser Val Gly Ala Ala Ala Glu
        -255            -250            -245 cag gtc ttc cag gtg cag cgc ttc acg ggc gtt gtc gtg gat aaa ttg       403
Leu Asp Glu Leu His Leu Ala Glu Arg Ala Asn Asp His Ile Phe Gln
```

-continued

```
              -240              -235              -230
ccg cgc gcg gat cag gta gtg cgg cag ttt cac ccc cag cac gtc gcg      451
Arg Ala Arg Ile Leu Tyr His Pro Leu Lys Val Gly Leu Val Asp Arg
        -225              -220              -215 cag ttc ttc gga gta gtt att cgg ttg ggc cag gat cag gcc ctt gat      499
Leu Glu Glu Ser Tyr Asn Asn Pro Gln Ala Leu Leu Gly Lys Ile
        -210              -205              -200 cag cga gct ttc cag gtc gcg agt aaa cgc cgc ctg ctc gta cag ttc      547
Leu Ser Ser Glu Leu Asp Arg Thr Phe Ala Ala Gln Glu Tyr Leu Glu
        -195              -190              -185              -180 gct gct gcg ctc cag ttc ggc gat gaa ata acg cgc cat gcg cca cca      595
Ser Ser Arg Glu Leu Glu Ala Ile Phe Tyr Arg Ala Met Arg Trp Trp
                  -175              -170              -165 cga agc cgg tgc tcc gtc cac agc atc cat cac cga ctc aaa gcg cag      643
Ser Ala Pro Ala Gly Asp Val Ala Asp Met Val Ser Glu Phe Arg Leu
        -160              -155              -150 cgg cgc atc aat ggg ccg ttg cag caa acc ttc cag cga ctc gct cat      691
Pro Ala Asp Ile Pro Arg Gln Leu Leu Gly Glu Leu Ser Glu Ser Met
        -145              -140              -135 cgc cgc acg ggt gat tac cac ctg caa ctt gcg gca gtc acc gga aat      739
Ala Ala Arg Thr Ile Val Val Gln Leu Lys Arg Cys Asp Gly Ser Ile
        -130              -125              -120 cgc cag cac ctg atg ctc att ggg cga aat gat cac gcc ttg gtc gcg      787
Ala Leu Val Gln His Glu Asn Pro Ser Ile Ile Val Gly Gln Asp Arg
-115              -110              -105              -100 gtt gga act gag acg ttc acc gtt ctt gct cag ctc ctg ctc gcc cac      835
Asn Ser Ser Leu Arg Glu Gly Asn Lys Ser Leu Glu Gln Glu Gly Val
              -95               -90               -85 cag tgg cag gct caa gct gta gct gct gaa gtg ctc ggc gtc ttc gat      883
Leu Pro Leu Ser Leu Ser Tyr Ser Ser Phe His Glu Ala Asp Glu Ile
        -80               -75               -70 gtc gat ggt cac atc agt gcc gta ctc gat cac gcc cag ggt ggt ggc      931
Asp Ile Thr Val Asp Thr Gly Tyr Glu Ile Val Gly Leu Thr Thr Ala
        -65               -60               -55 gcg gga ttt gaa cac gtt ggc gct gtg gtg aaa gcg cag gcg ctc ggg      979
Arg Ser Lys Phe Val Asn Ala Ser His His Phe Arg Leu Arg Glu Pro
        -50               -45               -40 ggt tgc cgt cgc cag gcg atg ggg ccc gca gat gcc gga cat cca gct     1027
Thr Ala Thr Ala Leu Arg His Pro Gly Cys Ile Gly Ser Met Trp Ser
-35               -30               -25               -20 gcg cgc gcc ttc cag gtc gaa gcg ttg aat atg aat atc gcg tgt ctg     1075
Arg Ala Gly Glu Leu Asp Phe Arg Gln Ile His Ile Asp Arg Thr Gln
              -15               -10               -5 act agt cat caggstgcac ccacggcggt taggcgtttg cgcgctctga             1124
Ser Thr Met
        -1 cggcgcgtcg ttgaacctcg acagcaagtt ccaggccacg ccagtgcagt tctcactggg   1184
tggatagcaa cggtcgacta tgtggataaa ccccagagtt ttgcgaccat cgcccgccat   1244
cacagtagcg catgccgtca ccggcgcgca ccgtcatggg tatttgccgc caactttgc    1304 ggcctacgtt cccccattaa gcggatagcc cgccaccgca tcgcagccgc ttaatggctc   1364
accgtttagc catgatcaaa aggtgcctcc cggatcccca aacagtcgac tctagactta   1424
attaagttaa gcgacgtgcg cctggcggat agcgatgtgc aggcagcgga tattgacggg   1484
cagggcgagc acgtacggtg agggcgcctg atacaagaac aacggagggc ccgcccc      1541 atg                                                                 1544
Met
1
```

<210> SEQ ID NO 14
<211> LENGTH: 20
<212> TYPE: DNA
<213> ORGANISM: Artificial Sequence
<220> FEATURE:
<221> NAME/KEY: misc_feature
<222> LOCATION: 1..20
<223> OTHER INFORMATION: Alternative Inter-promoter linker for tandem promoter

<400> SEQUENCE: 14
ggatccggcg cgcccccatc                                                   20

<210> SEQ ID NO 15
<211> LENGTH: 18
<212> TYPE: DNA
<213> ORGANISM: Artificial Sequence
<220> FEATURE:
<221> NAME/KEY: misc_feature
<222> LOCATION: 1..18
<223> OTHER INFORMATION: Linker used to connect promoters to reporter genes

<400> SEQUENCE: 15
actagtagga ggtaactt                                                     18

<210> SEQ ID NO 16
<211> LENGTH: 21
<212> TYPE: DNA
<213> ORGANISM: Artificial Sequence
<220> FEATURE:
<221> NAME/KEY: misc_feature
<222> LOCATION: 1..21
<223> OTHER INFORMATION: Knock-out primer AntAKO5
<220> FEATURE:
<221> NAME/KEY: misc_feature
<222> LOCATION: (2)...(7)
<223> OTHER INFORMATION: EcoRI recognition site

<400> SEQUENCE: 16
ggaattcttc gtgacgatgc g                                                 21

<210> SEQ ID NO 17
<211> LENGTH: 22
<212> TYPE: DNA
<213> ORGANISM: Artificial Sequence
<220> FEATURE:
<221> NAME/KEY: misc_feature
<222> LOCATION: 1..22
<223> OTHER INFORMATION: Knock-out primer AntAKO3
<220> FEATURE:
<221> NAME/KEY: misc_feature
<222> LOCATION: (3)...(8)
<223> OTHER INFORMATION: BamHI recognition site

<400> SEQUENCE: 17
cgggatccgc tcgcgatgct gc                                                22

<210> SEQ ID NO 18
<211> LENGTH: 16
<212> TYPE: DNA
<213> ORGANISM: Artificial Sequence
<220> FEATURE:
<223> OTHER INFORMATION: Labeling primer lacZPE

<400> SEQUENCE: 18
ggatgtgctg caaggc                                                       16

```
<210> SEQ ID NO 19
<211> LENGTH: 17
<212> TYPE: DNA
<213> ORGANISM: Artificial Sequence
<220> FEATURE:
<221> NAME/KEY: misc_feature
<222> LOCATION: 1..17
<223> OTHER INFORMATION: Labeling primer lacZPE2

<400> SEQUENCE: 19
gtaaccatgg tcatcgc                                                 17

<210> SEQ ID NO 20
<211> LENGTH: 17
<212> TYPE: DNA
<213> ORGANISM: Artificial Sequence
<220> FEATURE:
<221> NAME/KEY: misc_feature
<222> LOCATION: 1..17
<223> OTHER INFORMATION: M13forward primer

<400> SEQUENCE: 20
gtaaaacgac ggccagt                                                 17

<210> SEQ ID NO 21
<211> LENGTH: 16
<212> TYPE: DNA
<213> ORGANISM: Artificial Sequence
<220> FEATURE:
<221> NAME/KEY: misc_feature
<222> LOCATION: 1..16
<223> OTHER INFORMATION: M13reverse primer

<400> SEQUENCE: 21
aacagctatg accatg                                                  16

<210> SEQ ID NO 22
<211> LENGTH: 35
<212> TYPE: DNA
<213> ORGANISM: Artificial Sequence
<220> FEATURE:
<221> NAME/KEY: misc_feature
<222> LOCATION: 1..35
<223> OTHER INFORMATION: Oligonucleotide Bambenwtshort

<400> SEQUENCE: 22
cgggatccgt atcaggcgcc tcaccgtacg tgctc                             35

<210> SEQ ID NO 23
<211> LENGTH: 35
<212> TYPE: DNA
<213> ORGANISM: Artificial Sequence
<220> FEATURE:
<221> NAME/KEY: misc_feature
<222> LOCATION: 1..35
<223> OTHER INFORMATION: Oligonucleotide Bambenconshort

<400> SEQUENCE: 23
cgggatccgt atcaggcgcc tcattatacg tgctc                             35

<210> SEQ ID NO 24
<211> LENGTH: 35
<212> TYPE: DNA
<213> ORGANISM: Artificial Sequence
<220> FEATURE:
<221> NAME/KEY: misc_feature
<222> LOCATION: 1..35
<223> OTHER INFORMATION: Oligonucleotide BambenAcshort
```

```
<400> SEQUENCE: 24
cgggatccgt atcaggcgcc tcaccttacg tgctc                              35

<210> SEQ ID NO 25
<211> LENGTH: 35
<212> TYPE: DNA
<213> ORGANISM: Artificial Sequence
<220> FEATURE:
<221> NAME/KEY: misc_feature
<222> LOCATION: 1..35
<223> OTHER INFORMATION: Oligonucleotide Bamantwtshort

<400> SEQUENCE: 25
cgggatccgc taacggtgag ccattaagcg gctgc                              35

<210> SEQ ID NO 26
<211> LENGTH: 35
<212> TYPE: DNA
<213> ORGANISM: Artificial Sequence
<220> FEATURE:
<221> NAME/KEY: misc_feature
<222> LOCATION: 1..35
<223> OTHER INFORMATION: Oligonucleotide Bamantconshort

<400> SEQUENCE: 26
cgggatccgc taacggtgag cattatagcg gctgc                              35

<210> SEQ ID NO 27
<211> LENGTH: 20
<212> TYPE: DNA
<213> ORGANISM: Artificial Sequence
<220> FEATURE:
<221> NAME/KEY: misc_feature
<222> LOCATION: 1..20
<223> OTHER INFORMATION: Primer BenactKO-for

<400> SEQUENCE: 27
cgcgacacat tgctgcccag                                               20

<210> SEQ ID NO 28
<211> LENGTH: 20
<212> TYPE: DNA
<213> ORGANISM: Artificial Sequence
<220> FEATURE:
<221> NAME/KEY: misc_feature
<222> LOCATION: 1..20
<223> OTHER INFORMATION: Primer BenactKO-rev

<400> SEQUENCE: 28
agtatcagcc atcgcacctt                                               20

<210> SEQ ID NO 29
<211> LENGTH: 19
<212> TYPE: DNA
<213> ORGANISM: Artificial Sequence
<220> FEATURE:
<221> NAME/KEY: misc_feature
<222> LOCATION: 1..19
<223> OTHER INFORMATION: Primer 1803H3seq

<400> SEQUENCE: 29
gtcctgcaat ttcagccga                                                19

<210> SEQ ID NO 30
<211> LENGTH: 26
<212> TYPE: DNA
```

```
<213> ORGANISM: Artificial Sequence
<220> FEATURE:
<221> NAME/KEY: misc_feature
<222> LOCATION: 1..26
<223> OTHER INFORMATION: Oligonucleotide BenL278

<400> SEQUENCE: 30
ccttaattaa gttaagcgac gtgcgc                                          26

<210> SEQ ID NO 31
<211> LENGTH: 26
<212> TYPE: DNA
<213> ORGANISM: Artificial Sequence
<220> FEATURE:
<221> NAME/KEY: misc_feature
<222> LOCATION: 1..26
<223> OTHER INFORMATION: Oligonucleotide 3'Antactiv

<400> SEQUENCE: 31
cccaagcttc tatcgaggca agccag                                          26

<210> SEQ ID NO 32
<211> LENGTH: 32
<212> TYPE: DNA
<213> ORGANISM: Artificial Sequence
<220> FEATURE:
<221> NAME/KEY: misc_feature
<222> LOCATION: 1..32
<223> OTHER INFORMATION: Oligonucleotide Benact5'

<400> SEQUENCE: 32
agctttgttt aaacgcatga cgttgttgat tc                                   32

<210> SEQ ID NO 33
<211> LENGTH: 31
<212> TYPE: DNA
<213> ORGANISM: Artificial Sequence
<220> FEATURE:
<221> NAME/KEY: misc_feature
<222> LOCATION: 1..31
<223> OTHER INFORMATION: Oligonucleotide H3_5'BenAKOclean

<400> SEQUENCE: 33
cccaagcttg ccatgaggcg gaaaacgctg c                                    31

<210> SEQ ID NO 34
<211> LENGTH: 30
<212> TYPE: DNA
<213> ORGANISM: Artificial Sequence
<220> FEATURE:
<221> NAME/KEY: misc_feature
<222> LOCATION: 1..30
<223> OTHER INFORMATION: Oligonucleotide H3_3'BenBKOclean

<400> SEQUENCE: 34
cccaagcttc ggtgatcgcc acgctgtcgc                                      30

<210> SEQ ID NO 35
<211> LENGTH: 25
<212> TYPE: DNA
<213> ORGANISM: Artificial Sequence
<220> FEATURE:
<221> NAME/KEY: misc_feature
<222> LOCATION: 1..25
<223> OTHER INFORMATION: Oligonucleotide BenKOmega

<400> SEQUENCE: 35
catacgtcat ggccctccgt tgttc                                           25
```

<210> SEQ ID NO 36
<211> LENGTH: 25
<212> TYPE: DNA
<213> ORGANISM: Artificial Sequence
<220> FEATURE:
<221> NAME/KEY: misc_feature
<222> LOCATION: 1..25
<223> OTHER INFORMATION: Oligonucleotide InvbenKOmega

<400> SEQUENCE: 36
gaacaacgga gggccatgac gtatg                                            25

<210> SEQ ID NO 37
<211> LENGTH: 24
<212> TYPE: DNA
<213> ORGANISM: Artificial Sequence
<220> FEATURE:
<221> NAME/KEY: misc_feature
<222> LOCATION: 1..24
<223> OTHER INFORMATION: Oligonucleotide 5'BenA_seq

<400> SEQUENCE: 37
ctgctggaaa acgcctgcct ggag                                             24

<210> SEQ ID NO 38
<211> LENGTH: 25
<212> TYPE: DNA
<213> ORGANISM: Artificial Sequence
<220> FEATURE:
<221> NAME/KEY: misc_feature
<222> LOCATION: 1..25
<223> OTHER INFORMATION: Oligonucleotide Seq_3'BenB

<400> SEQUENCE: 38
gagcacttca agcatcgaca ggaac                                            25

<210> SEQ ID NO 39
<211> LENGTH: 21
<212> TYPE: DNA
<213> ORGANISM: Artificial Sequence
<220> FEATURE:
<221> NAME/KEY: misc_feature
<222> LOCATION: 1..21
<223> OTHER INFORMATION: Primer 1261-8378F

<400> SEQUENCE: 39
cttcagatcc agactcacca g                                                21

<210> SEQ ID NO 40
<211> LENGTH: 21
<212> TYPE: DNA
<213> ORGANISM: Artificial Sequence
<220> FEATURE:
<221> NAME/KEY: misc_feature
<222> LOCATION: 1..21
<223> OTHER INFORMATION: Primer 1261-103R

<400> SEQUENCE: 40
gaccatgatt acgccaagcg c                                                21

<210> SEQ ID NO 41
<211> LENGTH: 21
<212> TYPE: DNA
<213> ORGANISM: Artificial Sequence
<220> FEATURE:
<221> NAME/KEY: misc_feature
<222> LOCATION: 1..21

```
<223> OTHER INFORMATION: Primer M13R21

<400> SEQUENCE: 41
cacacaggaa acagctatga c                                              21

<210> SEQ ID NO 42
<211> LENGTH: 7
<212> TYPE: DNA
<213> ORGANISM: Escherichia coli

<400> SEQUENCE: 42 aaggaag                                                               7

<210> SEQ ID NO 43
<211> LENGTH: 6
<212> TYPE: DNA
<213> ORGANISM: Bacillus subtilis

<400> SEQUENCE: 43 gagagg                                                                6

<210> SEQ ID NO 44
<211> LENGTH: 7
<212> TYPE: DNA
<213> ORGANISM: Pseudomonas fluorescens

<400> SEQUENCE: 44 tacggtt                                                               7

<210> SEQ ID NO 45
<211> LENGTH: 6
<212> TYPE: DNA
<213> ORGANISM: Artificial Sequence
<220> FEATURE:
<223> OTHER INFORMATION: -10 region consensus sequence

<400> SEQUENCE: 45 tataat                                                                6

<210> SEQ ID NO 46
<211> LENGTH: 6
<212> TYPE: DNA
<213> ORGANISM: Acinetobacter

<400> SEQUENCE: 46 taaggt                                                                6
```